(12) United States Patent
Creelman et al.

(10) Patent No.: US 10,407,689 B2
(45) Date of Patent: Sep. 10, 2019

(54) MUTATION OF THE EAR MOTIF OF CLASS II HD-ZIP POLYPEPTIDES

(71) Applicant: Mendel Biotechnology, Inc., Hayward, CA (US)

(72) Inventors: Robert A. Creelman, Castro Valley, CA (US); Marjorie R. Lundgren, South Yorkshire (GB); Suqin Cai, Fremont, CA (US); Hans E. Holtan, Emeryville, CA (US); Graham J. Hymus, Castro Valley, CA (US); Oliver J. Ratcliffe, Hayward, CA (US); T. Lynne Reuber, San Mateo, CA (US); Amanda J. Burek, Alameda, CA (US); Shiv B. Tiwari, San Jose, CA (US); Luc J. Adam, Hayward, CA (US); Colleen M. Marion, San Mateo, CA (US); Megan Lau, San Mateo, CA (US); Bonnie R. Brayton, Honolulu, HI (US); Yu Shen, Union City, CA (US)

(73) Assignee: Mendel Biotechnology, Inc., Hayward, CA (US)

(*) Notice: Subject to any disclaimer, the term of this patent is extended or adjusted under 35 U.S.C. 154(b) by 0 days.

(21) Appl. No.: 15/671,023

(22) Filed: Aug. 7, 2017

(65) Prior Publication Data

US 2018/0087067 A1 Mar. 29, 2018

Related U.S. Application Data

(63) Continuation of application No. 14/387,227, filed as application No. PCT/US2013/035640 on Apr. 8, 2013, now Pat. No. 9,758,791.

(60) Provisional application No. 61/621,980, filed on Apr. 9, 2012.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8269* (2013.01); *Y02A 40/146* (2018.01)

(58) Field of Classification Search
None
See application file for complete search history.

(56) References Cited

U.S. PATENT DOCUMENTS 7,511,190 B2    3/2009    Sherman et al.
9,758,791 B2 *  9/2017    Creelman ............ C07K 14/415

OTHER PUBLICATIONS

Harris et al. Modulation of plant growth by HD-Zip class I and II transcription factors in response to environmental stimuli. New Phytol. Jun. 2011;190(4):823-37. Epub Apr. 21, 2011. Review. (Year: 2011).*
Ciarbelli et al. The Arabidopsis homeodomain-leucine zipper II gene family: diversity and redundancy.Plant Mol Biol. Nov. 2008;68(4-5):465-78. Epub Aug. 30, 2008. (Year: 2008).*
Li et al. Identical amino acid substitutions in the repression domain of auxin/indole-3-acetic acid proteins have contrasting effects on auxin signaling. Plant Physiol. Mar. 2011;155(3):1252-63. Epub Jan. 20, 2011. (Year: 2011).*
Falcon-Perez et al., "Functional domain analysis of the yeast ABC transporter Ycf1p by site-directed mutagenesis", *J Biol. Chem.*, 274(33):23584-90, Aug. 13, 1999.
Hill et al., "Functional analysis of conserved histidines in ADP-glucose pyrophosphorylase from *Escherichia coli*", *Biochem Biophys Res Commun.*, 244(2):573-7, Mar. 17, 1998.
Harris et al., "Modulation of plant growth by HD-Zip class I and II transcription factors in response to environmental stimuli", *New Phytol.*, 190(4):823-37, Jun. 2011, Epub. Apr. 21, 2011, Review.
Ciarbelli et al., "The Arabidopsis homeodomain-leucine zipper II gene family: diversity and redundancy", *Plant Mol. Biol.*, 68(4-5):465-78, Nov. 2008, Epub. Aug. 30, 2008.
Li et al., "Identical amino acid substitutions in the repression domain of auxin/indole-3-acetic acid proteins have contrasting effects on auxin signaling", *Plant Physiol.*, 155(3):1252-63, Mar. 2011, Epub. Jan. 20, 2011.
Affolter et al., "DNA binding properties of the purified Antennapedia homeodomain," *Proc. Natl. Acad. Sci. U.S.A.*, 87,4093-4097, 1990.
Ariel et al., "The true story of the HD-Zip family," *Trends Plant Sci.*, 12(9):419-426, 2007.
Aso et al., "Characterization of homrodomain-leucine zipper genes in the fern Ceratopteris richardii and the evolution of the homeodomain-leucine zipper gene family in vascular Plants," *Mol. Biol. Evol.*, 16(4):544-552, 1999.
Aubert et al., "RD20, a strees-inducible caleosin, participates in stomatal control, transpiration and drought tolerance in *Arabidopsis thaliana,*" *Plant Cell Physiol.*, 51(12):1975-1987, 2010.
Carabelli et al., "The Arabidopsis Athb-2 and—4 genes are strongly induced by far-red-rich light," *Plant J*, 4(3):469-479, 1993.
Chardon et al., "Natural variation of nitrate uptake and nitrogen use efficiency in *Arabidopsis thaliana* cultivated with limiting and ample nitrogen supply," *J Exp. Bot.*, 61(9):2293-2302, 2010.
Ciarbelli et al., "The Arabidopsis homeodomain-leucine zipper II gene family: diversity and redundancy," Plant Mol Biol 68:465-478, 2008.
Cominelli et al., "A guard-cell-specific MYB transcription factor regulates stomatal movements and plant drought tolerance," *Curr. Biol.*, 15:1196-1200, 2005.

(Continued)

Primary Examiner — Cynthia E Collins
(74) Attorney, Agent, or Firm — Dentons US LLP; David Lanzotti

(57) ABSTRACT

The application describes producing polynucleotide variants of the AtHB 17 clade members and introducing the mutant variants into plants to improve plant traits. The mutant polynucleotides encode polypeptides that comprise mutations in the EAR motifs.

18 Claims, 18 Drawing Sheets

Figure 2A:
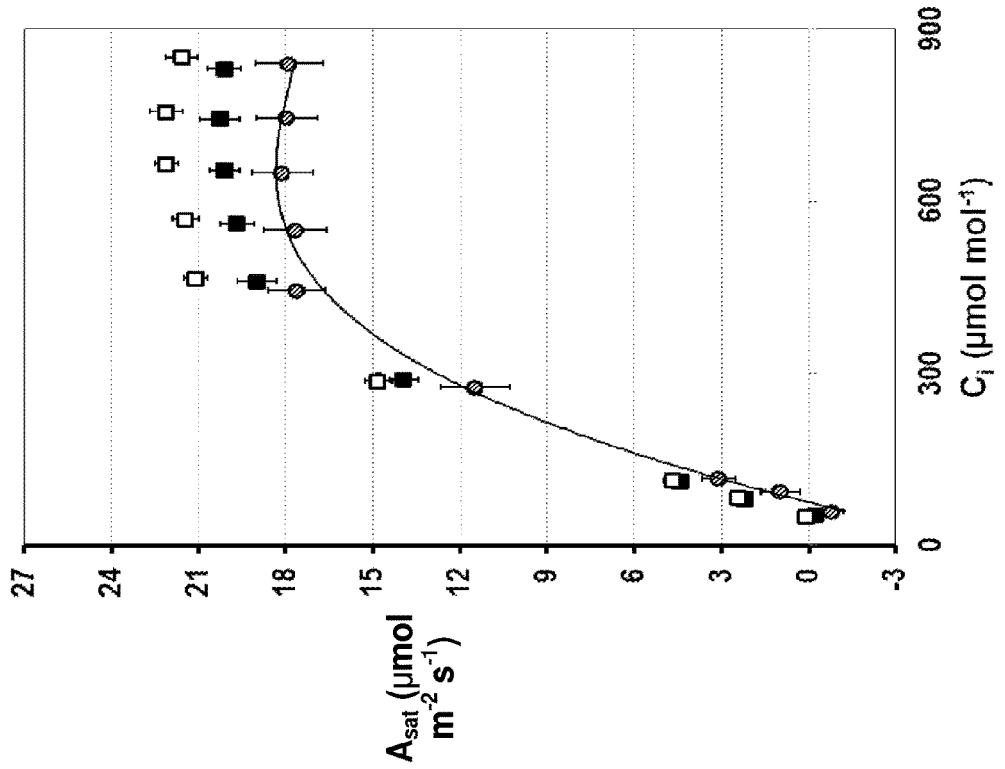

Specification includes a Sequence Listing.

(56) References Cited

OTHER PUBLICATIONS

Gosti et al., "ABI1 Protein Phosphatase 2C is a Negative Regulator of Abscisic Acid Signaling," *J Plant Cell*, 11:1897-1910, 1999.

Hanes et al., "DNA Specificity of the Bicoid Activator Protein is determined by Homeodomain Recognition Helix Residue 9," *Cell*, 57:1275-1283, 1989.

Hayashi et al., "What determines the specificity of action of *Drosophila* homeodomain proteins?" *Cell*, 63:883-894, 1990.

Hill et al., "A transcriptional repression motif in the MADS factor AGL15 is involved in recruitment of histone deacetylase complex components," *Plant J*, 53:172-185, 2008.

Ikeda et al., "A novel group of transcriptional repressors in Arabidopsis," *Plant Cell Physiol.*, 50:970-975, 2009.

Kagale et al., "Genome-wide analysis of ethylene-responsive element binding factor-associated amphiphilic repression motif-containing transcriptional regulators in Arabidopsis," *Plant Physiol.*, 152:1109-1134, 2010.

Lebaudy et al., "Plant adaptation to fluctuating environment and biomass production are strongly dependent on guard cell potassium channels," *Proc Natl. Acad. Sci. U.S.A.*, 105(13):5271-5276, 2008.

Lee et al., "Activation of glucosidase via stress-induced polymerization rapidly increases active pools of abscisic acid," *Cell*, 126(6):1109-20, 2006.

Lemaitre et al., "Enzymatic and metabolic diagnostic of nitrogen deficiency in *Arabidopsis thaliana* Wassileskija accession," *Plant Cell Physiol.*, 49:1056-1065, 2008.

Mori et al., "CDPKs CPK6 and CPK3 Function in ABA Regulation of Guard Cell S-Type Anion—and Ca2+— Permeable Channels and Stomata! Closure," *PLoS. Biol.*, 4(10):1749-1762, 2006.

Ohgishi et al., "Negative autoregulation of the Arabidopsis homeobox gene ATHB-2," *Plant J*, 25(4):389-398, 2001.

Ruberti et al., "A novel class of plant proteins containing a homeodomain with a closely linked leucine zipper motif," *Embo J*, 10(7):1787-1791, 1991.

Sato et al., "Modulation of the Arabidopsis KAT1 channel by an activator of protein kinase C in Xenopus laevis oocytes," *FEBS J277*, (10):2318-2328, 2010.

Sawa et al., "The HAT2 gene, a member of the HD-Zip gene family, isolated as an auxin inducible gene by DNA microarray screening, affects auxin response in Arabidopsis," *Plant J*, 32(6):1011-1022, 2002.

Schena et al., "The HAT4 gene of Arabidopsis encodes a developmental regulator," *Genes Dev.*, 7:367-379, 1993.

Sessa et al., "The Athb-1 and—2 HD-Zip domains homodimerize forming complexes of different DNA binding specificities," *Embo J*, 12(9):3507-3517, 1993.

Good et al., "Can less yield more? Is reducing nutrient input into the environment compatible with maintaining crop production?," *Trends Plant Sci.*, 9(12):597-605, 2004.

Steindler et al., "Shade avoidance responses are mediated by the ATHB-2 HD-Zip protein, a negative regulator of gene expression," *Development*, 126:4235-4245, 1999.

Szemenyei et al., "Topless mediates auxin-dependent transcriptional repression during Arabidopsis embryogenesis," *Science*, 319(5868):1384-1386, 2008.

Tiwari et al., "Aux/IAA proteins contain a potent transcriptional repression Domain," *Plant Cell*, 16:533-543, 2004.

Conserved protein domain family, "smart00389: Hox," available at www.ncbi.nlm.nih.gov/Structure/cdd/cddsrv.cgi?ascbin=8&maxaln+10&seltype=2&uid=197 696, Accessed Mar. 30. 2015.

Zhu et al., "Improving Photosynthetic Efficiency for Greater Yield," *Annual Review of Plant Biology*, 61:235-261, 2010.

\* cited by examiner

| | |
|---|---|
| ZmHB17 | (6) |
| SbHB17 | (12) |
| OsHOX3 | (4) |
| G4370 | (7) |
| AtHB18 | (8) |
| AlHB18 | (18) |
| AtHB17 | (2) MIKLLFTYICTYTYKLYALYHMDYACVCMYKYKGIVTLQVCLFYIKLRVFLSNFTFSSSI |
| AlHB17 | (19) |
| ThHB17 | (16) |
| G3524 | (3) |
| G4371 | (5) |
| CpHB17 | (14) |
| VvHB17 | (13) |
| PtHB17 | (15) |
| RcHB17 | (17) |
| AtHAT1 | (11) |
| AtHAT2 | (10) |
| AtHB2 | (9) |

Fig. 1A

```
ZmHB17   (6)   ----------------------------------MGSTSPSGLELTMA----------------VPGLSSSSGSEGFGC
SbHB17  (12)   ----------------------------------MGSTSPSGLELTMA----------------VPGLSSSSGSEGFGC
OsHOX3   (4)   ---------------------------------MMGATSPSGLELTMA----------------VPGLSSS-GSEGAGC
G4370    (7)   ----------------------------------MGATSPSGLELTMA----------------VPGLSSSSGSEGFVC
AtHB18   (8)   -----------------------------MALSP-NSSSLDLTIS-------------------IPSFSPSPSLGDH--
AlHB18  (18)   -----------------------------MALSP-NSSSLDLTIS-------------------IPSFSPSPSLGDHD-
AtHB17   (2)   LALKNPNNSLIKIMAILPENSSNLDLTIS-----------------------------------VPGFSSSPLSDEGSG
AlHB17  (19)   -----------------------------MAILPENSSNLDLTIS-------------------VPGFSSSPPSDEGSG
ThHB17  (16)   -----------------------------MAILPENSSNLDLSIS-------------------VPGFSSSPPSDEGSG
G3524    (3)   -----------------------------MAVLPSSSSSLELTIS-------------------VPGFASSPTLLP---
G4371    (5)   -----------------------------MAVLPSSSSSLELTIS-------------------VPGFASSPTLLP---
CpHB17  (14)   -----------------------------MAVLPTNSSSLELTIS-------------------VPGFASSPPLP----
VvHB17  (13)   -----------------------------MDVIPMRSSSLELTIS-------------------VPGFTSSPSLPSSAD
PtHB17  (15)   -----------------------------MAVSRSSSSSLELTMS-------------------MPGVCA---------
RcHB17  (17)   -----------------------------MAISPSSSSSLELTIS-------------------MPGFASSPSVPSY--
AtHAT1  (11)   -------------------MMMGKEDLGLSLSLGFAQNH-PLQLN-------------------LKPTSSPMSNLQMFPW
AtHAT2  (10)   -------------------MMMGKEDLGLSLSLGFSQNHNPLQMN-------------------LNPNSLSNNLQRLPW
AtHB2    (9)   -------------------MMFEKDDLGLSLGLNFPKKQINLKSNPSVSVTPSSSSFGLFRRSSW
                                              *  *       * :
                                              Ear motif
```

Fig. 1B

```
ZmHB17  (6)   NNNNGSG------    ------NGNNMRDLDMNQPASGGEEEEFPMG-SVEEEEDERGGAGG--
SbHB17  (12)  NNN-GNG------    ------NGNNMRDLDMNQPASGGEEEEFPMG-SVEEEEDERGGAGGR-
OsHOX3  (4)   NNNNAG-------    ------GGCNMRDLDINQPASGGEEEEFPMG-SVEEDEEER-GVGG--
G4370   (7)   NNNNISNN-----    ------GGGNMRDLDMNQPASGGEEEDFLMG-GVEEDEEER-GAGG--
AtHB18  (8)   -------------    ------HGMRDFDINQTPKTEEDREW-MIGATPHVNEDDSNSGG---
AlHB18  (18)  -------------    ------HGVRDLDINQTPKTEEDREWIMIGATPHVNEDDSNPGG---
AtHB17  (2)   -------------    ------GGRDQLRLDMNRLP------SSEDGDDEEFSHDDGSA---
AlHB17  (19)  -------------    ------GGRDQLKLDMNRLP------SSEDGDDEEFSHD-GSA---
ThHB17  (16)  -------------    ------RGREQLKLDMNRLP------SSE--EDEEFSHG-GSA---
G3524   (3)   -------------    ------SSSVKELDINQVP----LEEDW-MA-SNMEDEEES-SNGE--
G4371   (5)   -------------    ------SSSVKELDINQVP----LEEDW-MA-SNMEDEEES-SNGE--
CpHB17  (14)  -------------    ------SCVKELDINQVPS--GEEEW-TAGATVEEEES-SNGG---
VvHB17  (13)  GKKTGE-------    ------GVCGVRDLDINQVPL-GAEEEW-TT-GSMEDEEES-GNGG--
PtHB17  (15)  -------------    ------VKDFDINQVPSGAAEEEW-IS-AGMEDEEES-TDGA---
RcHB17  (17)  -------------    ------GEGVKDLDINQLPAGVAEEEW-IT-AGIEDEEESNINGG--
AtHAT1  (11)  NQTLVS-------    SSDQQKQQFLRKIDVNSLPTTVDL-EEETGVSSPNSTISSTVSGKRRS
AtHAT2  (10)  NQTFDP-------    TSD------LRKIDVNSFPSTVNC-EEDTGVSSPNSTISSTISGKR--
AtHB2   (9)   NESFTSSVPNSDSSQKETRTFIRGIDVNRPPSTAEYGDEDAGVSSPNSTVSSS-TGKR--
                                                  :.:.*                  .
```

Fig. 1C

```
ZmHB17    (6)   ------------------------------------------------PHRAKKLRLSKEQSRLLEESF
SbHB17    (12)  ------------------------------------------------GPHRSKKLRLSKEQSRLLEESF
OsHOX3    (4)   ------------------------------------------------PHRPKKLRLSKEQSRLLEESF
G4370     (7)   ------------------------------------------------PHRPKKLRLSKEQSRLLEESF
AtHB18    (8)   ------------------------------------------------RRRKKLRLTKEQSHLLEESF
AlHB18    (18)  ------------------------------------------------RRRKKLRLTKEQSHLLEESF
AtHB17    (2)   ------------------------------------------------PPRKKLRLTREQSRLLEDSF
AlHB17    (19)  ------------------------------------------------PPRKKLRLTREQSRLLEDSF
ThHB17    (16)  ------------------------------------------------PPRKKLRLTKEQSRLLEESF
G3524     (3)   ------------------------------------------------PPRKKLRLTKEQSLLLEESF
G4371     (5)   ------------------------------------------------PPRKKLRLTKEQSRLLEESF
CpHB17    (14)  ------------------------------------------------PPRKKLRLSKEQSRLLEESF
VvHB17    (13)  ------------------------------------------------PPRKKLRLSKDQSRLLEESF
PtHB17    (15)  ------------------------------------------------PPRKKLRLSKEQSRLLEESF
RcHB17    (17)  ------------------------------------------------PPRKKLRLSKEQSRLLEESF
AtHAT1    (11)  TEREGTSGGGCG---DDLDITLDRSSSRGTSDEEEDYGGETCRKKLRLSKDQSAVLEDTF
AtHAT2    (10)  SEREGISGTGVGSGDDHDEITPDRGYSRGTSDEEED-GGETSRKKLRLSKDQSAFLEETF
AtHB2     (9)   SEREEDT---------------DPQGSRGISDDEDG---DNSRKKLRLSKDQSAILEETF
                                                                  *****:****:*:.::.**
                                                                   Homeodomain
```

Fig. 1D

| | | Homeodomain | | HALZ | |
|---|---|---|---|---|---|
| ZmHB17 | (6) | RLNHTLTPKQKEALAVKLKLRPRQVEVWF | QNRRARTKLKQ | TELECEYLKRCFGSLTEENR | |
| SbHB17 | (12) | RFNHTPTPKQKEALAGKLQLRPRQVEVWF | QNRRARTKLKQ | TELECEYLKRCFGSLTEENR | |
| OsHOX3 | (4) | RLNHTLTPKQKEALAIKLKLRPRQVEVWF | QNRRARTKLKQ | TEMECEYLKRCFGSLTEENR | |
| G4370 | (7) | RLNHTLSPKQKEALAIKLKLRPRQVEVWF | QNRRARTKLKH | TEMECEYLKRCFGSLTEENR | |
| AtHB18 | (8) | IQNHTLTPKQKKDLATFLKLSQRQVEVWF | QNRRARSKLKH | TEMECEYLKRWFGSLKEQNR | |
| AlHB18 | (18) | IQNHTLTPKQKKDLATFLKLSQRQVEVWF | QNRRARSKLKH | TEMECEYLKRWFGSLKEQNR | |
| AtHB17 | (2) | RQNHTLNPKQKEVLAKHLMLRPRQIEVWF | QNRRARSKLKQ | TEMECEYLKRWFGSLTEENH | |
| AlHB17 | (19) | RQNHTLNPKQKEALAKHLMLRPRQIEVWF | QNRRARSKLKQ | TEMECEYLKRWFGSLTEQNH | |
| ThHB17 | (16) | RQNHTLNPKQKESLAMQLKLRPRQIEVWF | QNRRARSKLKQ | TEMECEYLKRWFGSLTEQNR | |
| G3524 | (3) | RQNHTLNPKQKESLAMQLKLRPRQVEVWF | QNRRARSKLKQ | TEMECEYLKRWFGSLTEQNR | |
| G4371 | (5) | RQNHTLNPKQKETLATQLKLRPRQVEVWF | QNRRARSKLKQ | TEMECEYLKRWFGSLTEQNR | |
| CpHB17 | (14) | RQNHTLNPKQKEALAMQLKLRPRQVEVWF | QNRRARSKLKQ | TEMECEYLKRWFGSLTEQNR | |
| VvHB17 | (13) | RQNHTLNPKQKEALALQLKLRPRQVEVWF | QNRRARSKLKQ | TEMECEYLKRWFGSLTEQNR | |
| PtHB17 | (15) | RQHHSLNPRQKEALAMQLKLRPRQVEVWF | QNRRARSKLKQ | TEMECEYLKRWFGSLTEQNR | |
| RcHB17 | (17) | RQHHTLNPRQKEALAMQLKLRPRQVEVWF | QNRRARSKLKQ | TEMECEYLKRWFGSLTEQNR | |
| AtHAT1 | (11) | KEHNTLNPKQKLALAKKLGLTARQVEVWF | QNRRARTKLKQ | TEVDCEYLKRCVEKLTEENR | |
| AtHAT2 | (10) | KEHNTLNPKQKLALAKKLNLTARQVEVWF | QNRRARTKLKQ | TEVDCEYLKRCVEKLTEENR | |
| AtHB2 | (9) | KDHSTLNPKQALAKQLGLRARQVEVWF | QNRRARTKLKQ | TEVDCEFLRRCCENLTEENR | |

Fig. 1E

| | | HALZ | | CPSCE or CPRCE | |
|---|---|---|---|---|---|
| ZmHB17 | (6) | RLQREVEELRAMRVAPPTVLSPHTRQPLPASALTM | CPRCERITAATAA | ------------ |
| SbHB17 | (12) | RLQREVEELRAMRVAPPTVLSPHSRQPLPASALTM | CPRCERITAATAA | ------------ |
| OsHOX3 | (4) | RLQREVEELRAMRVAPPTVLSPHTRQPLPASALTM | CPRCERITAATGP | ------------ |
| G4370 | (7) | RLQREVEELRAMRMAPPTVLSPHTRQPLPASALTM | CPRCERVTAATCP | ------------ |
| AtHB18 | (8) | RLQIEVEELRALKPSS---------------TSALTM | CPRCERVTDAVD | ------------ |
| AlHB18 | (18) | RLQIEVEELRALKPSS---------------TSALTM | CPRCERVTDAAD | ------------ |
| AtHB17 | (2) | RLHREVEELRAIKVGPTTVNS------------ASSLTM | CPRCERVTPAAS | ------------ |
| AlHB17 | (19) | RLHREVEELRAMKVGPTTVNS------------ASSLTM | CPRCERVTAAS | ------------ |
| ThHB17 | (16) | RLHREVEELRTMKVGPPTVTS------------TASLTM | CPRCERVTTATS | ------------ |
| G3524 | (3) | RLQREVEELRAIKVGPPTVISPHSCEPLPASTLSM | CPRCERVTSTAD | ------------ |
| G4371 | (5) | RLQREVEELRAIKVGPPTVISPHSCEPLPASTLSM | CPRCERVSTAD | ------------ |
| CpHB17 | (14) | RLQREVEELRAMKVGPPTVISPHSCEPLPASTLTM | CPRCERVSTA | ------------ |
| VvHB17 | (13) | RLQREVEELRAMKVAPPTVISPHSCEPLPASTLTM | CPRCERVTTSLG | ------------ |
| PtHB17 | (15) | RLQREVEELRALKVGPPTVISPHSREPLPASTLTM | CPRCERVTTTG---- | VDKGSTKTT |
| RCHB17 | (17) | RLQREVEELRAMKVGPPTVSLSPHSCEPLPASTLTM | CPRCERVTTSTNTAAAFDKGPTRTA | |
| AtHAT1 | (11) | RLEKEAAELRALKLSPRLYGQMS-----PPTTLLM | CPSCERVAGP--- | -----SS |
| AtHAT2 | (10) | RLQKEAMELRTLKLSPQFYGQMT-----PPTTLIM | CPSCERVGGP--- | -----SS |
| AtHB2 | (9) | RLQKEVTELRALKLSPQFYMHMS-----PPTTLTM | CPSCEHVSVPPPQ | -----PQ |

Fig. 1F

```
ZmHB17   (6)   ----RTPRP--APAAS----PFHPRRPSAAF---
SbHB17   (12)  ----RTPRP--AAAAAAGSNPFHPRRPSAAF---
OsHOX3   (4)   ----PAVRPPPSSAAAAAPSPFHPRRPSAAF---
G4370    (7)   ----RITRP------AASPFHPRRPSAAF---
AtHB18   (8)   ----NDSNAVQEGAVLSSRSRMTISSSSSLC---
AlHB18   (18)  ----NDSNAVQEGAVLSSRSRMTISSSSSLC---
AtHB17   (2)   ----PSRAVVP--VPAKKTFPPQE-RDR------
AlHB17   (19)  ----PSRAVVP--VPAKKTFPPQE-RDH------
ThHB17   (16)  ----PYVVDGGGVLAKKTLPTQE-REH------
G3524    (3)   ----KPPSAAATLSAK-VPPTQS-RQPSAAC---
G4371    (5)   ----KPPSAAATLSAK-VPPTQS-RQPSAAC---
CpHB17   (14)  ----PTAVLDTTAK-AGPPR--QSSSAAC---
VvHB17   (13)  -KDPTNRTTSPTLSSK-LPTALHSRHSSAAC---
PtHB17   (15)  RTAVANPTIAATLSSENGAPALQSRQS---C---
RcHB17   (17)  TPATTPTTAVATLSSKVGTPTLQSRQSSAAC---
AtHAT1   (11)  SN-HNQRSVSLSPWL----QMAHGSTFDVMRPRS
AtHAT2   (10)  SNHHHNHRPVSINPWVACAGQVAHGLNFEALRPRS
AtHB2    (9)   AATSAHHRSLPVNAWAP-ATRISHGLTFDALRPRS
```

Fig. 1G

MUTATION OF THE EAR MOTIF OF CLASS II HD-ZIP POLYPEPTIDES

CROSS REFERENCE TO RELATED APPLICATIONS

This application is a continuation of Ser. No. 14/387,227, filed Sep. 22, 2014 which is a 371 National Stage application of International Application No. PCT/US13/35640, filed Apr. 8, 2013, which claims the priority of U.S. Provisional Patent Application No. 61/621,980, filed Apr. 9, 2012, all of which are incorporated herein by reference in their entireties.

FIELD OF THE INVENTION

The present disclosure relates to plant genomics and plant improvement, increasing a plant's photosynthesis and the yield.

BACKGROUND

Yield is one of the most important agronomic traits and is determined by the interaction of specific genetics within the crops with environmental factors. An important approach to increasing yield potential is increasing overall plant productivity through increasing photosynthetic efficiency or resource utilization.

The *Arabidopsis* sequence AtHB17 (At2g01430, or G1543) encodes a member of the class 11 sub-group of the homeodomain-leucine zipper protein (HD-Zip) family of transcription factors. It triggers increases in chlorophyll levels when overexpressed in plants (U.S. Pat. No. 7,511, 190).

The instant disclosure provides methods for altering the protein structure of AtHB17 and other class II HD-ZIP closely-related to AtHB17, i.e. introducing mutations to the EAR motif of the AtHB17 Glade sequences and overexpressing those EAR mutation variants in plants to confer beneficial phenotypes.

SUMMARY

The instant disclosure provides a method to reduce or eliminate certain phenotypes that may be associated with the overexpression of HD-ZIP polypeptides while maintaining the high rates of photosynthesis that can be associated with said overexpression. Certain phenotypes may be reduced or eliminated by introducing an EAR mutation variant of AtHB17 or related class II HD-ZIP polypeptides (AtHB17 clade members) into a target plant. Typically, the conserved EAR motif SEQ ID NO: 50 in the AtHB17 clade members is replaced with the mutant EAR motif, SEQ ID NO: 1 (i.e., at least one of the conserved leucines within the EAR motifs is replaced with an amino acid other than leucine, valine and isoleucine). These EAR mutant variants thus do not comprise SEQ ID NO: 50. These variants can regulate stomatal aperture of the transgenic plants in a manner similar to wild-type plants, yet retains increased chlorophyll levels and enhanced photosynthetic capacity. The combination of these properties results in increased photosynthetic rates in transgenic plants overexpressing the EAR mutation variants.

The instant disclosure provides a transgenic C3 or C4 plant that comprises a polynucleotide encoding a EAR mutation variant that comprises a mutant EAR motif of $X_1$-$X_2$-$X_3$-$X_4$-$X_5$ (set forth in SEQ ID NO: 1), where $X_1$ and $X_3$ are any amino acid other than leucine, isoleucine or valine; $X_2$ and $X_4$ are any amino acid; and $X_5$ is isoleucine, leucine or methionine. The polypeptide additionally comprises a homeodomain that shares an amino acid percentage identity to the homeodomain of any of SEQ ID NO: 2-20; and a homeobox-associated leucine zipper (HALZ) domain that shares an amino acid percentage identity to the HALZ domain of any of SEQ ID NO: 2-20. The amino acid percentage identity is selected from the group consisting of at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and about 100%.

The transgenic C3 or C4 plant overexpressing said EAR mutation variant has higher nitrogen use efficiency, lower chlorophyll levels, greater stomatal conductance, greater size, greater biomass, greater growth rate, and/or greater yield relative to a first control plant of the same species that comprises a recombinant polynucleotide encoding any of SEQ ID NO: 2-20.

In some embodiments of the disclosure, the transgenic C3 or C4 plants also have greater nitrogen use efficiency, greater size, greater biomass, greater yield, greater growth rate, greater chlorophyll levels, greater photosynthetic capacity, greater photosynthetic rate, and/or greater stomatal conductance, relative to a second control plant that is a wild type or non-transformed plant of the same species.

In some embodiments of the instant disclosure, the polypeptide is at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or about 100% identical to the full length sequence of SEQ ID NO: 2-20.

In a preferred embodiment, $X_1$ or $X_3$, or both $X_1$ and $X_3$, are alanine.

In another preferred embodiment, the EAR mutant motif is A-D-A-T-I (SEQ ID NO: 89).

The instant disclosure also provides a method for conferring to a C3 or C4 plant greater nitrogen use efficiency, greater chlorophyll levels, greater photosynthetic capacity, greater photosynthetic rate, greater stomatal conductance, greater size, greater biomass, or greater yield relative to a wild type or non-transformed plant of the same species or a plant transformed with an empty vector. The method comprises the steps of:

(a) providing a polynucleotide encoding a first polypeptide that comprises
        (1) a consensus EAR motif set forth as SEQ ID NO: 50;
        (2) a homeodomain that shares an amino acid percentage identity to a homeodomain of any of SEQ ID NO: 2-20; and (3) a homeobox-associated leucine zipper (HALZ) domain that shares an amino acid percentage identity to a HALZ domain set forth in any of SEQ ID NO: 2-20;

wherein the amino acid percentage identity is selected from the group consisting of:

at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and about 100%;

(b) mutagenizing the polynucleotide, wherein the mutagenized polynucleotide encodes a EAR mutant polypeptide comprising a mutant EAR motif of $X_1$-$X_2$-$X_3$-$X_4$-$X_5$ (set forth in SEQ ID NO: 1), where $X_1$ and $X_3$ are any amino acid other than leucine, isoleucine or valine; and $X_5$ is isoleucine, leucine or methionine;

(c) introducing the mutagenized polynucleotide into a target plant to produce a transgenic C3 or C4 plant, wherein expression of the mutagenized polynucleotide confers the improved trait in the transgenic C3 or C4 plant; and (d) optionally, selecting the transgenic C3 or C4 plant having greater nitrogen use efficiency, greater chlorophyll levels, greater photosynthetic capacity, greater photosynthetic rate, greater stomatal conductance, greater size, greater biomass, or greater yield relative to a wild type or non-transformed plant of the same species.

In another embodiment of the instant disclosure, said EAR mutant polypeptide has decreased repression activity as compared to the first HD-ZIP polypeptide which comprises the native EAR motif (SEQ ID NO: 1).

In a preferred embodiment, the first polypeptide is a sequence selected from SEQ ID NO: 2-20.

In another preferred embodiment of the instant disclosure, the transgenic plant that is generated by transforming the EAR mutant polynucleotide is a soybean or a corn plant.

BRIEF DESCRIPTION OF THE SEQUENCE LISTING AND DRAWINGS

The Sequence Listing provides exemplary polynucleotide and polypeptide sequences of the instant disclosure. The traits associated with the use of the sequences are included in the Examples. The sequence listing was created on Apr. 5, 2013 and is 101,575 bytes (99.1 kilobytes as measured in MS Windows). The entire content of the sequence listing is hereby incorporated by reference.

FIGS. 1A-1G show the alignment of the AtHB17 subclade sequences. The boxes indicate the conserved EAR motifs, the homeodomains (HD), the homeodomain-associated leucine zippers (HALZ), and the "CPSCE" domain. In each column, asterisks indicate identical amino acid residues, colons indicate conservative substitutions and periods indicate similar amino acids. SEQ ID NOs: of the respective proteins are shown in parentheses.

Figure 2B:
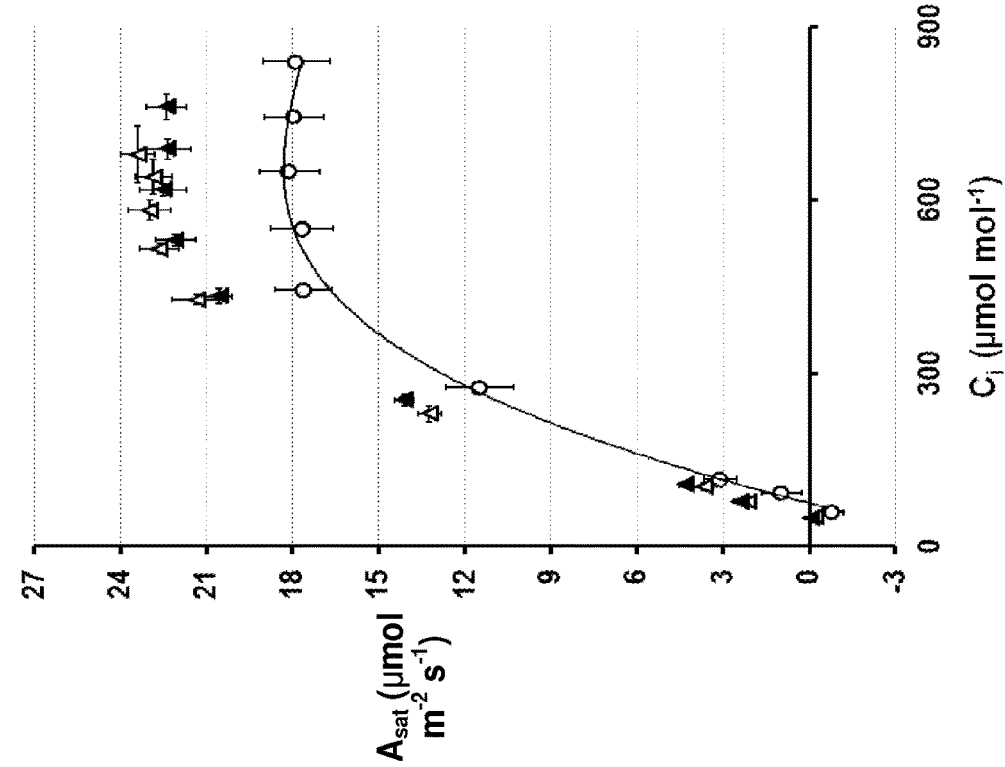

FIGS. 2A-2B show the response of light-saturated photosynthesis ($A_{sat}$) to leaf sub-stomatal $CO_2$ concentration ($C_i$) for two 35S::AtHB17 native protein lines (FIG. 2A) and two 35S::AtHB17 lines with a mutation in the EAR domain (AtHB17 L84A L86A) (FIG. 2B). All data are plotted against an empty vector control line to which a polynomial regression has been fitted. All data points are the mean±1 standard error of measurements made on leaves of at least six replicate plants.

Figure 3A:
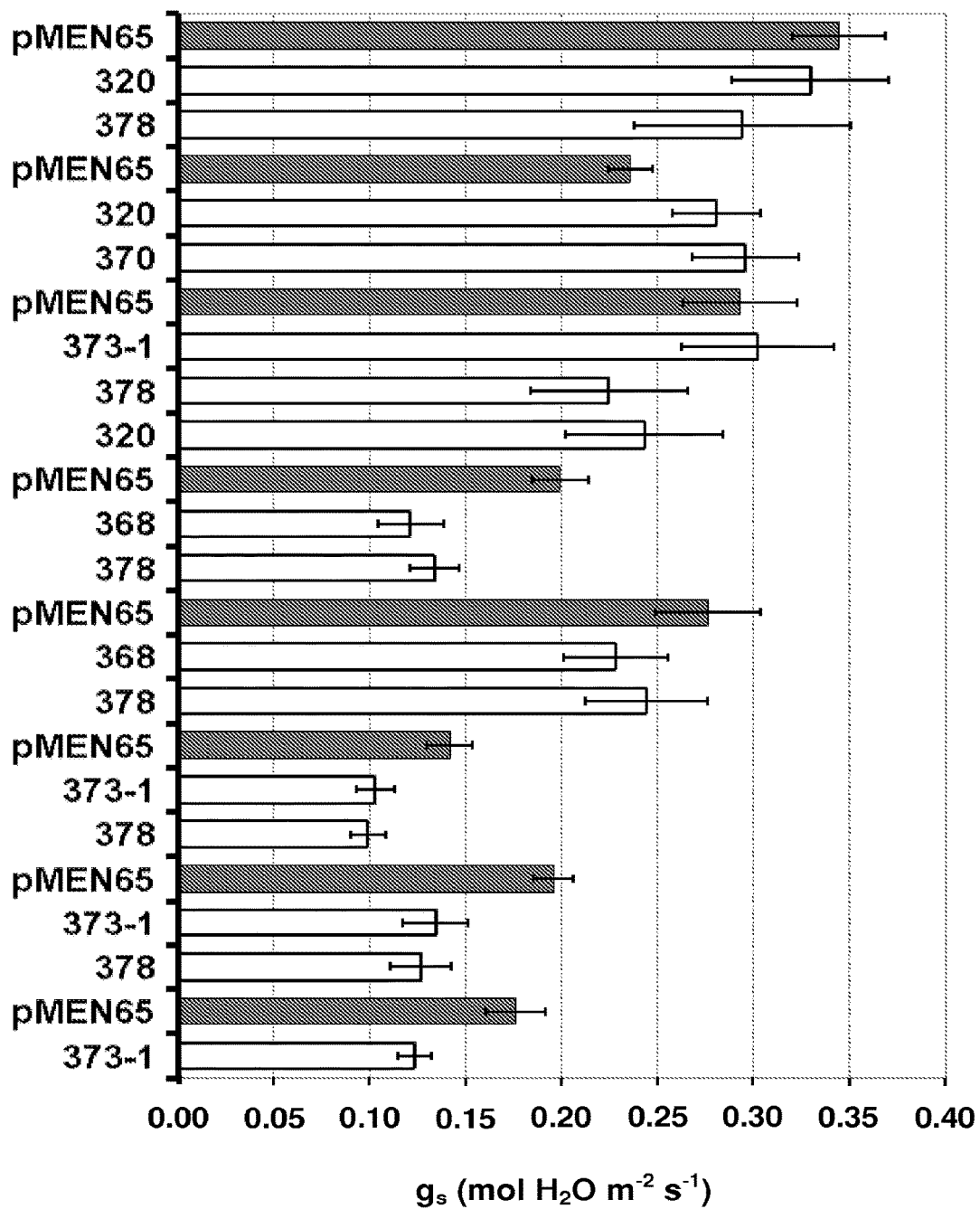
Figure 3B:
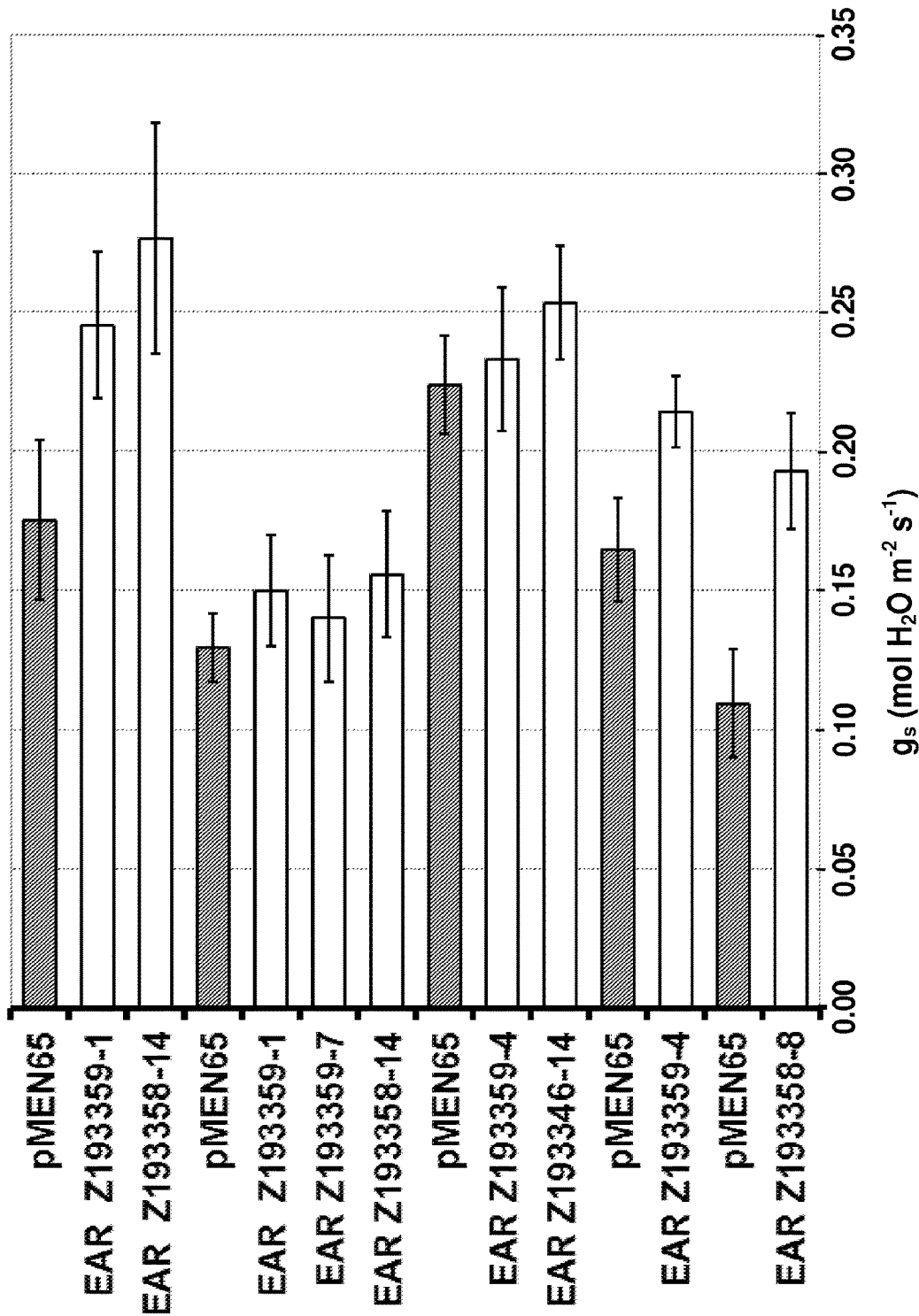

Legend for FIG. 2A and FIG. 2B:
○ represents pMEN65 lines
Δ represents 35S::AtHB17 373-22 lines
▲ represents 35S::AtHB17 378-6 lines
☐ represents EAR Z193359-1 lines
■ represents EAR 7193358-14 lines FIGS. 3A-3B show the stomatal conductance ($g_s$) measured on multiple 35S::AtHB17 native protein lines (FIG. 3A) and two 35S::AtHB17 EAR mutant lines (AtHB17 L84A L86A) (FIG. 3B) along with empty vector controls (pMEN65) in several independent experiments. For each independent experiment, the empty vector control line (solid bar) is plotted on the left of the 35S::AtHB17 or 35S::AtHB17 variant line(s) measured in the same experiment (white bars). All measurements were made at an atmospheric $CO_2$ concentration of 400 µmol mol$^{-1}$ after acclimation to a light condition that is saturating for photosynthesis (the photosynthetic photon flux is at least 700 (µmol m$^{-2}$ s$^{-1}$)). All data shown are the mean±1 standard error of measurements made on at least five replicate plants. An asterisk above a 35S::AtHB17 or AtHB17 variant bar indicates that the mean shown for that line is significantly different than the control measured at the same time (solid bar on left).

Figure 4A:
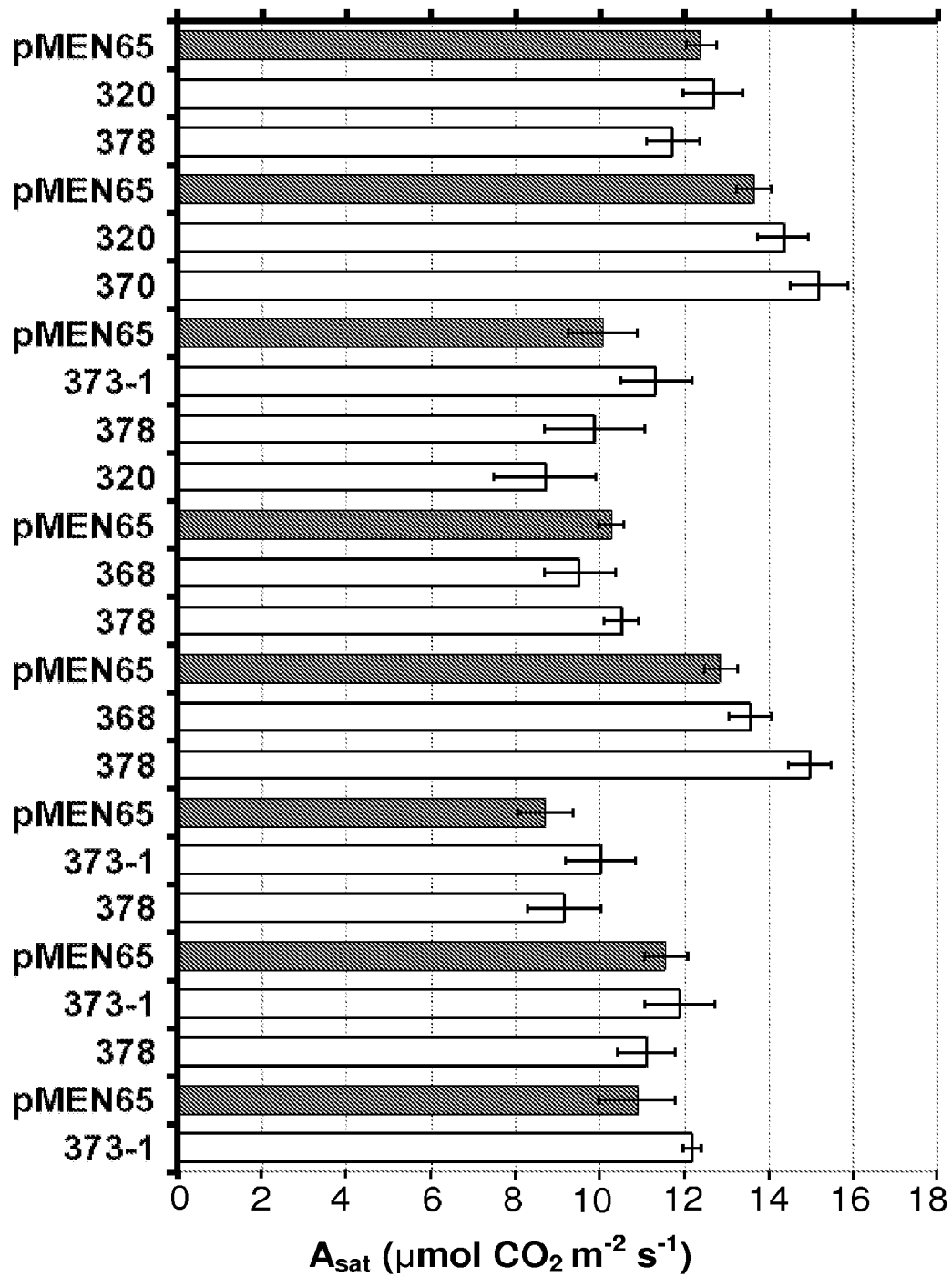
Figure 4B:
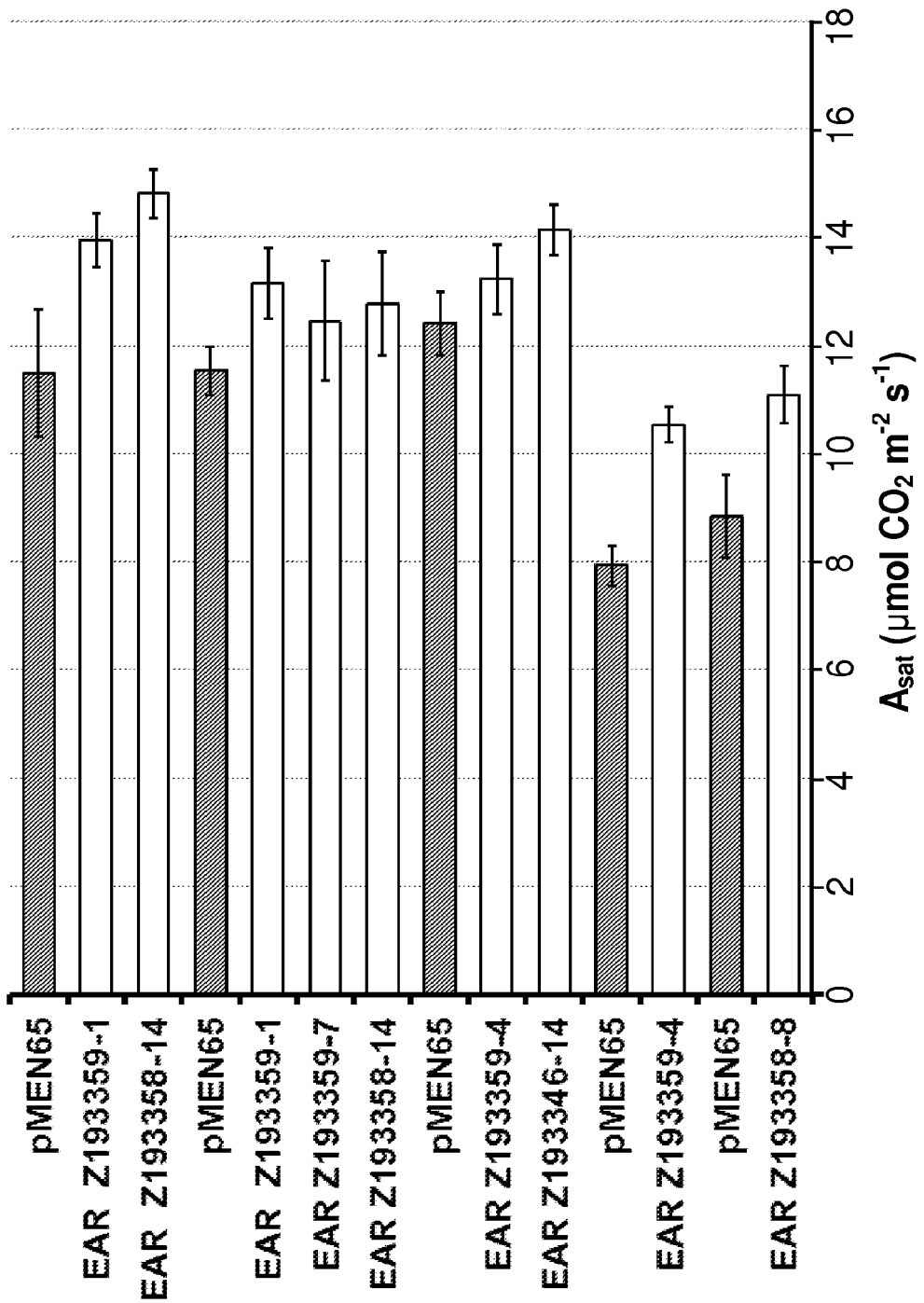

FIGS. 4A-4B shows light-saturated photosynthesis ($A_{sat}$) measured on multiple 35S::AtHB17 lines (FIG. 4A) and two 35S::AtHB17 EAR mutant lines (AtHB17 L84A L86A) (FIG. 4B) along with empty vector controls (pMEN65) for data collected after acclimation to a current atmosphere during several independent experiments. For each experiment the empty vector control line (solid bar) is plotted on the left of the 35S::AtHB17 lines measured in the same experiment (white bars). All measurements were made as described in FIG. 3. All data shown are the mean±1 standard error of measurements made on at least five replicate plants. * positioned above a 35S::AtHB17 bar indicates that the mean shown for that line is significantly different from the control measured at the same time (solid bar on left).

Figure 5B:
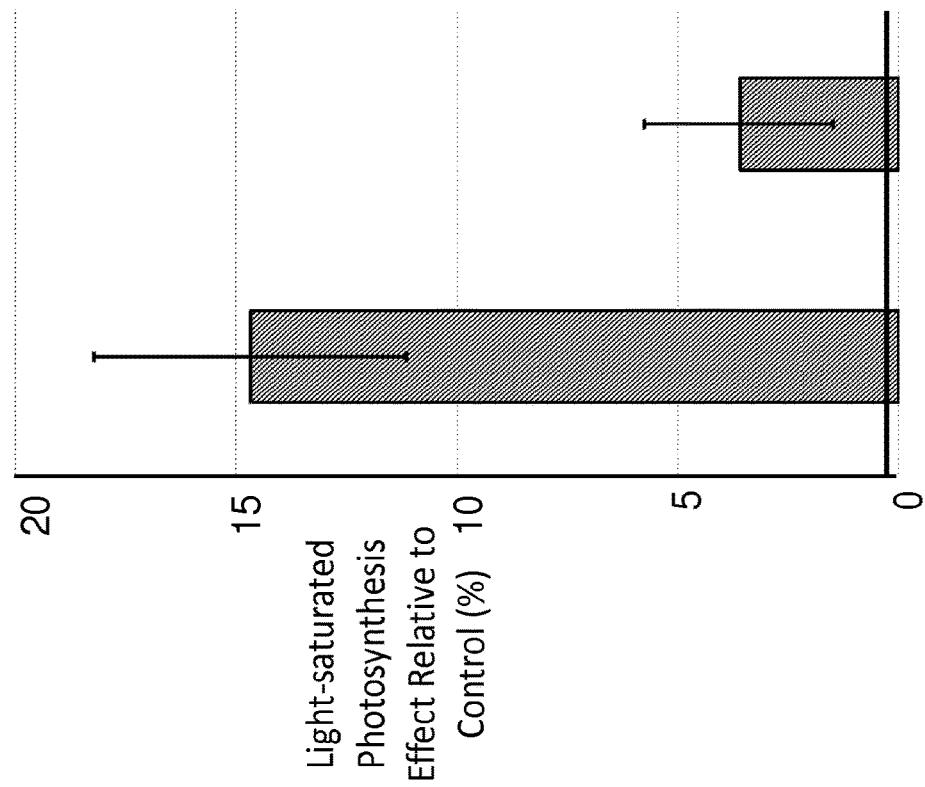
Figure 5A:
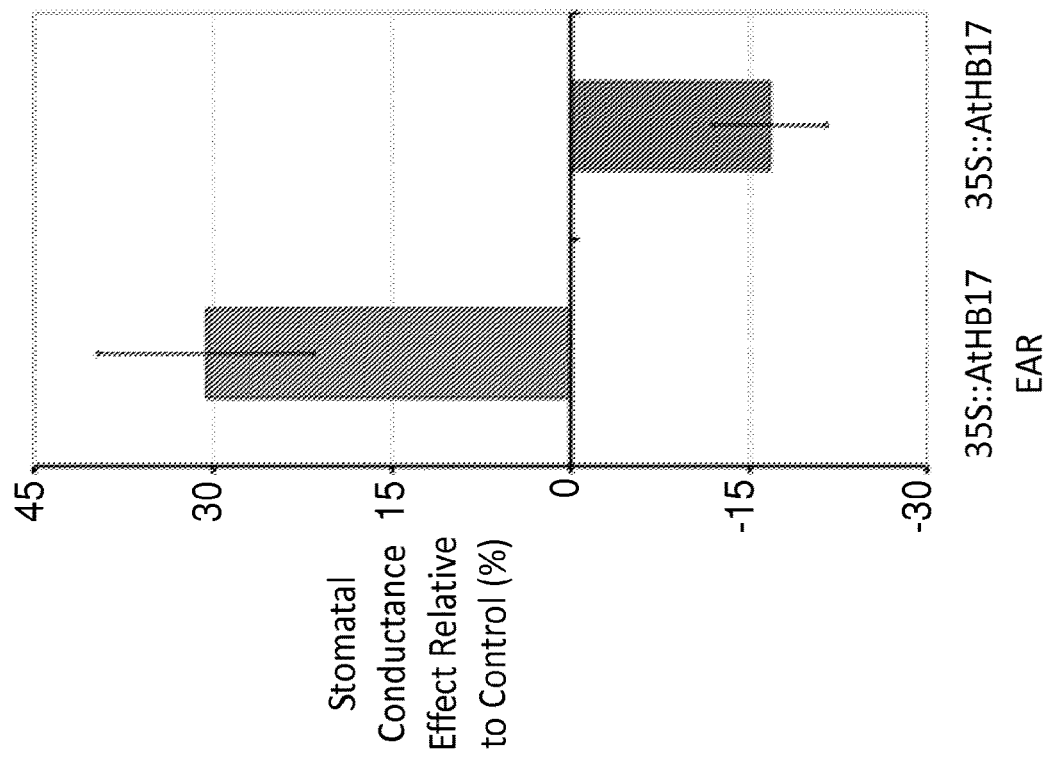

FIGS. 5A-5B shows the percentage change in stomatal conductance and light-saturated photosynthesis plotted for 35S::AtHB17 lines expressing either the native protein, or the protein with a mutation in the EAR domain, relative to a control line. Data presented is the mean and standard error of the percent effect size determined for up to four independent lines in at least six independent experiments for each protein variant.

Figure 6A:
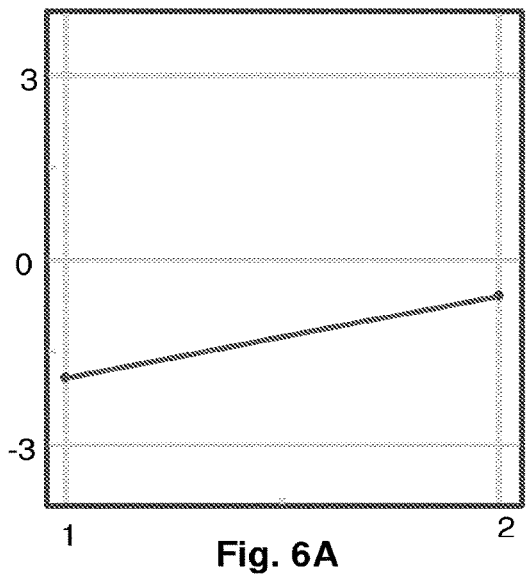
Figure 6B:
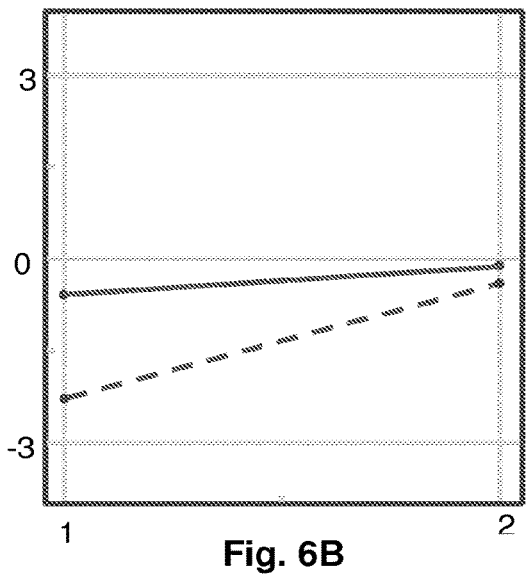
Figure 6C:
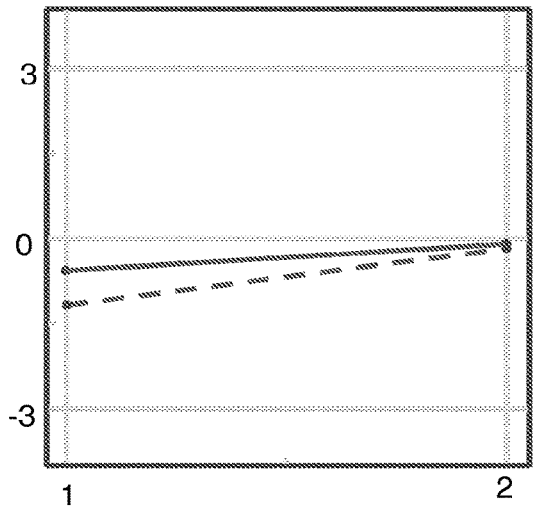
Figure 6D:
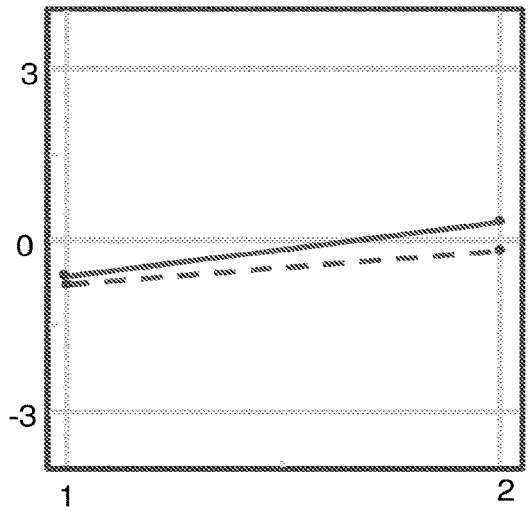

FIGS. 6A-6D shows trend plots of the expression of several genes involved in the regulation of stomatal movement, from a transcript profiling experiment comparing plants overexpressing AtHB17 (35S::AtHB17, represented in each plot by the "1" on each x-axis) and plants overexpressing an AtHB17 variant in which the EAR motif was mutated (35S::AtHB17 L84A_L86A, represented in each plot by the "2" on each x-axis) to relative to control plants. Data points are the log 2 of the ratio of intensity of a given probeset in the experimental plants vs. the controls. In FIG. 6A, the solid line represents expression of AtBGL1. In FIG. 6B, the solid line represents expression of KAT1 and the dashed line represents expression of KAT2. In FIG. 6C, the solid line represents expression of ABI1 and the dashed line represents expression of RD20. In FIG. 6D, the solid line represents expression of CPK6 and the dashed line represents expression MYB60.

Figure 7A:
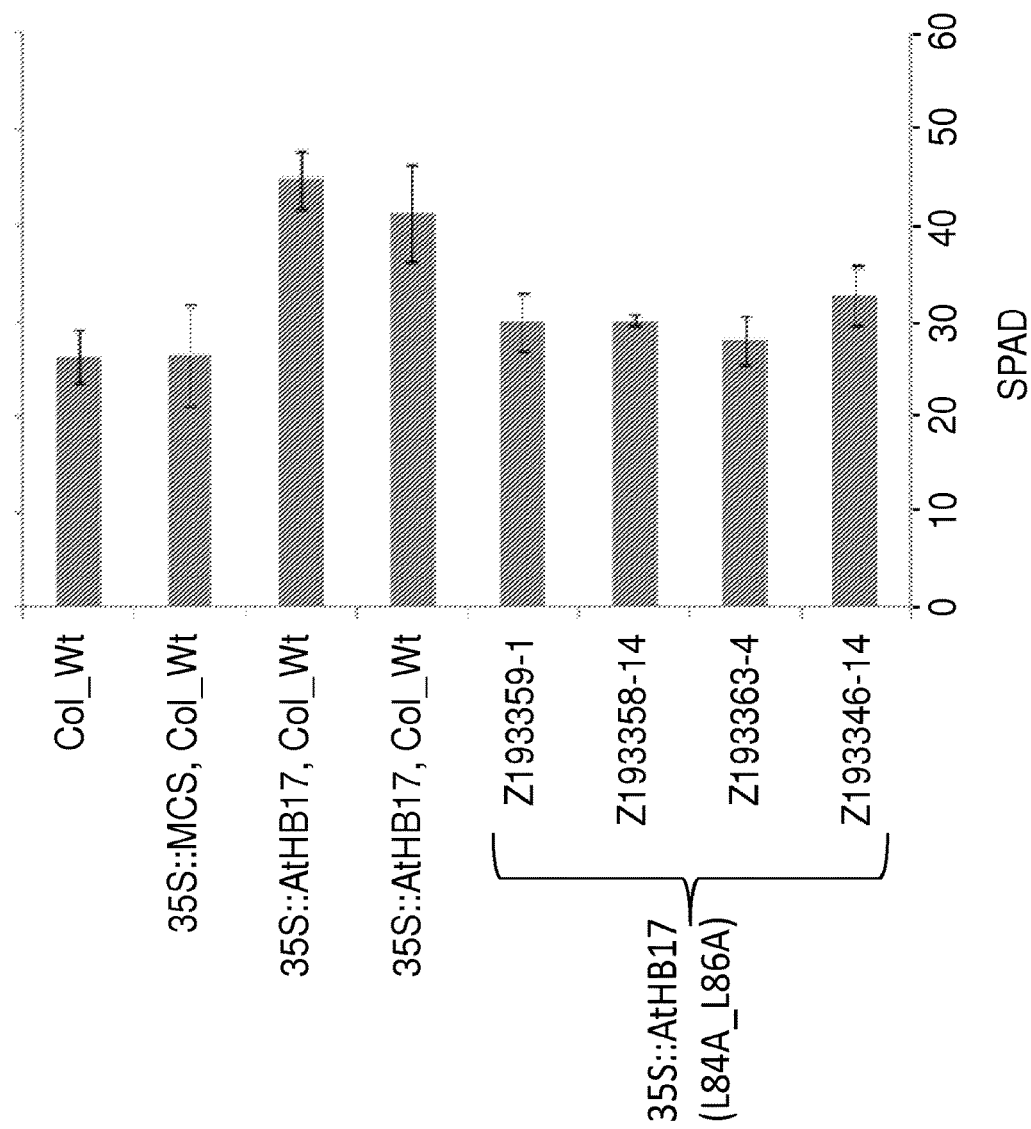
Figure 7B:
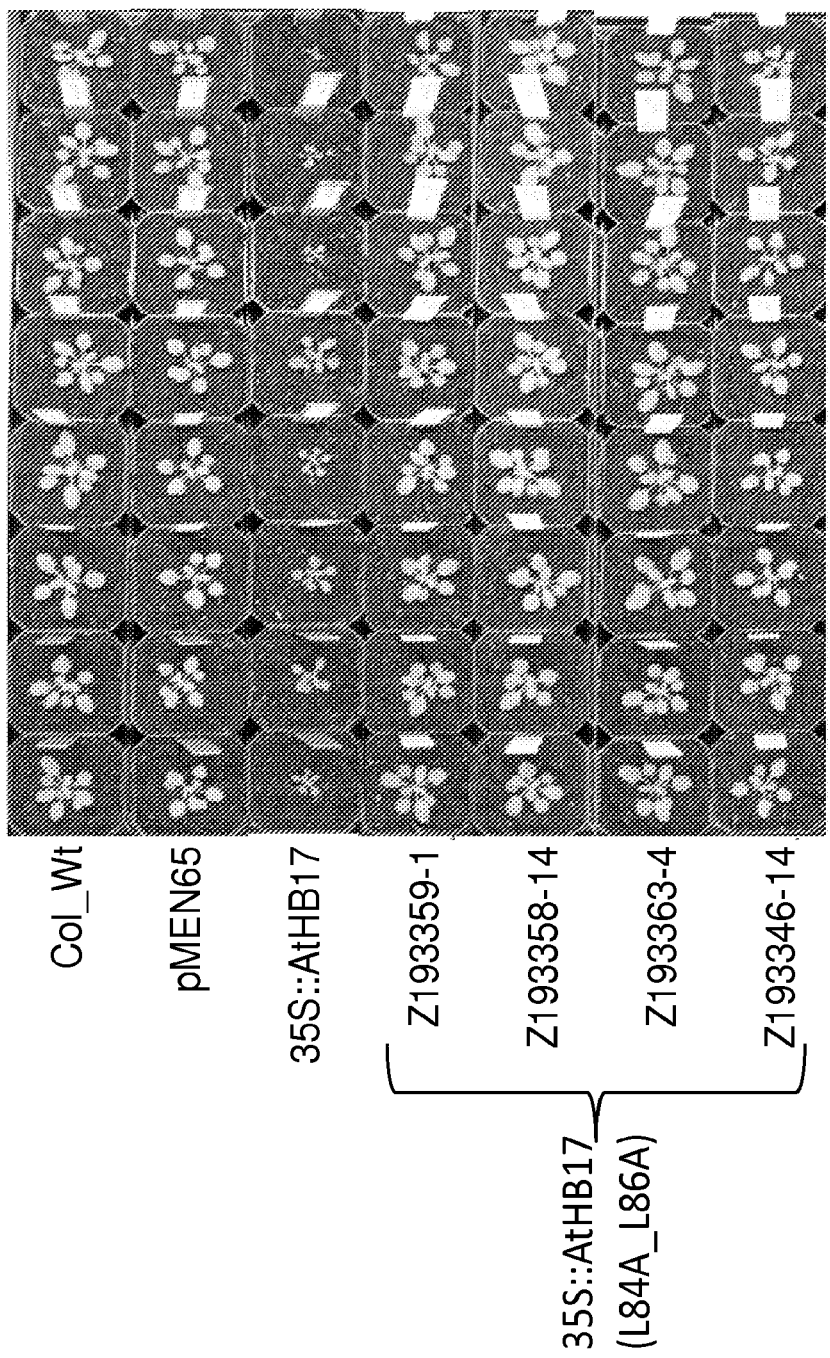

FIGS. 7A-7B show chlorophyll content as measured by a Minolta SPAD meter and morphological phenotypes of the *Arabidopsis* plants overexpressing the EAR mutant and the native AtHB17 polypeptide. FIG. 7A shows the chlorophyll levels (SPAD) of plants from an empty vector line ("35S:: MCS"), a wild type line ("Col_Wt"), a transgenic line overexpressing the native AtHB17 polypeptide ("35S:: AtHB17") and four lines of plants overexpressing EAR mutation variant ("Z193359-1", "Z193358-14", "Z193363-4", and "Z193346-14"), "35S::AtHB17 (L84A_L86A)". The EAR mutant overexpressors were larger in size and biomass compared to empty vector lines and the wild type plants, and significantly larger and had more biomass than AtHB17 overexpressors, as indicated FIG. 7B.

Figure 8:
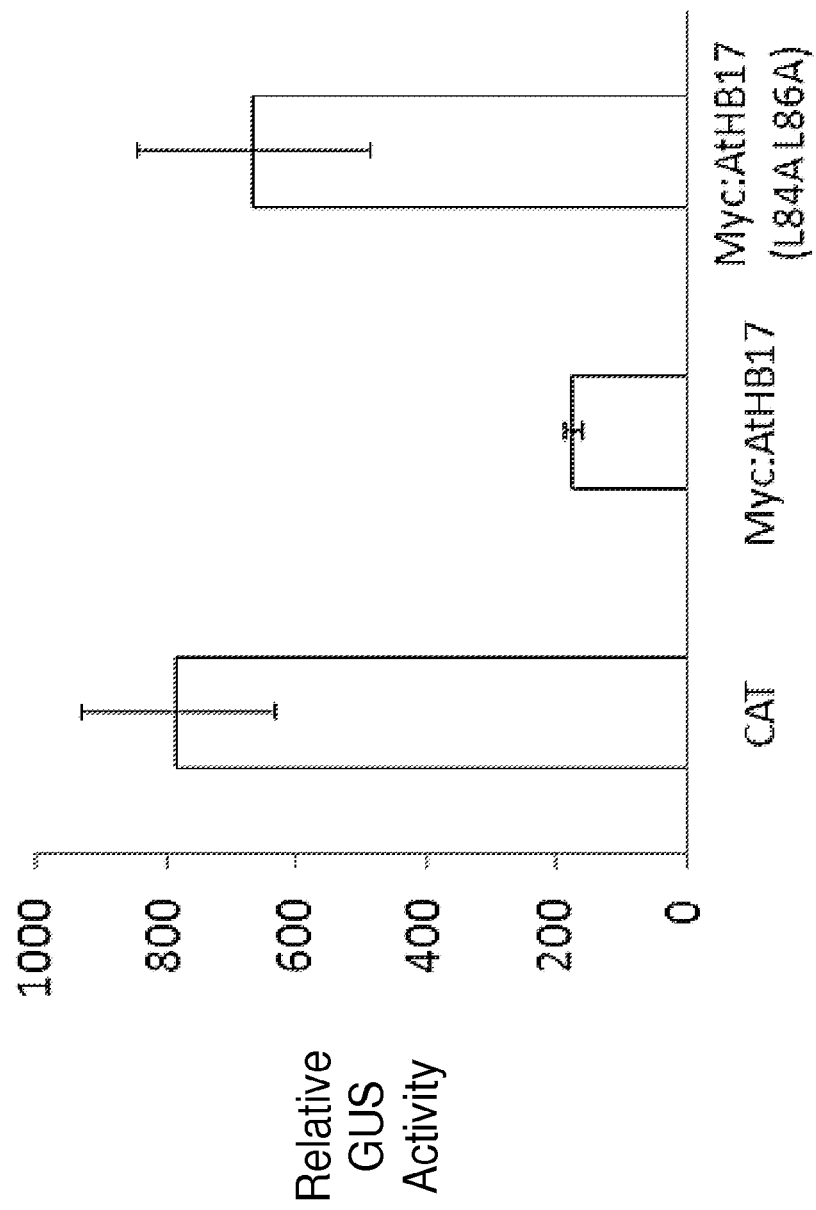

FIG. 8 shows the results of a protoplast-based transcriptional assay analyzing the effect of the EAR mutation on transcriptional repression. Chloramphenicol acetyltransferase (CAT), AtHB17, and the EAR mutant (AtHB17 L84A L86A) constructs were co-transfected into *Arabidopsis* mesophyll protoplasts with a prHAT1::GUS reporter gene. Data are mean fluorescence reading measuring GUS-mediated substrate of three replicates.

Figure 9:
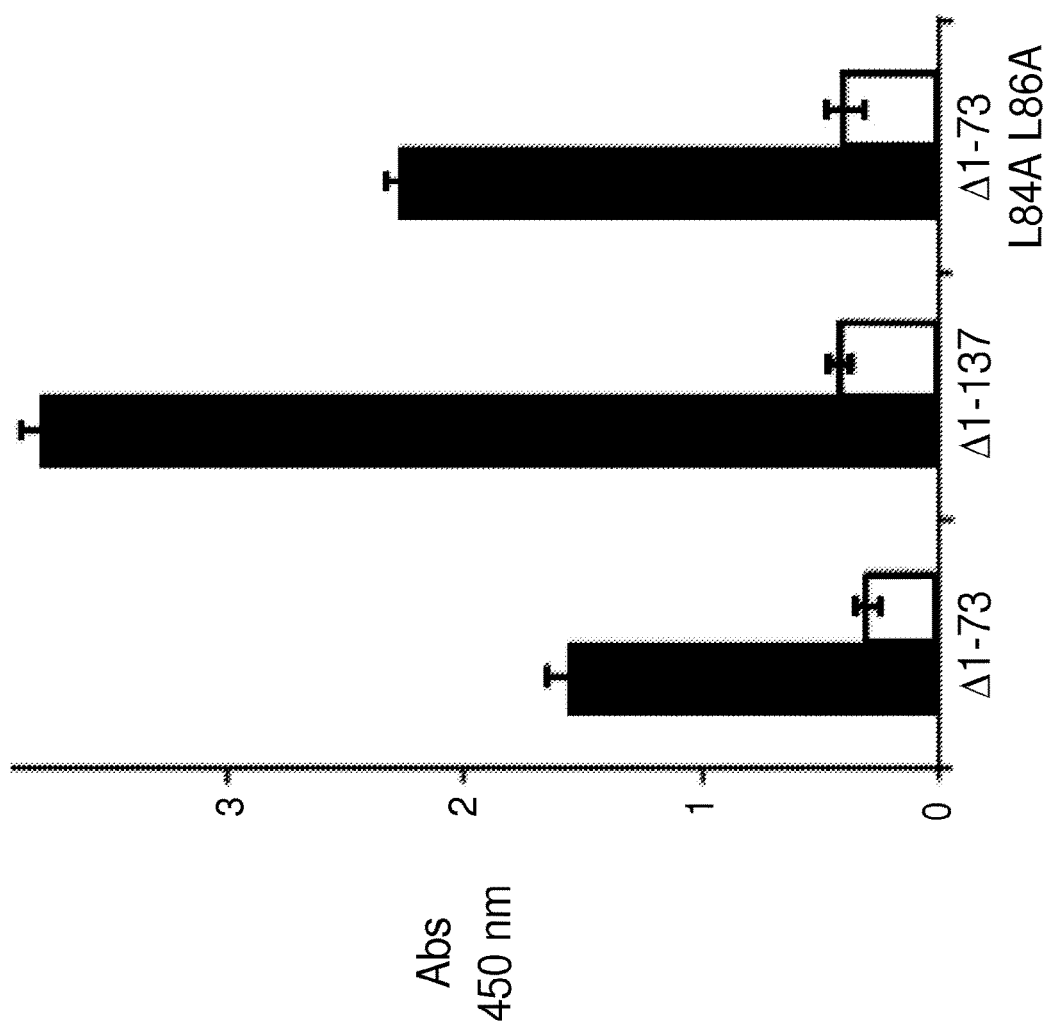

FIG. 9 shows that the EAR mutation did not impair the DNA binding activity of AtHB17. An AtHB17Δ1-73 deletion polypeptide which lacks the amino acid residues 1-73 ("Δ1-73"), an AtHB17Δ1-73 L84A L86A mutant polypeptide containing an EAR mutation in addition to a deletion of amino acid residues 1-73 ("Δ1-73 L84A L86A") were analyzed using an ELISA-based binding assay as described in the Examples. The mutant polypeptide ("Δ1-73 L84A L86A") showed higher DNA-binding activity as compared to the deletion polypeptide ("Δ1-73"). The solid bars show results obtained in AtHB17 activity assays with the unmutated HD-ZIP Class II binding site (SEQ ID NO: 48), and the white bars represent results with the mutated HD-ZIP Class II binding site (SEQ ID NO: 49).

DETAILED DESCRIPTION

The present disclosure relates to polynucleotides and polypeptides for modifying phenotypes of plants, particularly those associated with increased abiotic stress tolerance and increased yield with respect to a control plant (for example, a wild-type plant, a non-transformed plant, or a plant transformed with an "empty" nucleic acid construct or vector lacking a polynucleotide of interest comprised within a nucleic acid construct introduced into a plant). Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the instant disclosure.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

Definitions

"Polynucleotide" is a nucleic acid molecule comprising a plurality of polymerized nucleotides, e.g., at least 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a nucleic acid construct, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription Operationally, genes may be defined by the cis-trans test, a genetic test that determines whether two mutations occur in the same gene and that may be used to determine the limits of the genetically active unit (Rieger et al., 1976). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "polypeptide" is an amino acid sequence comprising a plurality of consecutive polymerized amino acid residues e.g., at least 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence. "Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIGS. 1A-1G may be used to identify conserved domains and relatedness within these domains. An alignment may suitably be determined by means of computer programs known in the art, such as MACVECTOR software (1999) (Accelrys, Inc., San Diego, Calif.), and the European Molecular Biology Open Software Suite (EMBOSS) Needle program (Rice, P., et al. 2000)

A "conserved domain" or "conserved region" as used herein refers to a region within heterogeneous polynucleotide or polypeptide sequences where there is a relatively high degree of sequence identity or homology between the distinct sequences. With respect to polynucleotides encoding presently disclosed polypeptides, a conserved domain is preferably at least nine base pairs (bp) in length. Protein sequences, including transcription factor sequences, that possess or encode for conserved domains that have a minimum percentage identity and have comparable biological activity to the present polypeptide sequences, thus being members of the same clade of transcription factor polypeptides, are encompassed by the instant disclosure. Reduced or eliminated expression of a polypeptide that comprises, for example, a conserved domain having DNA-binding, activation or nuclear localization activity, results in the transformed plant having similar improved traits as other transformed plants having reduced or eliminated expression of other members of the same clade of transcription factor polypeptides.

A fragment or domain can be referred to as outside a conserved domain, outside a consensus sequence, or outside a consensus DNA-binding site that is known to exist or that exists for a particular polypeptide class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al., 2000a, 2000b). Thus, by using alignment methods well known in the art, the conserved domains of the plant polypeptides may be determined.

The conserved domains for many of the polypeptide sequences of the present disclosure are listed in Table 1 and are indicated by amino acid coordinate start and stop sites. A comparison of the regions of these polypeptides allows one of skill in the art (see, for example, Reeves and Nissen, 1995) to identify domains or conserved domains for any of the polypeptides listed or referred to in this disclosure.

"Complementary" refers to the natural hydrogen bonding by base pairing between purines and pyrimidines. For example, the sequence A-C-G-T (5'→3') forms hydrogen bonds with its complements A-C-G-T (5'→3') or A-C-C-U (5'→3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the instant disclosure is a variant of a nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent polypeptide. Thus, it will be readily appreciated by those of skill in the art, that any of a variety of polynucleotide sequences is capable of encoding the polypeptides and homolog polypeptides of the instant disclosure. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least 9 consecutive nucleotides, preferably at least 30 nucleotides, more preferably at least 50 nucleotides, of any of the sequences provided herein. Exemplary polynucleotide fragments are the first sixty consecutive nucleotides of the polynucleotides listed in the Sequence Listing. Exemplary fragments also include fragments that comprise a region that encodes a conserved domain of a polypeptide. Exemplary fragments also include fragments that comprise a conserved domain of a polypeptide.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least 30 amino acid residues in length and more preferably at least 60 amino acid residues in length.

The instant disclosure also encompasses production of DNA sequences that encode polypeptides and derivatives, or fragments thereof, entirely by synthetic chemistry. After production, the synthetic sequence may be inserted into any of the many available nucleic acid constructs and cell systems using reagents well known in the art. Moreover, synthetic chemistry may be used to introduce mutations into a sequence encoding polypeptides or any fragment thereof.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, epidermal cells, mesophyll cells, protoplasts, and the like), and progeny of same. The class of plants that can be used in the method of the instant disclosure is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (Ku et al., 2000; and see also Tudge, 2000).

A "control plant" as used in the present disclosure refers to a plant cell, seed, plant component, plant tissue, plant organ or whole plant used to compare against transformed, transgenic or genetically modified plant for the purpose of identifying an enhanced phenotype in the transformed, transgenic or genetically modified plant. A control plant may in some cases be a transformed or transgenic plant line that comprises an empty nucleic acid construct or marker gene, but does not contain the recombinant polynucleotide of the present disclosure that is expressed in the transformed, transgenic or genetically modified plant being evaluated. In general, a control plant is a plant of the same line or variety as the transformed, transgenic or genetically modified plant being tested. A suitable control plant would include a genetically unaltered or non-transgenic plant of the parental line used to generate a transformed or transgenic plant herein.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a polypeptide's expression is altered, e.g., in that it has been knocked out, overexpressed, or ectopically expressed.

"Genetically modified" refers to a plant or plant cell that has been manipulated through, for example, transformation (as defined below) or traditional breeding methods involving crossing, genetic segregation, selection, and/or mutagenesis approaches to obtain a genotype exhibiting a trait modification of interest "Transformation" refers to the transfer of a foreign polynucleotide sequence into the genome of a host organism such as that of a plant or plant cell. Typically, the foreign genetic material has been introduced into the plant by human manipulation, but any method can be used as one of skill in the art recognizes. Examples of methods of plant transformation include *Agrobacterium*-mediated transformation (De Blaere et al., 1987) and biolistic methodology (U.S. Pat. No. 4,945,050 to Klein et al.).

A "transformed plant", which may also be referred to as a "transgenic plant" or "transformant", generally refers to a plant, a plant cell, plant tissue, seed or calli that has been through, or is derived from a plant cell that has been through, a stable or transient transformation process in which a "nucleic acid construct" that contains at least one exogenous polynucleotide sequence is introduced into the plant. The "nucleic acid construct" contains genetic material that is not found in a wild-type plant of the same species, variety or cultivar, or may contain extra copies of a native sequence under the control of its native promoter. The genetic material may include a regulatory element, a transgene (for example, a transcription factor sequence), a transgene overexpressing a protein of interest, an insertional mutagenesis event (such as by transposon or T-DNA insertional mutagenesis), an activation tagging sequence, a mutated sequence, an antisense transgene sequence, a construct containing inverted repeat sequences derived from a gene of interest to induce RNA interference, or a nucleic acid sequence designed to produce a homologous recombination event or DNA-repair based change, or a sequence modified by chimeraplasty. In some embodiments the regulatory and transcription factor sequence may be derived from the host plant, but by their incorporation into a nucleic acid construct, represent an arrangement of the polynucleotide sequences not found in a wild-type plant of the same species, variety or cultivar.

An "untransformed plant" is a plant that has not been through the transformation process. A "stably transformed" plant, plant cell or plant tissue has generally been selected and regenerated on a selection media following transformation.

A "nucleic acid construct" may comprise a polypeptide-encoding sequence operably linked (i.e., under regulatory control of) to appropriate inducible or constitutive regulatory sequences that allow for the controlled expression of polypeptide. The expression vector or cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, to produce a recombinant plant (for example, a recombinant plant cell comprising the nucleic acid construct) as well as to progeny thereof, and to in vitro systems that mimic biochemical or cellular components or processes in a cell.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transformed or transgenic plants, however.

"Trait modification" refers to a detectable difference in a characteristic in a plant with reduced or eliminated expression, or ectopic expression, of a polynucleotide or polypeptide of the present disclosure relative to a plant not doing so, such as a wild-type plant. In some cases, the trait modification can be evaluated quantitatively. For example, the trait modification can entail at least a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular polypeptide in a suspension cell is the expression levels of a set of genes in a cell knocking out or overexpressing that polypeptide compared with the expression levels of that same set of genes in a suspension cell that has normal levels of that polypeptide. The transcript profile can be presented as a list of those genes whose expression level is significantly different between the two treatments, and the difference ratios. Differences and similarities between expression levels may also be evaluated and calculated using statistical and clustering methods.

With regard to gene knockouts as used herein, the term "knockout" refers to a plant or plant cell having a disruption in at least one gene in the plant or plant cell, where the disruption results in a reduced expression (knockdown) or altered activity of the polypeptide encoded by that gene compared to a control cell. The knockout can be the result of, for example, genomic disruptions, including chemically induced gene mutations, fast neutron induced gene deletions, X-rays induced mutations, transposons, TILLING (McCallum et al., 2000), homologous recombination or DNA-repair processes, antisense constructs, sense constructs, RNA silencing constructs, RNA interference (RNAi), small interfering RNA (siRNA) or microRNA, VIGS (virus induced gene silencing) or breeding approaches to introduce naturally occurring mutant variants of a given locus. A T-DNA insertion within a gene is an example of a genotypic alteration that may abolish expression of that gene.

"Ectopic expression or altered expression" in reference to a polynucleotide indicates that the pattern of expression in, e.g., a transformed or transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the terms "ectopic expression" or "altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression of that gene in a wild-type plant, cell or tissue, at any developmental or temporal stage. Overexpression can occur when, for example, the genes encoding one or more polypeptides are under the control of a strong promoter (e.g., the cauliflower mosaic virus 35S transcription initiation region). Overexpression may also be achieved by placing a gene of interest under the control of an inducible or tissue specific promoter, or may be achieved through integration of transposons or engineered T-DNA molecules into regulatory regions of a target gene. Thus, overexpression may occur throughout a plant, in specific tissues of the plant, or in the presence or absence of particular environmental signals, depending on the promoter or overexpression approach used.

Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors typically possess a conserved DNA binding domain. The transcription factors also comprise an amino acid subsequence that forms a transcription activation domain that regulates expression of one or more abiotic stress tolerance genes in a plant when the transcription factor binds to the regulating region.

"Yield" or "plant yield" refers to increased plant growth, increased crop growth, increased biomass, and/or increased plant product production (including grain), and is dependent to some extent on temperature, plant size, organ size, planting density, light, water and nutrient availability, and how the plant copes with various stresses, such as through temperature acclimation and water or nutrient use efficiency.

"Planting density" refers to the number of plants that can be grown per acre. For crop species, planting or population density varies from a crop to a crop, from one growing region to another, and from year to year. Using corn as an example, the average prevailing density in 2000 was in the range of 20,000-25,000 plants per acre in Missouri, USA. A desirable higher population density (which is a well-known contributing factor to yield) would be at least 22,000 plants per acre, and a more desirable higher population density would be at least 28,000 plants per acre, more preferably at least 34,000 plants per acre, and most preferably at least 40,000 plants per acre. The average prevailing densities per acre of a few other examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre (Cheikh et al. (2003) U.S. Patent Application No. US20030101479). A desirable higher population density for each of these examples, as well as other valuable species of plants, would be at least 10% higher than the average prevailing density or yield.

DESCRIPTION OF THE SPECIFIC EMBODIMENTS

Polypeptides and Polynucleotides of the Disclosure

The present disclosure includes EAR mutation variants of class II HD-ZIP polypeptides related to AtHB17, and isolated or recombinant polynucleotides encoding these EAR mutation variants. Exemplary class II HD-ZIP polypeptides that can be used to generate EAR mutations are provided in the Sequence Listing; the recombinant EAR mutant polynucleotides of the instant disclosure may be incorporated in expression vectors for the purpose of producing transformed plants. Also provided are methods for modifying plant traits including nitrogen use efficiency, photosynthetic rates, stomatal conductance, and yield. These methods are based on the ability to alter the expression of HD-ZIP regulatory polypeptides that may be conserved between diverse plant species to promote certain phenotypes and alter the repression activity of the native HD-ZIP polypeptides by mutagenizing the EAR motif to reduce other phenotypes.

Identification of the Class II HD-ZIP Regulatory Polypeptides

Related conserved class II HD-ZIP regulatory molecules may be originally discovered in a model system such as *Arabidopsis* and homologous, functional molecules then discovered in other plant species.

Exemplary polynucleotides encoding the polypeptides of the instant disclosure were identified in the *Arabidopsis thaliana* GenBank database using publicly available sequence analysis programs and parameters. Sequences initially identified were then further characterized to identify sequences comprising specified sequence strings corresponding to sequence motifs present in families of known polypeptides. Further exemplary polynucleotides encoding the polypeptides of the instant disclosure were identified in the plant GenBank database using publicly available sequence analysis programs and parameters.

Additional polynucleotides of the instant disclosure were identified by screening *Arabidopsis thaliana* and/or other plant cDNA libraries with probes corresponding to known polypeptides under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

Many of the sequences in the Sequence Listing, derived from diverse plant species, have been ectopically expressed in overexpressor plants and have shown to confer similar traits to plants overexpressing AtHB17.

Structural Information for AtHB17 (G1543) and Related Class II HD-ZIP Family Polypeptides AtHB17 is a member of the class II sub-group of HD-Zip polypeptides, which is the largest group of plant homeodomain factors. Homeobox proteins are transcription factors characterized by the presence of a homeodomain, which usually is encoded by a conserved DNA stretch of 183 base pairs specifying a 61 amino acid helix-loop-helix-turn-helix region capable of binding DNA as monomers or as homo- and/or heterodimers in a sequence-specific manner (Affolter et al., 1990; Hayashi et al., 1990). The most conserved of three alpha helices, helix 3, binds directly into the major groove of the DNA (Hanes and Brent, 1989). Homeodomains are known to involve in the transcriptional regulation of key eukaryotic developmental processes (www.ncbi.nlm.nih.gov/Structure/cdd/cddsrv.cgi?ascbin=8&maxaln=10&seltype=2&uid=197696).

HD-Zip polypeptides have been implicated in mediating the response of plants to a range of environmental conditions as well as regulating several developmental processes (Arid et al., 2007). HD-Zip polypeptides have only been reported from plants (Aso et al., 1990). They contain a homeodomain linked to a leucine zipper motif, which is thought to facilitate dimerization with each other or other leucine zipper proteins and is important for the function of the polypeptides (Ruberti et al., 1991). In general, these polypeptides have been implicated in regulating developmental processes associated with the response of plants to environmental conditions (Carabelli et al., 1993; Schena et al., 1993). HD-Zip polypeptides bind as dimers to pseudopalindromic recognition sites, and this interaction is dependent on the precise spacing between the DNA binding HD domain and the dimer forming leucine zipper region (Sessa et al., 1993). Random in vitro binding site selection indicated that for HD-Zip class I proteins, the favored recognition site was composed of two 5 base pair half sites that overlap at a central position (CAAT(A/T)ATTG) (Sessa et al., 1993). HD-Zip class II proteins interact with a similar nine base pair sequence but show a preference for G/C at the central position. The central base pair preference seems to be determined by the presence of glutamine and threonine at positions 46 and 56, respectively, in the HD of class II proteins whereas class I proteins contain an alanine and a tryptophan residue (Sessa et al., 1993).

Sequences in the AtHB17 subclade within the Class II HD-Zip subfamily all comprise a putative repression domain, a homeodomain, a homeodomain associated leucine zipper (HALZ domain), and a carboxy terminal "CPSCE" domain. At the N-terminal end of the repression domain is an EAR motif LxLxl/L/M (SEQ ID NO: 50) (FIG. 1B). The EAR motif is important for conferring transcriptional repression function to domain I of the AIJX/IAA factors in the regulation of auxin response (Tiwari et al., 2004). The EAR motif shared among AtHB17 subclade sequences is closely related to the EAR motif (ERF-associated amphiphilic repression motif) found in the ATHB2 subclade within the class TI HD-ZIP subfamily (Ikeda and Ohme-Takagi, 2009; Ciarbelli et al., 2008; Kagale et al. 2010). ATHB2 and HAT2 have been previously shown to work as transcriptional repressors in vitro and in vivo (Ohgishi et al., 2001; Sawa et al., 2002; Steindler et al., 1999). AtHB17 additionally contains a unique N-terminal extension consisting of amino acids residues 1-73 (FIG. 1A). This extension is rich in cysteines of unknown function, which could suggest either DNA binding or potential sites for redox regulation. The "CPSCE" domain, which is downstream of the leucine zipper domain, refers to the five conserved amino acids Cys, Pro, Ser, Cys, Glu. In AtHB17 subclade sequences as shown in FIG. 1F, the corresponding domain comprised within AtHB17 is a "CPRCE" domain which refers to, in order, conserved Cys, Pro, Arg, Cys, and Glu amino acids. The "CPSCE" domain is reported as being responsible for redox cell state sensing (Arid et al., 2007. Trends Plant Sci. 12: 1360-1385), and the "CPRCE" domain may also possess this function.

Table 1 shows a number of AtHB17 subclade sequences and includes the SEQ ID NO: (Column 1); the species from which the sequence was derived (Column 2) and the Gene Identifier ("GID"; Column 3), the percent identity of the polypeptide in Column 1 to the full length AtHB17 polypeptide, SEQ ID NO: 2 (Column 8), as determined by European Molecular Biology Open Software Suite (EMBOSS) Needle program (Rice, P., et al. 2000) with a gap open penalty of 10.0 and a gap extension penalty of 0.5; the amino acid residue coordinates for the conserved HB domains (Homeodomain), in amino acid coordinates beginning at the n-terminus, of each of the sequences (Column 4); the SEQ ID NO of each of the IIB domains and HALZ domains (Column 5); the conserved HB domain sequences and the conserved HALZ domain sequences of the respective polypeptides (Column 6); and the percentage identity of the conserved domains in Column 6 to the conserved domains of the AtHB17 sequence, SEQ ID NO: 2 (Column 7).

TABLE 1

Conserved domains of AtHB17 subclade sequences

| Col. 1 SEQ ID NO: | Col. 2 Species from which SEQ ID NO: was derived | Col. 3 Gene ID (Gill) | Col. 4 Conserved HB domain and HALZ domain amino acid coordinates | Col. 5 Conserved HB domain and HALZ domain SEQ ID NO | Col. 6 Conserved homeodomain and HALZ domain | Col. 7 Percent ID of the conserved domains to AtHB17 homeo and HALZ domains | Col. 8 Percent ID of the full length sequence to AtHB17 full length sequence |
|---|---|---|---|---|---|---|---|
| 2 | Arabidopsis thaliana | AtHB17 (G1543) | 136-195 | 51 | Homeodomain: PPRKKLRLT REQSRLLEDS FRQNHTLNP KQKEVLAKH LMLRPRQIE VWFQNRRA RSKLKQ | 100 | 100 |
|  |  |  | 196-237 | 70 | HALZ domain: TEMECEYLK RWFGSLTEE NHRLHREVE ELRAIKVGPT TVNSA | 100 |  |
| 3 | Glycine max | G3524 | 62-121 | 52 | Homeodomain: PPRKKLRLT KEQSRLLEES FRQNHTLNP KQKESLAMQ LKLRPRQVE VWFQNRRA RSKLKQ | 88 | 46.3 |
|  |  |  | 122-162 | 71 | HALZ: TEMECEYLK RWFGSLTEQ NRRLQREVE ELRAIKVGPP TVIS | 85.7% |  |
| 4 | Oryza sativa | G3510 | 75-134 | 53 | Homeodomain HRPKKLRLS KEQSRLLEES FRLNHTLTP KQKEALAIK LKLRPRQVE | 75 78.6% | 40.7 |

TABLE 1-continued

Conserved domains of AtHB17 subclade sequences

| Col. 1 SEQ ID NO: | Col. 2 Species from which SEQ ID NO: was derived | Col. 3 Gene ID (Gill) | Col. 4 Conserved HB domain and HALZ domain amino acid coordinates | Col. 5 Conserved HB domain and HALZ domain SEQ ID NO | Col. 6 Conserved homeodomain and HALZ domain | Col. 7 Percent ID of the conserved domains to AtHB17 homeo and HALZ domains | Col. 8 Percent ID of the full length sequence to AtHB17 full length sequence |
|---|---|---|---|---|---|---|---|
| | | | | | VWFQNRRA RTKLKQ | | |
| | | | 135-175 | 72 | HALZ domain: TEMECEYLK RCFGSLTEEN RRLQREVEE LRAMRVAPP TVLS | 81 | |
| 5 | Glycine max | G4371 | 62-121 | 54 | Homeodomain: PPRKKLRLT KEQSLLLEES FRQNHTLNP KQKESLAMQ LKLRPRQVE VWFQNRRA RSKLKQ | 86.7% | 45.9 |
| | | | 122-162 | 73 | HALZ domain: TEMECEYLK RWFGSLTEQ NRRLQREVE ELRAIKVGPP TVIS | 85.7% | |
| 6 | Zea mays | G4369 | 77-136 | 55 | Homeodomain: HRAKKLRLS KEQSRLLEES FRLNHTLTP KQKEALAVK LKLRPRQVE VWFQNRRA RTKLKQ | 76.7% | 41.4 |
| | | | 137-177 | 74 | HALZ domain: TELECEYLK RCFGSLTEEN RRLQREVEE LRAMRVAPP TVLS | 76.2% | |
| 7 | Zea mays | G4370 | 76-135 | 56 | Homeodomain: HRPKKLRLS KEQSRLLEES FRLNHTLSPK QKEALAIKL KLRPRQVEV WFQNRRART KLKH | 74.2% | 39.8% |
| | | | 136-176 | 75 | HALZ domain: TEMECEYLK RCFGSLTEEN RRLQREVEE LRAMRMAPP TVLS | 76.2% | |
| 8 | Arabidopsis thaliana | G2712 | 66-125 | 57 | Homeodomain: RRRKKLRLT KEQSHLLEES FIQNHTLTPK QKKDLATFL | 73.3 | 40.1 |

TABLE 1-continued

Conserved domains of AtHB17 subclade sequences

| Col. 1 SEQ ID NO: | Col. 2 Species from which SEQ ID NO: was derived | Col. 3 Gene ID (Gill) | Col. 4 Conserved HB domain and HALZ domain amino acid coordinates | Col. 5 Conserved HB domain and HALZ domain SEQ ID NO | Col. 6 Conserved homeodomain and HALZ domain | Col. 7 Percent ID of the conserved domains to AtHB17 homeo and HALZ domains | Col. 8 Percent ID of the full length sequence to AtHB17 full length sequence |
|---|---|---|---|---|---|---|---|
| | | | | | KLSQRQVEV WFQNRRARS KLKH | | |
| | | | 126-163 | 76 | HALZ domain: TEMECEYLK RWFGSLKEQ NRRLQIEVEE LRALKPSSTS | 66.7 | |
| 9 | Arabidopsis thaliana | G400 (AtHB2) | 126-185 | 58 | Homeodomain NSRKKLRLS KDQSAILEET FKDHSTLNP KQKQALAK QLGLRARQV EVWFQNRRA RTKLKQ | 66.7% | 31.1 |
| | | | 186-226 | 77 | HALZ domain TEVDCEFLR RCCENLTEE NRRLQKEVT ELRALKLSP QFYMH | 50.0% | |
| 10 | Arabidopsis thaliana | G399 | 127-186 | 59 | Homeodomain TSRKKLRLS KDQSAFLEE TFKEHNTLN TFKEHNTLN PKQKLALAK KLNLTARQV EVWFQNRRA RTKLKQ | 65.0% | 29.2 |
| | | | 187-227 | 78 | HALZ domain: TEVDCEYLK RCVEKI; TEE NRRLQKEAM ELRTLKLSPQ FYGQ | 50.0% | |
| 11 | Arabidopsis thaliana | G398 | 132-191 | 60 | Homeodomain TCRKKLRLS KDQSAVLED PKQKLALAK KLGLTARQV EVWFQNRRA RTKLKQ | | 35.3 |
| | | | 192-232 | 79 | HALZ domain TEVDCEYI K RCVEKLTEE NRRLEKEAA ELRALKLSPR LYGQ | 64.3% | |
| 12 | Sorghum bicolor | SbHB17 | 78-137 | 61 | Homeodomain HRSKKLRLS KEQSRLLEES FRFNHTPTPK QKEALAGKL QLRPR | | 39.7% |

TABLE 1-continued

Conserved domains of AtHB17 subclade sequences

| Col. 1 SEQ ID NO: | Col. 2 Species from which SEQ ID NO: was derived | Col. 3 Gene ID (Gill) | Col. 4 Conserved HB domain and HALZ domain amino acid coordinates | Col. 5 Conserved HB domain and HALZ domain SEQ ID NO | Col. 6 Conserved homeodomain and HALZ domain | Col. 7 Percent ID of the conserved domains to AtHB17 homeo and HALZ domains | Col. 8 Percent ID of the full length sequence to AtHB17 full length sequence |
|---|---|---|---|---|---|---|---|
| | | | | | QVEVWFQN RR ARTKLKQ | | |
| | | | 138-178 | 80 | HALZ domain TELECEYLK RCFGSLTEENRR LQREVEE LRAM RVAPP TVLS | 76.2% | |
| 13 | Vitis vinifera | VvHB 17 | 74-133 | 62 | Homeodomain PPRKKLRLS KDQSRLLEE SFRQNHTLN PKQKEALAM QLKLRPRQVEV WFQNRRARS KLKQ | 81.0% | 41.9% |
| | | | 134-174 | 81 | HALZ domain TEMECEYLK RWFGSLTEQ NRRLQREVE ELRAMKVAP PTVIS | | |
| 14 | Carica papaya | CpHB I 7 | 62-121 | 63 | Homeodomain PPRKKLRLT KEQSRLLEES FRQNHTLNP KQKETLATQ LKLRPRQVE VWFQNRRA RSKLKQ | 88.3 | 46.6 |
| | | | 122-162 | 82 | HALZ domain: TEMECEYLK RWFGSLTEQ NRRLQREVE ELRAMKVGP PTVIS | 83.3% | |
| 15 | Populus trichocarpa | PtHB17 | 56-115 | 64 | Homeodomain PPRKK LRLSKEQSRL LEESFRQHHS LNPRQKEAL ALQLKLRPR QVEVWFQN RRARSKLKQ | 81.7% | 40.5% |
| | | | 116-156 | 83 | HALZ domain: TEMEC EYLKRWFGS LTEQNRRLQ REVEELRAL KVGPPTVIS | 83.3% | |
| 16 | Thellungiella halophila | ThHB17 | 60-119 | 65 | Homeodomain: PPRKKLRLT REQSRLLEDS FRQNHTLNKQP EALAKH LMLRPRQIE VWFQNRRA RSKLKQ | 98.3% | |

TABLE 1-continued

Conserved domains of AtHB17 subclade sequences

| Col. 1 SEQ ID NO: | Col. 2 Species from which SEQ ID NO: was derived | Col. 3 Gene ID (Gill) | Col. 4 Conserved HB domain and HALZ domain amino acid coordinates | Col. 5 Conserved HB domain and HALZ domain SEQ ID NO | Col. 6 Conserved homeodomain and HALZ domain | Col. 7 Percent ID of the conserved domains to AtHB17 homeo and HALZ domains | Col. 8 Percent ID of the full length sequence to AtHB17 full length sequence |
|---|---|---|---|---|---|---|---|
| | | | 120-160 | 84 | HALZ domain: TEMECEYLK RWFGSLTEQNH RLHREVE ELRTMKVGP PTVTS | 85.7% | |
| 17 | *Ricinus communis* | RcHB17 | 67-126 | 66 | Homeodomain: PPRKKLRLS KEQSRLLEES FRQHHTLNP RQKEALAM QLKLRPRQV EV WFQNRRA RSKLKQ | 83.3% | 43.6% |
| | | | 127-167 | 85 | HALZ domain: TEMECEYLK RWFGSLTEQ NRRLQREVE ELRAMKVGP PTVLS | 83.3% | |
| 18 | *Arabidopsis lyrata* | AlHB18 | 68-127 | 67 | Homeodomain: RRRKKLRLT KEQSHLLEES FIQNHTLTPK QKKDLATFL KLSSQRQVEV WFQNRRARS KLKII | 73.3 | 39.5 |
| | | | 128-163 | 86 | HALZ domain: TEMECEYLK RWFGSLKEQ6N RRLQIEVEE LRALKPSS | 66.7% | |
| 19 | *Arabidopsis lyrata* | AlHB17 | 62-121 | 68 | Homeodomain: PPRKKLRLT REQSRLLEDS FRQNHTLNP KQKEALAKH LMLRPRQIE VWFQNRRA RSKLKQ | 98.3 | 70.3 |
| | | | 122-162 | 87 | HALZ domain: TEMECEYLK RWFGSLTEQ NHRLHREVE ELRAMKVGP TTVNS | 92.9 | |

Functional Characteristics of AtHB17 Subclade Sequences

35S::AtHB17 *Arabidopsis* plants exhibited a range of phenotypes such as darker green leaves, altered leaf morphology, and increased photosynthetic capacity as compared with wild-type plants. The dark coloration indicated that the plants likely had higher chlorophyll content and photosynthetic capacity. However, these plants were often smaller than controls.

*Arabidopsis* plants transformed with a G2712 polynucleotide encoding SEQ ID NO: 8, a closely-related paralog of AtHB17, also exhibited darker green leaves and a significant reduction in plant size relative to control *Arabidopsis* plants not transformed with the G2712 polynucleotide.

Sequence Variations

It will readily be appreciated by those of skill in the art that the instant disclosure includes any of a variety of polynucleotide sequences provided in the Sequence Listing or capable of encoding polypeptides that function similarly to those provided in the Sequence Listing or Tables 1. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (that is, peptides having some degree of equivalent or similar biological activity) but differ in sequence from the sequence shown in the sequence listing due to degeneracy in the genetic code, are also within the scope of the instant disclosure.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, for example, site-directed mutagenesis, available in the art. Accordingly, any and all such variations of a sequence selected from the above table are a feature of the instant disclosure.

In addition to silent variations, other conservative variations that alter one, or a few amino acids in the encoded polypeptide, can be made without altering the function of the polypeptide. For example, substitutions, deletions and insertions introduced into the sequences provided in the Sequence Listing are also envisioned. Such sequence modifications can be engineered into a sequence by site-directed mutagenesis (for example, Smith et al, 1992) or the other methods known in the art or noted herein Amino acid substitutions are typically of single residues; insertions usually will be on the order of about from 1 to 10 amino acid residues; and deletions will range about from 1 to 30 residues. In preferred embodiments, deletions or insertions are made in adjacent pairs, for example, a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 2 when it is desired to maintain the activity of the protein. Table 2 shows amino acids which can be substituted for an amino acid in a protein and which are typically regarded as conservative substitutions.

TABLE 2

Possible conservative amino acid substitutions

| Amino Acid Residue | Conservative substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Similar substitutions are those in which at least one residue in the amino acid sequence has been removed and a different residue inserted in its place. Such substitutions generally are made in accordance with the Table 3 when it is desired to maintain the activity of the protein. Table 3 shows amino acids which can be substituted for an amino acid in a protein and which are typically regarded as structural and functional substitutions. For example, a residue in column 1 of Table 3 may be substituted with residue in column 2; in addition, a residue in column 2 of Table 3 may be substituted with the residue of column 1.

TABLE 3

Similar amino acid substitutions

| Residue | Similar substitutions |
|---|---|
| Ala | Ser; Thr; Gly; Val; Leu; Ile |
| Arg | Lys; His; Gly |
| Asn | Gln; His; Gly; Ser; Thr |
| Asp | Glu, Ser; Thr |
| Gln | Asn; Ala |
| Cys | Ser; Gly |
| Glu | Asp |
| Gly | Pro; Arg |
| His | Asn; Gln; Tyr; Phe; Lys; Arg |
| Ile | Ala; Leu; Val; Gly; Met |
| Leu | Ala; Ile; Val; Gly; Met |
| Lys | Arg; His; Gln; Gly; Pro |
| Met | Leu; Ile; Phe |

TABLE 3-continued

Similar amino acid substitutions

| Residue | Similar substitutions |
|---|---|
| Phe | Met; Leu; Tyr; Trp; His; Val; Ala |
| Ser | Thr; Gly; Asp; Ala; Val; Ile; His |
| Thr | Ser; Val; Ala; Gly |
| Trp | Tyr; Phe; His |
| Tyr | Trp; Phe; His |

The Sequence Listing provides polypeptides that have regulatory activities. Although all conservative amino acid substitutions (for example, one basic amino acid substituted for another basic amino acid) in a polypeptide will not necessarily result in the polypeptide retaining its activity, it is expected that many of these conservative mutations would result in the polypeptide retaining its activity. Most mutations, conservative or non-conservative, made to a protein but outside of a conserved domain required for function and protein activity will not affect the activity of the protein to any great extent.

The Effects of the EAR Mutation on AtHB17 Function

The class II HD-ZIP polypeptides described herein all contain EAR motifs, within which are two highly conserved leucine residues (FIG. 1B). Our experiments showed that the conserved leucine residues within the EAR motif are required for AtHB17's transcriptional repression activity in protoplasts.

To analyze the physiological relevance of the EAR mutation, nucleic acid constructs encoding AtHB17, SEQ ID NO: 2, or AtHB17 EAR mutants (i.e., AtHB17 L84A L86A, a mutant contains the L84A and L86A mutations in the EAR motif, SEQ ID NO: 1), or the chloramphenicol acetyltransferase (CAT, SEQ ID NO: 24) were co-transfected with the prHAT1::GUS reporter gene construct into Arabidopsis mesophyll cell protoplasts to analyze the repression activity. The results show in comparison to the control group (CAT), AtHB17 was able to repress GUS reporter expression, while AtHB17 EAR mutant lost that repression activity (FIG. 8). This demonstrates that mutating the conserved leucine residues within the EAR motif of AtHB17 caused a loss of repression. The effect of EAR mutations on the DNA-binding of AtHB17 was also examined We were unable obtain sufficient quantity of the full length protein AtHB17 from E. coli to perform the binding assay. However, a deletion mutant of AtHB17 which lacks amino acids 1-73 (AtHB Δ1-73) was found to express well in E. coli and also retain a significant portion of the repression activity of the AtHB17 full length polypeptide. Thus, the truncated versions of the AtHB17 and AtHB17 EAR mutation variants were used in the DNA-binding assay. FIG. 9 shows a deletion variant of AtHB17 containing the EAR domain mutations (AtHB17 Δ1-73 L84A L86A, a mutant contains the L84A and L86A mutations and lacking the N terminal amino acid residues 1-73) was able to bind to a DNA fragment containing a class II HD-ZIP specific binding site (SEQ ID NO:48) to an extent comparable to a deletion mutant AtHB17 Δ1-73 (a mutant which lacks amino acid residues 1-73 compared to the full length polypeptide, AtHB17, SEQ ID NO: 2). These results show that mutations in the EAR domain (e.g., L84A, L86A) dramatically reduce repression activity without impairing the DNA binding of AtHB17. It is very likely that the EAR mutations relieve repression of the target genes through blocking the recruitment of other co-repressors such as Groucho/Tup1 proteins (Hill K. et al., 2008 Plant J 53, 172-185; Szemenyci H. et al., 2008. Science 319, 1384-1386).

When overexpressed in Arabidopsis, AtHB17(L84A L86A) produced similar phenotypes to those produced by overexpressing AtHB17, such as increased photosynthetic capacity, higher chlorophyll content, altered leaf morphology, increased photosynthetic rates, reduced petiole length, and early flowering compared with wild-type plants. This indicates that the repression activity of the AtHB17 is not required for the enhanced photosynthetic capacity caused by AtHB17. Significantly, unlike the full length AtHB17, overexpression of AtHB17 (L84A L86A) did not result in the dwarf phenotypes (FIG. 7B) in Arabidopsis.

It is expected that mutations substituting the conserved leucines in the EAR motif of AtHB17 with any amino acid other than isoleucine and valine (which are conservative substitutes for leucine) in AtHB17 will have similar effect as the leucine to alanine substitution present in AtHB17 (L84A L86A). It is also expected that mutagenizing the leucines in the EAR motifs of other AtHB17 Clade members will have similar effect on the activities of these Clade members.

This specification describes methods to introduce mutations into the EAR motifs of the polynucleotides encoding class II HD-ZIP polypeptides that are similar to AtHB17 in structure and function. The EAR mutation variants of these class II HD-ZIP polypeptides then can be used to confer certain traits, e.g., greater nitrogen use efficiency, greater biomass, greater size, greater photosynthetic rates and greater yield in C3 or C4 plants, while reducing other phenotypes (for example, smaller plant size). This method can be used in a wide range of species including major row crops (e.g. soy, corn, cotton, canola, sugarcane, wheat, alfalfa, sugarbeet, and vegetables), forestry, and bioenergy grasses (e.g. Miscanthus or switchgrass). EAR mutant forms of class 11 HD-ZIP could also be deployed to produce increased photosynthetic capacity to species such as algae.

EXAMPLES

It is to be understood that this instant disclosure is not limited to the particular devices, machines, materials and methods described. Although particular embodiments are described, equivalent embodiments may be used to practice the instant disclosure.

The instant disclosure, now being generally described, will be more readily understood by reference to the following examples, which are included merely for purposes of illustration of certain aspects and embodiments of the present disclosure and are not intended to limit the specification or claims. It will be recognized by one of skill in the art that a polypeptide that is associated with a particular first trait may also be associated with at least one other, unrelated and inherent second trait which was not predicted by the first trait.

Example I. Producing and Cloning the EAR Mutation in AtHB17

A full-length AtHB17 clone was subject to primer-based site-directed mutagenesis, applying oligonucleotides of the sequences, 5'-CGACGGCGGCCGCAATGGCGATTTT-GCCGGAAAA-3' (SEQ ID NO: 90) and 5'-GTGCGC-CCGGGTCAACGATCACGCTCTTGCGGC-3' (SEQ ID NO: 91), according to the directions of the QuikChange site-directed mutagenesis kit (Invitrogen) to introduce a double point mutation L84A and L86A in the full length sequence. The EAR mutations were confirmed by sequencing reactions and the resulting mutant polynucleotide AtHB17 L84A L86A (SEQ ID NO: 46) was cloned into pMEN65 with native 5' and 3' AtHB17 UTRs by SalI/NotI restriction enzymes and transformed into the wild-type Columbia ecotype of *Arabidopsis thaliana*.

Example II. Transformation of the EAR Mutant Polynucleotide Sequences

*Arabidopsis* plants were transformed by the floral dip method (Clough and Bent, 1998) using *Agrobacterium* carrying a transformation construct which contained a kanamycin resistance selectable marker system driven by the NOS promoter and the AtHB17 clone downstream from the CaMV 35S promoter. In all experiments, a control line generated by transforming Col-0 with the empty transformation construct lacking the AtHB17 clone was used to determine the effect of AtHB17 overexpression. Between twenty and forty independent primary transformants were isolated on selection media. Transformants were PCR-genotyped to confirm that they harbored the correct transgene. Expression of AtHB17 mRNA transcripts was verified by RT-PCR on RNA extracted from leaves of 40 day old plants. Lines that showed substantial levels of overexpression versus the control line were selected and used in subsequent experiments.

Example III. Protoplast-Based Transcriptional Repression Assays Protoplast Transfection

*Arabidopsis* protoplasts were isolated and transfected as previously described (Tiwari et al. 2006). Protoplasts were prepared from whole leaves of 3-4 weeks old *Arabidopsis* plants using an enzyme solution containing cellulose (Research Products International Corp) and macerozyme (SERA Electrophoresis GmbH) to remove cell walls. Plasmid DNA for transfection was prepared using Qiagen EndoFree Plasmid maxi kits. DNA was introduced by incubating protoplasts with 40% PEG for 30 minutes. Following removal of PEG, protoplasts were kept in the dark at room temperature for 18-20 hours.

Reporter Activity Assay

To assess the repression activity of the variants, 200 µl of protoplast cells were transfected with 10 µg of plasmid DNA of the GUS reporter construct with 5 µg of plasmid DNA of effector protein constructs, including the EAR mutants and native AtHB17. A 35S::CAT construct was used as a negative control. Following overnight incubation, cells were lysed in 1× cell culture lysis buffer (Promega) and incubated with 1 mM MUG (GBT) solution at 37° C. for 1 hour. GUS activity was quantified by taking fluorescence measurements using a Synergy HT Microplate Reader (BioTek). Three biological replicated were performed and GUS measurements for each construct were averaged.

In Vitro DNA-Binding Assay

To determine the effects of EAR mutation on the DNA-binding activity of AtHB17, DNA binding assays were performed in a 96-well plate-based format using the NoShift Transcription Factor Assay kit according to the manufacturer's protocol (Novagen). Duplex DNA was prepared by annealing sense and antisense 3'-biotin-TEG oligonucleotides in 0.5×SSC at a final concentration of 10 pmol/µL. Protein-DNA interactions were assayed in vitro using 10 ng recombinant protein (from soluble lysate) in 1× NoShift Binding Buffer, 0.01 U poly(dI-dC)-poly(dI-dC), 25 µg salmon sperm DNA and 10 pmol of duplex DNA in a final volume of 20 µL. The protein-DNA complex was allowed to form by incubation on ice for 30 min. The protein-DNA complex was then diluted five-fold with 1× NoShift binding buffer and added to a streptavidin-coated plate, which was incubated for one hour at 37° C. After the binding incubation, the plate was incubated with primary antibody, either α-Penta-His HRP-conjugated antibody (1:1000, Qiagen) or the AtHB17 polyclonal antibody (1:1000, Monsanto) for one hour at 37° C. For the AtHB17 polyclonal antibody, incubation with HRP-conjugated secondary goat anti-rabbit antibody (1:10000, Thermo Scientific) for one hour at 37° C. was required. A series of washes with gentle agitation followed each incubation step. To develop colorimetric signal, 1-Step Ultra TMB-ELISA (3,3,5,5 tetramethylbenzidine) (Thermo Scientific) was added to the plate wells and incubated for 15 min. Hydrochloric acid was added to stop the reaction and to provide greater sensitivity. Binding was then quantified by measurement of the absorbance at 450 nm using a Synergy HT Microplate Reader (Bio-Tek).

The DNA-binding elements used for this set of AtHB17 activity assays are summarized below (consensus binding sites are underlined):

```
CAGACAATCATTGCGGC           (SEQ ID NO: 48) =
HD-ZIP Class II consensus (1 repeat)

CAGATCAGTCTGACGGC           SEQ ID NO: 49) =
Mutated HD-ZIP Class II consensus (1 repeat)
```

Example III. *Arabidopsis* Plant Growth Conditions and Photosynthesis-Related Physiological Assays Seeds of AtHB17 lines, AtHB17 EAR mutant lines, and empty vector controls (pMEN65) were chlorine gas sterilized and sown onto plates with 80% MS+1% sucrose media. Plates were stratified in the dark at 4° C. for 3 days, then moved to a growth chamber (ATC 26, Controlled Environments Ltd, Winnipeg, Manitoba, Canada) operating a 10 hour photoperiod at a photosynthetic photon flux (PPF) of ca. 150 µmol m-2 s-1 at plant height, and a 22° C. day/19° C. night, air temperature (Tair). After seven days, seedlings were transplanted into autoclaved ProMix soil in plastic pots and returned to the same growth chamber. To minimize problems associated with small gradients in environmental conditions within the chamber, plants from different lines being compared in a given experiment were mixed within flats, and flat positions were rotated weekly within, the growth chamber. All flats were bottom watered three times a week, once with water containing a Peter's fertilizer solution (20-20-20 NPK; 0.8 g/L).

Leaf Photosynthesis-Related Physiological Analysis

After 35 days growth in the conditions described above, photosynthetic capacity, photosynthetic rate and stomatal conductance were measured. These measurements were determined from measurements of leaf $CO_2$ uptake and $H_2O$ loss made using an infra-red gas analyzer (L1-6400 XT, Licor Inc, Lincoln, Nebr., USA). All measurements were made after 40-50 min acclimation of whole *Arabidopsis* rosettes to a photosynthetic—photon flux (PPF) of 700 µmol $m^{-2}$ $s^{-2}$, under LED light banks emitting visible light (SL3500 Warm White 400-700 nm, Photon Systems Instruments, Brno, Czech Republic). The protocol of Long and Bernacchi (2003) served as a reference for creating plots of light-saturated photosynthesis ($A_{sat}$) and the rate of linear electron transport through photosystem two ($J_{PSII}$), to substomatal [$CO_2$] ($C_i$). Simultaneous measurements of light-saturated leaf $CO_2$ uptake, $H_2O$ loss and yields of chl a fluorescence measurements were made over a range of [$CO_2$] from 50 to 1000 μmol $CO_2$ $mol^{-1}$. Measurements were made at the growth air temperature of 22° C. and a leaf-air water vapor pressure deficit of ca. 0.8 kPa. The curve-fitting software of Sharkey et al. (2007) was used to make in vivo estimates of: the maximum rate of RuBP-saturated photosynthesis ($V_{c,max}$), and the light-saturated capacity for RuBP regeneration, calculated and expressed in terms of electron flow required to support the modeled rate of $A_{sat}$ ($J_{max}$). Estimates of linear electron flow through photosystem II ($J_{PSII}$) were estimated as the product of the operating efficiency of PSII ($F'_q/F'_m$) and the fraction of incident PAR absorbed by PSII (Genty et al., 1989). The fraction of the 700 μmol $m^{-2}$ $s^{-1}$ of photosynthetically active radiation (PAR) incident upon the leaf transmitted through the leaves, was measured by placing the center of the abaxial side of the leaf upon a quantum sensor (LI 190, Licor Inc.). Both the leaf and the quantum sensor were then pressed up against the upper gasket under the light source, so that transmission of the PAR from the light source was measured. No measure of reflectance from the adaxial leaf surface was made; consequently, absorption was calculated as 1 minus transmission for the determination of $J_{PSII}$. In common with most studies, we assumed that 50% of incident PAR was absorbed by PSII for the purposes of calculating $J_{PSII}$. A second estimate of PAR transmission through the leaf was made immediately after the high-light measurement using a SPAD meter (SPAD 502, Konica Minolta Sensing Inc, Japan). Two SPAD measurements were made per leaf, each approximately half way along the leaf, on either side of the mid rib.

Example IV. Nitrogen Use Efficiency Assays

*Arabidopsis* Plant Material and Growth Conditions

Seeds were surface sterilized using chlorine gas, plated on selective media, and stratified for three days at 4° C. in the dark. Plates were incubated at 22° C. under a light intensity of approximately 100 μmole $m^{-2}$ $sec^{-1}$ for seven days. Seedlings were transplanted into square pots (60 mm×60 mm) containing fritted clay topped with a small (10 mm) layer of medium particle sized sand and kept covered with a plastic dome for another seven days to maintain humidity while they became established. Plants were grown on soil under fluorescent lights, at a light intensity of approximately 100 μmole $m^{-2}$ $sec^{-1}$ and a temperature of 22° C. (L:D 10:24). Plants were cultivated under low N (2 mM nitrate) or high N (10 mM nitrate) conditions. Phosphate (0.25 mM), sulphate (0.25 mM), magnesium (0.25 mM), and sodium (0.20 mM) were present in both solutions at the same concentration. The only other differences between low and high N solutions were in potassium (5.25 mM and 2.75 mM in high and low N solutions, respectively), calcium (2.50 mM and 0.50 mM, respectively), and chloride ions (0.25 mM and 0.70 mM, respectively). Pots were watered three times daily every eight h using a commercial ebb and flow hydroponic system (Bigfoot, American Hydroponics, Arcata Calif.).

$^{15}$N Labeling and Harvest $^{15}$N uptake was estimated 32 days after sowing when plants were still vegetative. The unlabelled watering solution was replaced by an $^{15}$N-containing solution that had the same nutrient composition except that $^{14}NO_3$ was replaced by $^{15}NO_3$ at 2.5% enrichment (Chardon et al., 2010; Lemaitre et al., 2008). All pots were watered for 24 h by immersing the base of the pot with a volume of labeled solutions sufficient to cover the lower 35 mm of the pot. After 24 h, the rosette was separated from its root to stop $^{15}$N uptake. Rosettes were then dried and their dry weight was determined. Four to six replicates were harvested for uptake and remobilization experiments.

Determination of Total Nitrogen Content and $^{15}$N Abundance

After drying and weighing each sample, material was ground in a bead mill to obtain a homogenous fine powder. A subsample of 2 to 3 mg was carefully weighed into tin capsules to determine the total N content and $^{15}$N abundance at the Stable Isotope Facility at UC Davis. Samples were analyzed for $^{15}$N isotopes using a PDZ Europa ANCA-GSL elemental analyzer interfaced to a PDZ Europa 20-20 isotope ratio mass spectrometer (Sercon Ltd., Cheshire, UK). Samples were combusted at 1000° C. in a reactor packed with chromium oxide and silvered cobaltous/cobaltic oxide. Following combustion, oxides were removed in a reduction reactor (reduced copper at 650° C.). The helium carrier then flowed through a water trap (magnesium perchlorate). $N_2$ and $CO_2$ were resolved on a Carbosieve GC column (65° C., 65 mL/min) before entering the IRMS. During analysis, samples were interspersed with several replicates of at least two different laboratory standards. These laboratory standards (selected to be compositionally similar to the samples being analyzed) were previously calibrated against NIST Standard Reference Materials (IAEA-N1, IAEA-N2, IAEA-N3, USGS-40, and USGS-41). A sample's preliminary isotope ratio is measured relative to reference gases analyzed with each sample. These preliminary values are finalized by correcting the values for the entire batch based on the known values of the included laboratory standards.

The $^{15}$N abundance was calculated as atom percent (A %=($^{15}$N)/($^{15}$N+$^{14}$N)) and for unlabelled plant controls (A $%_{control}$) was 0.3660. The $^{15}$N enrichment (E %) of the plant material was then defined as E %=A $%_{sample}$–A $%_{control}$ (Chardon et al., 2010; Lemaitre et al., 2008).

NUE was determined using the ratio of rosette biomass to N concentration in the rosette (termed "usage index"; Good, Shrawat and Muench, 2004). By calculating NUE in this manner the absolute amount of biomass produced as well as the ratio of biomass per unit nitrogen was factored in. The efficiency by which N was taken up and transported to rosette leaves relative to the rosette biomass was estimated by calculating the amount of $^{15}$N in the tissue. Multiplication by 100 converts the units to micrograms. The amount of $^{15}$N per plant was determined by multiplying the NupE by tissue dry weight.

NUE (as calculated by determining the Usage Index (UI))
NUE=Usage index (UI)=DM/N %
N uptake efficiency (NupE)
NupE=$^{15}$N/DM=E %×N %×100
$^{15}$N/plant
$^{15}$N/plant=E %×N %×DM×100
DM=Dry matter Example V. Benefits of Overexpressing an EAR Mutation Variant of AtHB17 in *Arabidopsis*

Enhanced Photosynthetic Rate and Photosynthetic Chlorophyll Use Efficiency

The EAR mutation variant of AtHB17 demonstrated the ability to increase photosynthetic capacity and increase photosynthetic rates when overexpressed in *Arabidopsis* plants compared to control plants. In one of the experiments, two transgenic lines overexpressing the EAR mutation variant (AtHB17 L84A L86A), two lines overexpressing the native AtHB17, and control plants comprising the vector pMEN65, were analyzed for chlorophyll content and photosynthesis (FIG. 2 and Table 4). Both EAR mutation variant lines had higher SPAD values compared to empty vector controls but lower SPAD values when compared to native AtHB17 overexpressors, indicating that they possessed intermediate chlorophyll content levels between the empty vector control plants and the native AtHB17 overexpressors (Table 4). Although these EAR mutation variant overexpressors had lower chlorophyll content compared to native AtHB17 overexpressors, they did maintain the positive benefits of AtHB17 overexpression by having higher light-saturated photosynthetic rates relative to the empty vector control plants (FIG. 2), indicating a more optimal investment of chlorophyll content with respect to the rate of photosynthesis. These findings indicate that possible dwarfing effects resulted from constitutive AtHB17 overexpression in some species may be avoided while still retaining other phenotypes such as elevated photosynthesis by expression of a protein variant of AtHB17 with a mutated EAR domain, or a similar variant of a homologous protein.

Reduced Transcriptional Effect on Genes Involved in Stomatal Development and Function Relative to the Native AtHB17

Plants overexpressing the EAR mutation variant (AtHB17 L84A L86A) showed reduced effects on gene transcription when compared to plants overexpressing the native AtHB17 polypeptide. Overexpression of the full length native form AtHB17 has a broad effect on gene expression. In contrast, the transcriptional effects observed in lines overexpressing an EAR mutation variant of AtHB17 were dramatically reduced. Consequently, relatively few pathways were significantly perturbed in lines overexpressing EAR mutation variants than in the 35S::AtHB17 lines. These findings are consistent with the EAR mutation resulting in a loss of repression activity. In particular, the transcriptional effects on a number of genes involved in the development of stomata or regulation of stomatal function were either diminished or lost in EAR variant lines, suggestive of differential effects on stomatal function and related processes such as photosynthesis. For example, the expression

TABLE 4

The fraction of incident PPF transmitted through the leaf (Transmission), and estimate of chlorophyll content (SPAD), the $CO_2$ and light-saturated rate of photosynthesis ($A_{max}$), the light-saturated rate of photosynthesis measured at an atmospheric $[CO_2]$ of 400 μmol mol$^{-1}$ ($A_{sat\ 400}$), the $CO_2$ and light-saturated rate of linear electron flow though PSII ($J_{PSII\ max}$) and an estimate of the maximum capacity for linear electron flow contributing to RuBP regeneration ($J_{max}$) for 35S::AtHB17 protein variants and controls.

|  | Transmission | SPAD | $A_{max}$ | $A_{sat(400)}$ | JPSII | $J_{max}$ |
|---|---|---|---|---|---|---|
| pMEN65 | 0.09 (0.004) | 30.02 (1.10) | 18.09 (1.04) | 11.48 (1.17) | 104.5 (2.0) | 95.1 (4.0) |
| 35S::AtHB17 373-22 | 0.033 (0.005)* | 50.79 (1.05)* | 23.39 (0.58)* | 14.11 (0.33)* | 134.5 (3.5)* | 120.9 (5.9)* |
| 35S::AtHB17 378-6 | 0.055 (0.00)* | 37.92 (1.15)* | 22.38 (0.70)* | 13.93 (0.49)* | 125.9 (3.9)* | 1118 (4.4)* |
| EAR Z193359-14 | 0.070 (0.004)* | 33.74 (0.42)* | 20.25 (0.69)* | 14.80 (0.46)* | 116.1 (2.8)* | 112.2 (4.2)* |
| EAR Z193358-14 | 0.072 (0.002)* | 33.61 (0.99)* | 22.09 (0.56)* | 14.39 (0.58)* | 119.5 (2.8)* | 109.9 (2.4)* |

Note:
All data are the mean ± 1 standard error of measurements made on leaves of at least six replicate plants. The presence of an asterisk signifies that the mean for a given line is significantly different from the pMEN65 control ($p < 0.05$).

Increased Photosynthetic Capacity and Increased Stomatal Conductance Resulted in Increased Photosynthetic Rate Stomata regulate the exchange of $CO_2$ and $H_2O$, between the leaf and the atmosphere. Current understanding of stomatal physiology predicts that leaves with higher photosynthetic capacity would have higher stomatal conductance under optimal conditions. A mechanism for indirect sensing of photosynthetic capacity underlies this relationship, with the result that stomata respond to maintain the $CO_2$ concentration inside the leaf within a narrow range. Consequently plants with increased photosynthetic capacity would be expected to have higher stomatal conductance. Plants overexpressing the EAR mutation variant (AtHB17 L84A L86A) supported this theory (FIGS. 2 and 3). Results from at least five independent experiments showed stomatal conductance of 35S::AtHB17 EAR mutant lines was never lower, and typically higher, than for controls (FIGS. 3 and 4). The result was that increased photosynthetic capacity was realized as an increased photosynthetic rate at current atmospheric $CO_2$ concentrations in the EAR variant lines (FIG. 5). In contrast, in Arabidopsis lines constitutively overexpressing the native protein, stomatal conductance is typically lower than controls (FIGS. 3 and 4), and photosynthesis may be constrained to control plant levels (FIG. 5). The EAR domain appears to have a direct or indirect effect on guard cell physiology that is distinct from other phenotypes of 35S::AtHB17 expression in Arabidopsis. This effect manifests itself as an increased photosynthetic rate when the AtHB17 EAR mutant is constitutively overexpressed in Arabidopsis.

of numerous genes known to be involved in the regulation of stomatal opening and closure were found to be affected in different ways by overexpression of the full length wild-type AtHB17 protein compared to the EAR protein variant (FIG. 6). The expression of BGL1, KAT1 and KAT2 were significantly repressed in 35S::AtHB17 lines; however, their expression was close to control levels in EAR mutant lines (FIGS. 6A and 6B). BGLI (AtBG1), encoding a beta-glucosidase, is thought to regulate stomatal movement by producing active ABA through hydrolyzing glucose-conjugated, biologically inactive ABA. Loss of AtBG1 causes defective stomatal movement (Lee et al., 2006). KAT1 and KAT2, Arabidopsis K$^+$-channel-encoding genes expressed in guard cell, have been found to be critical to the opening of stomata and are induced by blue light and circadian rhythm (Lebaudy et al., 2008; Sata et al., 2010). Similarly, loss of repression in the expression of RD20, ABI1, MYB60 and CPK6 was observed in 35S::AtHB17 L84A L86A overexpressing lines. RD20, which encodes a calcium binding protein, plays an important role in drought tolerance through closing stomates during water deficit. The loss-of-function mutation, rd20, causes plants to exhibit increased stomatal opening and an elevated transpiration rate, as well as a reduced tolerance to drought as compared with the wild-type (Aubert et al., 2010). ABI1, encoding a phosphatase 2C protein, is a negative regulator of ABA-mediated stomatal closure (Gosti et al., 1999). In addition, loss of repression was observed for MYB60 and CPK6 in EAR mutant lines (FIG. 6D). Arabidopsis MYB60 is specifically expressed in guard cells. A loss of function mutation in this gene results in the constitutive reduction of stomatal opening, and decreased wilting under water stress conditions L84A L86A lines utilized nitrogen more efficiently than the empty vector control lines by accumulating the equivalent or more biomass with less nitrogen (Col. 7, the last three rows).

TABLE 5

| Col. 1 | Col. 2 Plant lines | Col. 3 Tissue Dry weight (g) | Col. 4 Nitrogen content (% N) | Col. 5 $^{15}$N/plant | Col. 6 Nitrogen Uptake Efficiency | Col. 7 NUE |
|---|---|---|---|---|---|---|
| 2 mM | pMEN65 | 0.010 ± 0.001 | 6.6 ± 0.2 | 67 ± 8 | 646 ± 857 | 0.15 ± 0.01 |
| | AtHB17 line 378-1 | 0.021 ± 0.004** | 6.0 ± 0.2** | 59 ± 34 | 3202 ± 1144* | 0.33 ± 0.06** |
| | AtHB17 line 373-22 | 0.013 ± 0.002 | 5.6 ± 0.4** | 62 ± 11 | 4438 ± 808 | 0.252 ± 0.03* |
| | AtHB17 line 370-23 | 0.018 ± 0.002** | 5.9 ± 0.5** | 87 ± 16 | 4057 ± 1198* | 0.29 ± 0.05** |
| | AtHB17 EAR line Z193346-14 | 0.030 ± 0.003** | 6.6 ± 0.4 | 297 ± 103** | 7875 ± 1358* | 0.46 ± 0.03** |
| | AtHB17 EAR line Z193358-14 | 0.030 ± 0.004** | 6.6 ± 0.7 | 267 ± 23** | 8697 ± 1476 | 0.47 ± 0.09** |
| | AtHB17 EAR line Z193359-1 | 0.026 ± 0.002** | 6.7 ± 0.6 | 202 ± 13** | 7752 ± 828 | 0.39 ± 0.05** |
| 10 mM | pMEN65 | 0.017 ± 0.002 | 7.5 ± 0.2 | 76 ± 7 | 6379 ± 683 | 0.20 ± 0.04 |
| | AtHB17 line 378-1 | 0.017 ± 0.003 | 62 ± 0.4** | 44 ± 20 | 2309 ± 779** | 027 ± 0.05 |
| | AtHB17 line 373-22 | 0.012 ± 0.002 | 5.8 ± 0.2** | 61 ± 15 | 6280 ± 751 | 0.20 ± 0.02 |
| | AtHB17 line 370-23 | 0.011 ± 0.003 | 6.2 ± 0.3** | 91 ± 29 | 5163 ± 346 | 0.15 ± 0.03 |
| | AtHB17 EAR line Z193346-14 | 0.022 ± 0.005 | 6.4 ± 0.3** | 162 ± 63** | 8622 ± 1745 | 0.35 ± 0.04** |
| | AtHB17 EAR line Z193358-14 | 0.025 ± 0.002** | 6.5 ± 0.3** | 70 ± 24 | 2754 ± 465 | 0.37 ± 0.07** |
| | AtHB17 EAR line Z193359-1 | 0.022 ± 0.006 | 6.6 ± 0.4** | 111 ± 22 | 4401 ± 805 | 0.34 ± 0.08** |

Significantly different from control at:
*p < 0.1,
**p < 0.05

(Cominelli et al., 2005). CPK6 has been reported to have an important role in guard cell ion channel regulation and stomatal movement (Mori et al., 2006).

Overexpression of EAR Mutant Variant of AtHB17 Increased Plant Size and Plant Biomass.

Previous experiments showed that overexpression of AtHB17 in *Arabidopsis* reduced plant growth and size. Further experiments showed that overexpression of the EAR mutation variant AtHB17 L84A L86A had no such adverse effects; on the contrary, these EAR mutation variant overexpressors were often larger and had greater biomass than control plants (FIG. 7B). SPAD analysis indicated overexpression of the AtHB17 EAR mutants moderately increased chlorophyll content levels; the chlorophyll levels of these EAR mutants were between those of the control plants and of the AtHB17 overexpressors (FIG. 7A).

Overexpression of EAR Mutant Variant of AtHB17 Increased Plant Nitrogen Use Efficiency ("NUE").

Experimental results in Table 5 showed that overexpression of EAR mutant variant significantly increased plant nitrogen use efficiency in *Arabidopsis*, more than overexpression of native AtHB17 did (Col. 7). In these experiments, a number of 35S::AtHB17 lines ("378-1", "373-22" and "370-23") and 35S::AtHB17 L84A L86A (EAR mutant variant lines of "Z193346-14", "Z193358-14", and "Z193359-1") lines were analyzed for nitrogen uptake and assimilation according to Example IV. When grown under nitrogen-limiting conditions (2 mM NO$_3$), 35S::AtHB17 and 35S::AtHB17 L84A L86A lines had increased NUE compared to the empty vector control line (pMEN65). 35S::AtHB17 lines accumulated more biomass (shown in Col. 3) with less nitrogen content (shown in Col. 4), and 35S::AtHB17 L84A L86A lines accumulated more biomass using the same amount of nitrogen as that found in the empty vector control lines (pMEN65). When grown under ample nitrogen conditions (10 mM NO$_3$), only the 35S::AtHB17

The AtHB17 Δ21 polypeptide, SEQ ID NO: 92, is identical to AtHB17, SEQ ID NO: 2, except for a deletion of amino acids 1-21 of the latter sequence. AtHB17 Δ21 has identical structural domains to AtHB17 Δ21, namely, the repression domain, the homeodomain, the homeodomain associated leucine zipper (HALZ domain), and the carboxy terminal "CPRCE" domain. The EAR mutant variant of AtHB17 A21 has also been constructed by introducing a leucine to alanine substitution at position 63 and 65.

It is expected that the EAR mutant variant of AtHB17 Δ21, SEQ ID NO: 93, will also confer modified traits as does the EAR mutant variant of AtHB17, SEQ ID NO: 21, when it is overexpressed in plants. These traits include, but are not limited to, higher nitrogen use efficiency, greater size, greater biomass, greater yield, greater growth rate, greater chlorophyll levels, greater photosynthetic capacity, greater photosynthetic rate and greater stomatal conductance.

It is also expected that the EAR mutation variant of AtHB17 Δ21, SEQ ID NO: 93 will have reduced transcriptional effect on genes involved in stomatal development and function relative to the native AtHB17 Δ21, SEQ ID NO: 92. Plants expressing SEQ ID NO: 93 will also have higher nitrogen use efficiency, greater stomatal conductance, lower chlorophyll levels, greater size, greater biomass, greater yield, and a greater growth rate relative to plants overexpressing SEQ ID NO: 92.

Example VI. Expression and Analysis of Increased Photosynthesis and Increased Yield in Non-*Arabidopsis* C3 or C4 Plants The EAR mutant variant of AtHB17 has been shown to confer increased photosynthetic rate, increased stomatal conductance, moderately increased chlorophyll content, increased plant size and/or increased biomass when the EAR mutant variant of AtHB17 was overexpressed in *Arabidop-* sis. Enhanced rates of photosynthesis are expected to result in increased crop yield in field conditions, including both C3 and C4 crop plants (Zhu et al., 2010). It is expected that similar EAR mutants derived from structurally similar orthologs of the AtHB17, such as those provided in the Sequence Listing, will confer similar improved traits in crop plants while eliminating the growth penalty associated with overexpression of the native AtHB17 homologs.

Overexpression of EAR mutation variants is expected to be especially beneficial for C3 plants, whose carbon fixation pathway is more sensitive to $CO_2$ limitation than C4 plants, The AtHB17 EAR mutant is ideally suited to C3 crops being grown on acres where water stress is modest and infrequent, where the benefits of increased photosynthetic capacity can be fully realized as increased photosynthetic rate. EAR mutation variants of the AtHB17 homologs can be employed to enhance plant photosynthesis, plant biomass, plant size, or yield in C3 plants, which include, but are not limited to, soybean, cotton, canola, rice, wheat, poplar, eucalyptus, and alfalfa.

After a C3 or C4 plant, or a C3 or C4 plant cell has been transformed (and the latter plant host cell regenerated into a plant) and shown to have greater size, greater photosynthetic rate at atmospheric CO2 condition, greater stomatal conductance, the transformed C3 or C4 plant may be crossed with itself or a plant from the same line, a non-transformed or wild-type C3 or C4 plant, or another transformed C3 or C4 plant from a different transgenic line of plants.

Northern blot analysis, RT-PCR or microarray analysis of the regenerated, transformed plants may be used to show expression of an EAR mutant class 11 HD-ZIP polypeptide of the instant disclosure and related genes that are capable of conferring greater photosynthetic rate, higher stomatal conductance and/or larger size.

The ectopic overexpression of EAR mutation variants of these AtHB17 homologous sequences may be regulated using constitutive, inducible, or tissue specific regulatory elements. In addition to these sequences, it is expected that EAR mutations can also be introduced into newly discovered polynucleotide and polypeptide sequences closely related to polynucleotide and polypeptide sequences found in the Sequence Listing and the mutant polynucleotide derived thereof can confer alteration of traits in a similar manner to the sequences found in the Sequence Listing, when transformed into any of a considerable variety of plants of different species, including both C3 and C4 plants.

Example VII. Soybean Plant Transformation

Similar to the experiments performed with *Arabidopsis*, EAR mutation variants of the disclosed or listed sequences can be generated and cloned into expression vectors under the control of suitable promoters and transformed into soybean plants. Transgenic soybean plants then can be analyzed for having an enhanced agronomic trait, e.g., enhanced yield, as compared to control plants. For *Agrobacterium* mediated transformation, soybean seeds are germinated overnight and the meristem explants excised. The meristems and the explants are placed in a wounding vessel. Soybean explants and induced *Agrobacterium* cells from a strain containing plasmid DNA with the gene of interest cassette and a plant selectable marker cassette are mixed no later than 14 hours from the time of initiation of seed germination and wounded using sonication. Following wounding, explants are placed in co-culture for 2-5 days at which point they are transferred to selection media for 6-8 weeks to allow selection and growth of transgenic shoots. Trait positive shoots are harvested approximately 6-8 weeks post bombardment and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil.

Example VIII. Corn Transformation

EAR mutation variants of the disclosed or listed sequences can also be introduced into corn plants. Corn plants of a readily transformable line are grown in the greenhouse and ears harvested when the embryos are 1.5 to 2.0 mm in length. Ears are surface sterilized by spraying or soaking the ears in 80% ethanol, followed by air drying. Immature embryos are isolated from individual kernels on surface sterilized ears. Prior to inoculation of maize cells, *Agrobacterium* cells are grown overnight at room temperature. Immature maize embryos are inoculated with *Agrobacterium* shortly after excision, and incubated at room temperature with *Agrobacterium* for 5-20 minutes. Immature embryos are then co-cultured with *Agrobacterium* for 1 to 3 days at 23° C. in the dark. Co-cultured embryos are transferred to selection media and cultured for approximately two weeks to allow embryogenic callus to develop. Embryogenic callus is transferred to culture medium containing a selective agent such as paromomycin or glyphosateand subcultured at about two week intervals. Transformants are recovered 6 to 8 weeks after initiation of selection.

Plant transformation vectors are prepared by cloning DNA identified in Table 1 in the appropriate base vector for use in corn transformation to produce transgenic corn plants and seed. Base vectors suitable for corn transformation are well known in the art.

For *Agrobacterium*-mediated transformation of maize callus, immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media, and paromomycin resistant callus identified as containing the recombinant DNA in an expression cassette.

For transformation by microprojectile bombardment, immature maize embryos are isolated and cultured 3-4 days prior to bombardment. Prior to microprojectile bombardment, a suspension of gold particles is prepared onto which the desired recombinant DNA expression cassettes are precipitated. DNA is introduced into maize cells as described in U.S. Pat. Nos. 5,550,318 and 6,399,861 using the electric discharge particle acceleration gene delivery device. Following microprojectile bombardment, tissue is cultured in the dark at 27 degrees C.

To regenerate transgenic corn plants trangenic callus resulting from transformation is placed on media to initiate shoot, followed by root development into plantlets, which are transferred to potting soil for initial growth in a growth chamber at 26 degrees C. followed by a mist bench before transplanting to 5 inch pots where plants are grown to maturity. The plants are self fertilized and seed is harvested for screening as seed, seedlings or progeny plants or hybrids, e.g., for yield trials.

Example VIII. Sugarcane Transformation

EAR mutation variants of the disclosed or listed sequences can also be introduced into Sugarcane plants, using methods that are well-known in the art. Sugarcane has been successfully transformed using either direct or indirect somatic embryogenesis routes. See, Bower and Birch, Plant J. 2:209-416 (1992); Falco et al. *Plant Cell Rep* 19:1188-1194 (2000); Snyman et al. *Plant Cell Rep.* 25:1016-1023 (2006); Van Der Vyver, *Sugar Tech* 12:21-25 (2010); Kalunke et al., *Sugar Tech* 11: 355-359 (2009). *Agrobacterium*-mediated sugarcane transformation using either embryogenic callus or axillary bud as explants are also well-established. See Brumbley et al., Sugarcane. In: Kole C. Hall T C (eds), Compendium of transgenic crop plants: transgenic sugar, tuber and fiber crops. Blackwell, Oxford, pp 1-58 (2008). See also Arencibia et al. for discussion on the type and age of sugarcane explants. Arencibia et al, *Transgenic Res* 7:213-222 (1998) and Enriquez-Obregon et al for targeted pre-conditioned meristermatic sections to produce transgenic plants. Procedures described in WO 2011/163292 A1 or WO 02/37951 A1 can also be used to produce transgenic Sugarcane plants. The entire content of these references are hereby incorporated by reference.

REFERENCES

Arid F D, Manavella P A, Dezar C A, Chan R L (2007) Trends Plant Sci 12: 419-426
Affolter, M., Percival-Smith, A., Mujller, M., Leupin, W., & Gerhring, W. J. (1990) Proc. Natl. Acad. Sci. U.S.A. 87, 4093-4097
Aubert Y, Vile D, Pervent M, Aldon D, Ranty B, Simonneau T, Vavasseur A, Galaud J P (2010) Plant Cell Physiol 51, 1975-1987
Arencibia et al. (1998) *Transgenic Res* 7:213-222
Bower and Birch, (1992) *Plant J.* 2:409-416
Brumbley et al., (2008) Sugarcane. In: Kole C, Hall T C (eds) Compendium of transgenic crop plants: transgenic sugar, tuber and fiber crops. Blackwell, Oxford, pp 1-58, Carabelli, M., Sessa, G., Baima, S., Morelli, G., and Ruberti, I. (1993) Plant J 4, 469-479
Chardon F, Barthelemy J, Daniel-Vedele F, Masclaux-Daubresse C (2010) Natural variation of nitrate uptake and nitrogen use efficiency in *Arabidopsis thaliana* cultivated with limiting and ample nitrogen supply. J Exp Bot 61: 2293-2302
Ciarbelli A R, Ciolfi A, Salvucci S, Ruzza V, Possenti M, Carabelli M, Fruscalzo A, Sessa G, Morelli G, Ruberti I (2008) Plant Mol Biol 68, 465-478
Cheikh et al. (2003) U.S. Patent Application No. 20030101479
Clough S J, Bent A F (1998) Plant J.; 16:735-43
Cominelli E, Galbiati M, Vavasscur A, Conti L, Sala T, Vuylsteke M, Lconhardt N, Dellaporta S L, Tonelli C (2005) Curr Biol 15, 1196-1200
De Blaere et. al. (1987) Meth. Enzymol., vol. 153:277-292
Elliott et. al, (1998) *Aust J Plant Physiol* 25:739-743
Enriquez-Obregon et al. (1998) *Planta* 206:20-27
Falco et al. (2000) *Plant Cell Rep.* 19:1188-1194,
Genty B, Briantais J-M, Baker N R (1989). Biochim Biophys Acta 990: 87-92
Good, A. G., Shrawat, A. K., and Muench, D. G. (2004). Can less yield more? Is reducing nutrient input into the environment compatible with maintaining crop production? Trends Plant Sci 9, 597-605
Coosti F, Beaudoin N, Serizet C, Webb A A, Vartanian N, Giraudat J (1999) Plant Cell 11, 1897-1910
Hanes, S. D. & Brent R. (1989) Cell 57, 1275-1283
Hill K. et al., 2008 Plant J 53, 172-185
Ikeda M, Ohme-Takagi M (2009) Plant Cell Physiol 50, 970-975
Jain et al. (2008) FEBS J. 11: 2845-2861
Kagale S, Links M G, Rozwadowski K (2010) Plant Physiol 152, 1109-1134
Kalunke et al. (2009) *Sugar Tech* 11: 355-359
Ku et al. (2000) *Proc. Natl. Acad. Sci. USA* 97: 9121-9126
Lebaudy A et al. (2008) Proc Natl Acad Sci USA 105, 5271-5276
Lee K H et al (2006) Cell 126, 1109-20
Lemaitre T, Gaufichon L, Boutet-Mercey S, Christ A, Masclaux-Daubresse C (2008) Enzymatic and metabolic diagnostic of nitrogen deficiency in *Arabidopsis thaliana* Wassileskija accession. Plant Cell Physiol 49: 1056-1065
Long S P, Bernacchi C J (2003) Journal of Experimental Botany 54: 2393-2401.
McCallum et al. (2000) *Nature Biotech.* 18, 455-457
Mori I C et al (2006). PLoS Biol 4, 1749-1762
Ohgishi M, Oka A, Morelli G, Ruberti I, Aoyama T (2001) Plant J 25, 389-398
Reeves and Nissen (1995) *Prog. Cell Cycle Res.* 1: 339-349
Rice, P. Longden, I. and Bleasby, A. (2000) Trends in Genetics 16, (6) pp 276-277
Riechmann et al. (2000a) *Science* 290, 2105-2110
Riechmann and Ratcliffe (2000b) *Curr. Opin. Plant Biol.* 3, 423-434
Rieger et al. (1976) *Glossary of Genetics and Cytogenetics: Classical and Molecular,* 4th ed., Springer Verlag, Berlin
Ruberti, I., Sessa, G., Lucchetti, S., and Morelli, G. (1991) Embo J 10, 1787-1791
Santosa et al., (2004) Biotechnology 28:113-119
Sato A, Gambale F, Dreyer I, Uozumi N (2010) Febs J 277, 2318-2328
Sawa S, Ohgishi M, Goda H, Higuchi K, Shimada Y, Yoshida S, Koshiba T (2002) Plant J 32, 1011-1022
Schena, M., Lloyd, A. M., and Davis, R. W. (1993) Genes Dev 7, 367-379.
Sessa, G., Morelli, G., and Ruberti, I. (1993) Embo J 12, 3507-3517
Sharkey T D, Bernacchi C J, Farquhar G D, Singsaas E L (2007) Plant, Cell and Environment 30: 1035-1040.
Smith et al. (1992) *Protein Engineering* 5: 35-51
Snyman et al. (2006) *Cell Rep.* 25:1016-1023
Steindler C, Matteucci A, Sessa G, Weimar T, Ohgishi M, Aoyama T, Morelli G, Ruberti I (1999) Development 126, 4235-4245
Szemenyei H. et al., 2008. Science 319, 1384-1386
Taparia et al. (2012) *In Vitro Cell. Dev. Biol.—Plant* 48:15-22
Tiwari S B, Hagen C, Guilfoyle T J (2004) Plant Cell 16, 533-543
Tiwari S., Wang S., Hagen G., and Guilfoyle T. J. (2006) Methods Mol Biol 323, 237-244
Tudge (2000) in *The Variety of Life*, Oxford University Press, New York, N.Y. pp. 547-606
Zhu X-G, Long S P, Ort D R (2010) Annual Review of Plant Biology 61, 235-261
Van Der Vyver, (2010) *Sugar Tech* 12:21-25, The above examples are provided to illustrate the disclosure but not to limit its scope. Although the foregoing disclosure has been described in some detail by way of illustration and example for, purposes of clarity of understanding, it will be obvious that certain changes and modifications may be practiced within the scope of the appended claims. All publications, databases, Genbank sequences, patents, and patent applications cited herein are hereby incorporated by reference to the same extent as if each individual publication or patent application was specifically and individually indicated to be incorporated by reference.

What is claimed is:

1. A transgenic plant comprising an improved trait relative to a first control plant of the same species
    wherein the transgenic plant comprises a recombinant polynucleotide encoding a polypeptide that comprises:
    a mutant EAR motif of $X_1$-$X_2$-$X_3$-$X_4$-$X_5$ (set forth in SEQ ID NO: 1), where $X_1$ and $X_3$ are glycine, alanine, asparagine, glutamine, serine, threonine, phenylalanine, or tyrosine; $X_2$ and $X_4$ are any amino acid; and $X_5$ is isoleucine, leucine or methionine;
    wherein the polypeptide comprises an amino acid sequence having at least 90% sequence identity to SEQ ID NO:3;
    wherein said polypeptide confers the improved trait which is selected from the group consisting of: higher nitrogen use efficiency, greater stomatal conductance, greater chlorophyll levels, greater size, greater biomass, and greater yield.

2. The transgenic plant of claim 1, wherein the transgenic plant has improved traits relative to a second control plant of the same species, wherein the second control plant is a wild type or non-transformed plant of the same species;
    wherein the improved trait is selected from the group consisting of: higher nitrogen use efficiency, greater size, greater biomass, greater yield, greater chlorophyll levels, greater photosynthetic capacity, greater photosynthetic rate and greater stomatal conductance.

3. The transgenic plant of claim 1, wherein the polypeptide is at least 91%, at least 92%, at least 93%, at least 94%, at least 95%, at least 96%, at least 97%, at least 98%, at least 99%, or about 100% identical to the full length sequence of any of SEQ ID NO:3.

4. The transgenic plant of claim 1, 2 or 3, wherein $X_1$ or $X_3$, or both $X_1$ and $X_3$ are alanine residues.

5. The transgenic plant of any of claims 1-4, wherein the transgenic plant is a C3 plant.

6. The transgenic plant of claim 1, wherein the transgenic plant is a legume.

7. The transgenic plant of claim 1, wherein the transgenic legume is a soybean plant.

8. A plant material or plant part produced from the transgenic plant of claim 1, wherein the plant material or plant part comprises the polypeptide.

9. A transgenic seed produced by the transgenic plant of claim 1, wherein the plant comprises the recombinant polynucleotide.

10. The transgenic plant of claim 4, wherein $X_2$ is aspartic acid and $X_4$ is threonine.

11. A method for conferring an improved trait to a plant, the method comprising:
    (a) providing a polynucleotide encoding a first Class II HD-Zip subfamily polypeptide that comprises (1) a homeodomain that shares an amino acid percentage identity to a homeodomain of SEQ ID NO:3 of at least 90%; and
(2) a homeobox-associated leucine zipper (HALZ) domain that shares an amino acid percentage identity to a HALZ domain set forth in SEQ ID NO:3;
(b) mutagenizing the polynucleotide, wherein the mutagenized polynucleotide encodes a mutant polypeptide comprising a mutant EAR motif of $X_1$-$X_2$-$X_3$-$X_4$-$X_5$ (set forth in SEQ ID NO: 1), where $X_1$ and $X_3$ are glycine, alanine, asparagine, glutamine, serine, threonine, phenylalanine, or tyrosine; $X_2$ and $X_4$ are any amino acid; and $X_5$ is isoleucine, leucine or methionine;
(c) introducing the mutagenized polynucleotide into a target plant to produce a transgenic plant, wherein expression of the mutagenized polynucleotide confers the improved trait in the transgenic plant; and
(d) optionally, selecting the transgenic plant having the improved trait;
wherein the improved trait is selected from the group consisting of: greater nitrogen use efficiency, greater stomatal conductance, greater chlorophyll levels, greater photosynthetic capacity, greater photosynthetic rate, greater stomatal conductance, greater size, and greater yield relative to a wild-type or non-transformed control plant of the same species.

12. The method of claim 11, wherein the first polypeptide is at least 91%, at least 92%, at least 93, at least 94%, at least 95%, at least 96%, at least 97%, at least 98%, at least 99%, or about 100% identical to the full length sequence of SEQ ID NO:3.

13. The method of claim 11 or claim 12, wherein $X_1$ or $X_3$, or both $X_1$ and $X_3$ are alanine.

14. The method of claim 11, 12, or 13, wherein the transgenic plant is a C3 plant.

15. The method of claim 14, wherein the transgenic C3 plant is a dicot plant.

16. The method of claim 14, wherein the transgenic C3 plant is a legume.

17. The method of claim 14, wherein the transgenic C3 plant is a soybean plant.

18. The method of any of claims 11-17, wherein the transcriptional repression activity of the mutant polypeptide is less than that of the first polypeptide.

* * * * *

```
                          SEQUENCE LISTING

<160> NUMBER OF SEQ ID NOS: 94

<210> SEQ ID NO 1
<211> LENGTH: 5
<212> TYPE: PRT
<213> ORGANISM: artificial sequence
<220> FEATURE:
<223> OTHER INFORMATION: mutated EAR motif sequence
<220> FEATURE:
<221> NAME/KEY: MISC_FEATURE
<222> LOCATION: (1)..(1)
<223> OTHER INFORMATION: X is any amino acid other than leucine,
      isoleucine, or valine
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is any amino acid other than leucine,
      isoleucine, or valine
<220> FEATURE:
<221> NAME/KEY: MISC_FEATURE
<222> LOCATION: (4)..(4)
<223> OTHER INFORMATION: X is any amino acid
<220> FEATURE:
<221> NAME/KEY: MISC_FEATURE
<222> LOCATION: (5)..(5)
<223> OTHER INFORMATION: X is any amino acid selected from the group
      consisting of isoleucine, leucine and methionine

<400> SEQUENCE: 1

Xaa Xaa Xaa Xaa Xaa
1               5

<210> SEQ ID NO 2
<211> LENGTH: 275
<212> TYPE: PRT
<213> ORGANISM: Arabidopsis thaliana
<220> FEATURE:
<223> OTHER INFORMATION: AtHB17

<400> SEQUENCE: 2

Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Arg Asp Gln Leu Arg Leu
            100                 105                 110

Asp Met Asn Arg Leu Pro Ser Ser Glu Asp Gly Asp Asp Glu Glu Phe
            115                 120                 125
```

-continued

Ser His Asp Asp Gly Ser Ala Pro Pro Arg Lys Lys Leu Arg Leu Thr
130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190

Leu Lys Gln Thr Glu Met Glu Cys Glu Tyr Leu Lys Arg Trp Phe Gly
        195                 200                 205

Ser Leu Thr Glu Glu Asn His Arg Leu His Arg Glu Val Glu Glu Leu
210                 215                 220

Arg Ala Ile Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
275

<210> SEQ ID NO 3
<211> LENGTH: 213
<212> TYPE: PRT
<213> ORGANISM: Glycine max
<220> FEATURE:
<223> OTHER INFORMATION: G3524

<400> SEQUENCE: 3

Met Ala Val Leu Pro Ser Ser Ser Ser Leu Glu Leu Thr Ile Ser
1               5                   10                  15

Val Pro Gly Phe Ala Ser Ser Pro Thr Leu Leu Pro Ser Ser Ser Val
                20                  25                  30

Lys Glu Leu Asp Ile Asn Gln Val Pro Leu Glu Glu Asp Trp Met Ala
            35                  40                  45

Ser Asn Met Glu Asp Glu Glu Glu Ser Ser Asn Gly Glu Pro Pro Arg
        50                  55                  60

Lys Lys Leu Arg Leu Thr Lys Glu Gln Ser Arg Leu Leu Glu Glu Ser
65                  70                  75                  80

Phe Arg Gln Asn His Thr Leu Asn Pro Lys Gln Lys Glu Ser Leu Ala
                85                  90                  95

Met Gln Leu Lys Leu Arg Pro Arg Gln Val Glu Val Trp Phe Gln Asn
            100                 105                 110

Arg Arg Ala Arg Ser Lys Leu Lys Gln Thr Glu Met Glu Cys Glu Tyr
        115                 120                 125

Leu Lys Arg Trp Phe Gly Ser Leu Thr Glu Gln Asn Arg Arg Leu Gln
    130                 135                 140

Arg Glu Val Glu Glu Leu Arg Ala Ile Lys Val Gly Pro Pro Thr Val
145                 150                 155                 160

Ile Ser Pro His Ser Cys Glu Pro Leu Pro Ala Ser Thr Leu Ser Met
                165                 170                 175

Cys Pro Arg Cys Glu Arg Val Thr Ser Thr Ala Asp Lys Pro Pro Ser
            180                 185                 190

Ala Ala Ala Thr Leu Ser Ala Lys Val Pro Pro Thr Gln Ser Arg Gln
        195                 200                 205

```
Pro Ser Ala Ala Cys
    210

<210> SEQ ID NO 4
<211> LENGTH: 229
<212> TYPE: PRT
<213> ORGANISM: Oryza sativa
<220> FEATURE:
<223> OTHER INFORMATION: G3510

<400> SEQUENCE: 4

Met Met Gly Ala Thr Ser Pro Ser Gly Leu Glu Leu Thr Met Ala Val
1               5                   10                  15

Pro Gly Leu Ser Ser Gly Ser Glu Gly Ala Gly Cys Asn Asn Asn
            20                  25                  30

Asn Ala Gly Gly Gly Cys Asn Met Arg Asp Leu Asp Ile Asn Gln Pro
        35                  40                  45

Ala Ser Gly Gly Glu Glu Glu Phe Pro Met Gly Ser Val Glu Glu
    50                  55                  60

Asp Glu Glu Glu Arg Gly Val Gly Gly Pro His Arg Pro Lys Lys Leu
65                  70                  75                  80

Arg Leu Ser Lys Glu Gln Ser Arg Leu Leu Glu Ser Phe Arg Leu
                85                  90                  95

Asn His Thr Leu Thr Pro Lys Gln Lys Glu Ala Leu Ala Ile Lys Leu
            100                 105                 110

Lys Leu Arg Pro Arg Gln Val Glu Val Trp Phe Gln Asn Arg Arg Ala
        115                 120                 125

Arg Thr Lys Leu Lys Gln Thr Glu Met Glu Cys Glu Tyr Leu Lys Arg
    130                 135                 140

Cys Phe Gly Ser Leu Thr Glu Glu Asn Arg Arg Leu Gln Arg Glu Val
145                 150                 155                 160

Glu Glu Leu Arg Ala Met Arg Val Ala Pro Pro Thr Val Leu Ser Pro
                165                 170                 175

His Thr Arg Gln Pro Leu Pro Ala Ser Ala Leu Thr Met Cys Pro Arg
            180                 185                 190

Cys Glu Arg Ile Thr Ala Ala Thr Gly Pro Pro Ala Val Arg Pro Pro
        195                 200                 205

Pro Ser Ser Ala Ala Ala Ala Pro Ser Pro Phe His Pro Arg Arg
    210                 215                 220

Pro Ser Ala Ala Phe
225

<210> SEQ ID NO 5
<211> LENGTH: 213
<212> TYPE: PRT
<213> ORGANISM: Glycine max
<220> FEATURE:
<223> OTHER INFORMATION: G4371

<400> SEQUENCE: 5

Met Ala Val Leu Pro Ser Ser Ser Ser Leu Glu Leu Thr Ile Ser
1               5                   10                  15

Val Pro Gly Phe Ala Ser Ser Pro Thr Leu Leu Pro Ser Ser Ser Val
            20                  25                  30

Lys Glu Leu Asp Ile Asn Gln Val Pro Leu Glu Glu Asp Trp Met Ala
        35                  40                  45

Ser Asn Met Glu Asp Glu Glu Glu Ser Ser Asn Gly Glu Pro Pro Arg
```

```
                50                  55                  60
Lys Lys Leu Arg Leu Thr Lys Glu Gln Ser Leu Leu Glu Glu Ser
 65                  70                  75                  80

Phe Arg Gln Asn His Thr Leu Asn Pro Lys Gln Lys Glu Ser Leu Ala
                 85                  90                  95

Met Gln Leu Lys Leu Arg Pro Arg Gln Val Glu Val Trp Phe Gln Asn
                100                 105                 110

Arg Arg Ala Arg Ser Lys Leu Lys Gln Thr Glu Met Glu Cys Glu Tyr
                115                 120                 125

Leu Lys Arg Trp Phe Gly Ser Leu Thr Glu Gln Asn Arg Arg Leu Gln
130                 135                 140

Arg Glu Val Glu Glu Leu Arg Ala Ile Lys Val Gly Pro Pro Thr Val
145                 150                 155                 160

Ile Ser Pro His Ser Cys Glu Pro Leu Pro Ala Ser Thr Leu Ser Met
                165                 170                 175

Cys Pro Arg Cys Glu Arg Val Thr Ser Thr Ala Asp Lys Pro Pro Ser
                180                 185                 190

Ala Ala Ala Thr Leu Ser Ala Lys Val Pro Pro Thr Gln Ser Arg Gln
                195                 200                 205

Pro Ser Ala Ala Cys
    210

<210> SEQ ID NO 6
<211> LENGTH: 225
<212> TYPE: PRT
<213> ORGANISM: Zea mays
<220> FEATURE:
<223> OTHER INFORMATION: G4369

<400> SEQUENCE: 6

Met Gly Ser Thr Ser Pro Ser Gly Leu Glu Leu Thr Met Ala Val Pro
 1               5                  10                  15

Gly Leu Ser Ser Ser Gly Ser Glu Gly Phe Gly Cys Asn Asn Asn
                 20                  25                  30

Asn Gly Ser Gly Asn Gly Asn Asn Met Arg Asp Leu Asp Met Asn Gln
                35                  40                  45

Pro Ala Ser Gly Gly Glu Glu Glu Phe Pro Met Gly Ser Val Glu
 50                  55                  60

Glu Glu Glu Asp Glu Arg Gly Gly Ala Gly Gly Pro His Arg Ala Lys
 65                  70                  75                  80

Lys Leu Arg Leu Ser Lys Glu Gln Ser Arg Leu Leu Glu Glu Ser Phe
                 85                  90                  95

Arg Leu Asn His Thr Leu Thr Pro Lys Gln Lys Glu Ala Leu Ala Val
                100                 105                 110

Lys Leu Lys Leu Arg Pro Arg Gln Val Glu Val Trp Phe Gln Asn Arg
                115                 120                 125

Arg Ala Arg Thr Lys Leu Lys Gln Thr Glu Leu Glu Cys Glu Tyr Leu
                130                 135                 140

Lys Arg Cys Phe Gly Ser Leu Thr Glu Glu Asn Arg Arg Leu Gln Arg
145                 150                 155                 160

Glu Val Glu Glu Leu Arg Ala Met Arg Val Ala Pro Pro Thr Val Leu
                165                 170                 175

Ser Pro His Thr Arg Gln Pro Leu Pro Ala Ser Ala Leu Thr Met Cys
                180                 185                 190

Pro Arg Cys Glu Arg Ile Thr Ala Ala Thr Ala Ala Arg Thr Pro Arg
```

```
                    195                 200                 205

Pro Pro Pro Ala Ala Ser Pro Phe His Pro Arg Arg Pro Ser Ala Ala
        210                 215                 220

Phe
225

<210> SEQ ID NO 7
<211> LENGTH: 222
<212> TYPE: PRT
<213> ORGANISM: Zea mays
<220> FEATURE:
<223> OTHER INFORMATION: G4370

<400> SEQUENCE: 7

Met Gly Ala Thr Ser Pro Ser Gly Leu Glu Leu Thr Met Ala Val Pro
1               5                   10                  15

Gly Leu Ser Ser Ser Gly Ser Glu Gly Phe Val Cys Asn Asn Asn
            20                  25                  30

Ile Ser Asn Asn Gly Gly Gly Asn Met Arg Asp Leu Asp Met Asn Gln
        35                  40                  45

Pro Ala Ser Gly Gly Glu Glu Glu Asp Phe Leu Met Gly Gly Val Glu
    50                  55                  60

Glu Asp Glu Glu Glu Arg Gly Ala Gly Gly Pro His Arg Pro Lys Lys
65                  70                  75                  80

Leu Arg Leu Ser Lys Glu Gln Ser Arg Leu Leu Glu Glu Ser Phe Arg
                85                  90                  95

Leu Asn His Thr Leu Ser Pro Lys Gln Lys Glu Ala Leu Ala Ile Lys
            100                 105                 110

Leu Lys Leu Arg Pro Arg Gln Val Glu Val Trp Phe Gln Asn Arg Arg
        115                 120                 125

Ala Arg Thr Lys Leu Lys His Thr Glu Met Glu Cys Glu Tyr Leu Lys
    130                 135                 140

Arg Cys Phe Gly Ser Leu Thr Glu Glu Asn Arg Arg Leu Gln Arg Glu
145                 150                 155                 160

Val Glu Glu Leu Arg Ala Met Arg Met Ala Pro Pro Thr Val Leu Ser
                165                 170                 175

Pro His Thr Arg Gln Pro Leu Pro Ala Ser Ala Leu Thr Met Cys Pro
            180                 185                 190

Arg Cys Glu Arg Val Thr Ala Ala Thr Cys Pro Arg Ile Thr Arg Pro
        195                 200                 205

Ala Ala Ser Pro Phe His Pro Arg Arg Pro Ser Ala Ala Phe
    210                 215                 220

<210> SEQ ID NO 8
<211> LENGTH: 206
<212> TYPE: PRT
<213> ORGANISM: Arabidopsis thaliana
<220> FEATURE:
<223> OTHER INFORMATION: G2712

<400> SEQUENCE: 8

Met Ala Leu Ser Pro Asn Ser Ser Ser Leu Asp Leu Thr Ile Ser Ile
1               5                   10                  15

Pro Ser Phe Ser Pro Ser Pro Ser Leu Gly Asp His His Gly Met Arg
            20                  25                  30

Asp Phe Asp Ile Asn Gln Thr Pro Lys Thr Glu Glu Asp Arg Glu Trp
        35                  40                  45
```

```
Met Ile Gly Ala Thr Pro His Val Asn Glu Asp Asp Ser Asn Ser Gly
    50                  55                  60
Gly Arg Arg Arg Lys Lys Leu Arg Leu Thr Lys Glu Gln Ser His Leu
65                  70                  75                  80
Leu Glu Glu Ser Phe Ile Gln Asn His Thr Leu Thr Pro Lys Gln Lys
                85                  90                  95
Lys Asp Leu Ala Thr Phe Leu Lys Leu Ser Gln Arg Gln Val Glu Val
            100                 105                 110
Trp Phe Gln Asn Arg Arg Ala Arg Ser Lys Leu Lys His Thr Glu Met
            115                 120                 125
Glu Cys Glu Tyr Leu Lys Arg Trp Phe Gly Ser Leu Lys Glu Gln Asn
130                 135                 140
Arg Arg Leu Gln Ile Glu Val Glu Glu Leu Arg Ala Leu Lys Pro Ser
145                 150                 155                 160
Ser Thr Ser Ala Leu Thr Met Cys Pro Arg Cys Glu Arg Val Thr Asp
                165                 170                 175
Ala Val Asp Asn Asp Ser Asn Ala Val Gln Glu Gly Ala Val Leu Ser
            180                 185                 190
Ser Arg Ser Arg Met Thr Ile Ser Ser Ser Ser Leu Cys
            195                 200                 205

<210> SEQ ID NO 9
<211> LENGTH: 284
<212> TYPE: PRT
<213> ORGANISM: Arabidopsis thaliana
<220> FEATURE:
<223> OTHER INFORMATION: G400

<400> SEQUENCE: 9

Met Met Phe Glu Lys Asp Asp Leu Gly Leu Ser Leu Gly Leu Asn Phe
1               5                   10                  15
Pro Lys Lys Gln Ile Asn Leu Lys Ser Asn Pro Ser Val Ser Val Thr
                20                  25                  30
Pro Ser Ser Ser Ser Phe Gly Leu Phe Arg Arg Ser Ser Trp Asn Glu
            35                  40                  45
Ser Phe Thr Ser Ser Val Pro Asn Ser Asp Ser Ser Gln Lys Glu Thr
    50                  55                  60
Arg Thr Phe Ile Arg Gly Ile Asp Val Asn Arg Pro Pro Ser Thr Ala
65                  70                  75                  80
Glu Tyr Gly Asp Glu Asp Ala Gly Val Ser Ser Pro Asn Ser Thr Val
                85                  90                  95
Ser Ser Ser Thr Gly Lys Arg Ser Glu Arg Glu Glu Asp Thr Asp Pro
            100                 105                 110
Gln Gly Ser Arg Gly Ile Ser Asp Asp Glu Asp Gly Asp Asn Ser Arg
            115                 120                 125
Lys Lys Leu Arg Leu Ser Lys Asp Gln Ser Ala Ile Leu Glu Glu Thr
130                 135                 140
Phe Lys Asp His Ser Thr Leu Asn Pro Lys Gln Lys Gln Ala Leu Ala
145                 150                 155                 160
Lys Gln Leu Gly Leu Arg Ala Arg Gln Val Glu Val Trp Phe Gln Asn
                165                 170                 175
Arg Arg Ala Arg Thr Lys Leu Lys Gln Thr Glu Val Asp Cys Glu Phe
            180                 185                 190
Leu Arg Arg Cys Cys Glu Asn Leu Thr Glu Glu Asn Arg Arg Leu Gln
            195                 200                 205
```

```
Lys Glu Val Thr Glu Leu Arg Ala Leu Lys Leu Ser Pro Gln Phe Tyr
210                 215                 220

Met His Met Ser Pro Thr Thr Leu Thr Met Cys Pro Ser Cys Glu
225                 230                 235                 240

His Val Ser Val Pro Pro Gln Pro Gln Ala Ala Thr Ser Ala His
                245                 250                 255

His Arg Ser Leu Pro Val Asn Ala Trp Ala Pro Ala Thr Arg Ile Ser
            260                 265                 270

His Gly Leu Thr Phe Asp Ala Leu Arg Pro Arg Ser
        275                 280

<210> SEQ ID NO 10
<211> LENGTH: 283
<212> TYPE: PRT
<213> ORGANISM: Arabidopsis thaliana
<220> FEATURE:
<223> OTHER INFORMATION: G399

<400> SEQUENCE: 10

Met Met Met Gly Lys Glu Asp Leu Gly Leu Ser Leu Ser Leu Gly Phe
1               5                   10                  15

Ser Gln Asn His Asn Pro Leu Gln Met Asn Leu Asn Pro Asn Ser Ser
            20                  25                  30

Leu Ser Asn Asn Leu Gln Arg Leu Pro Trp Asn Gln Thr Phe Asp Pro
        35                  40                  45

Thr Ser Asp Leu Arg Lys Ile Asp Val Asn Ser Phe Pro Ser Thr Val
    50                  55                  60

Asn Cys Glu Glu Asp Thr Gly Val Ser Ser Pro Asn Ser Thr Ile Ser
65                  70                  75                  80

Ser Thr Ile Ser Gly Lys Arg Ser Glu Arg Glu Gly Ile Ser Gly Thr
                85                  90                  95

Gly Val Gly Ser Gly Asp Asp His Asp Glu Ile Thr Pro Asp Arg Gly
            100                 105                 110

Tyr Ser Arg Gly Thr Ser Asp Glu Glu Glu Asp Gly Gly Glu Thr Ser
        115                 120                 125

Arg Lys Lys Leu Arg Leu Ser Lys Asp Gln Ser Ala Phe Leu Glu Glu
    130                 135                 140

Thr Phe Lys Glu His Asn Thr Leu Asn Pro Lys Gln Lys Leu Ala Leu
145                 150                 155                 160

Ala Lys Lys Leu Asn Leu Thr Ala Arg Gln Val Glu Val Trp Phe Gln
                165                 170                 175

Asn Arg Arg Ala Arg Thr Lys Leu Lys Gln Thr Glu Val Asp Cys Glu
            180                 185                 190

Tyr Leu Lys Arg Cys Val Glu Lys Leu Thr Glu Glu Asn Arg Arg Leu
        195                 200                 205

Gln Lys Glu Ala Met Glu Leu Arg Thr Leu Lys Leu Ser Pro Gln Phe
    210                 215                 220

Tyr Gly Gln Met Thr Pro Pro Thr Thr Leu Ile Met Cys Pro Ser Cys
225                 230                 235                 240

Glu Arg Val Gly Gly Pro Ser Ser Ser Asn His His Asn His Arg
                245                 250                 255

Pro Val Ser Ile Asn Pro Trp Val Ala Cys Ala Gly Gln Val Ala His
            260                 265                 270

Gly Leu Asn Phe Glu Ala Leu Arg Pro Arg Ser
        275                 280
```

```
<210> SEQ ID NO 11
<211> LENGTH: 282
<212> TYPE: PRT
<213> ORGANISM: Arabidopsis thaliana
<220> FEATURE:
<223> OTHER INFORMATION: G398

<400> SEQUENCE: 11

Met Met Met Gly Lys Glu Asp Leu Gly Leu Ser Leu Ser Leu Gly Phe
1               5                   10                  15

Ala Gln Asn His Pro Leu Gln Leu Asn Leu Lys Pro Thr Ser Ser Pro
            20                  25                  30

Met Ser Asn Leu Gln Met Phe Pro Trp Asn Gln Thr Leu Val Ser Ser
        35                  40                  45

Ser Asp Gln Gln Lys Gln Gln Phe Leu Arg Lys Ile Asp Val Asn Ser
    50                  55                  60

Leu Pro Thr Thr Val Asp Leu Glu Glu Glu Thr Gly Val Ser Ser Pro
65                  70                  75                  80

Asn Ser Thr Ile Ser Ser Thr Val Ser Gly Lys Arg Arg Ser Thr Glu
                85                  90                  95

Arg Glu Gly Thr Ser Gly Gly Gly Cys Gly Asp Asp Leu Asp Ile Thr
            100                 105                 110

Leu Asp Arg Ser Ser Ser Arg Gly Thr Ser Asp Glu Glu Glu Asp Tyr
        115                 120                 125

Gly Gly Glu Thr Cys Arg Lys Lys Leu Arg Leu Ser Lys Asp Gln Ser
    130                 135                 140

Ala Val Leu Glu Asp Thr Phe Lys Glu His Asn Thr Leu Asn Pro Lys
145                 150                 155                 160

Gln Lys Leu Ala Leu Ala Lys Lys Leu Gly Leu Thr Ala Arg Gln Val
                165                 170                 175

Glu Val Trp Phe Gln Asn Arg Arg Ala Arg Thr Lys Leu Lys Gln Thr
            180                 185                 190

Glu Val Asp Cys Glu Tyr Leu Lys Arg Cys Val Glu Lys Leu Thr Glu
        195                 200                 205

Glu Asn Arg Arg Leu Glu Lys Glu Ala Ala Glu Leu Arg Ala Leu Lys
    210                 215                 220

Leu Ser Pro Arg Leu Tyr Gly Gln Met Ser Pro Thr Thr Leu Leu
225                 230                 235                 240

Met Cys Pro Ser Cys Glu Arg Val Ala Gly Pro Ser Ser Asn His
                245                 250                 255

Asn Gln Arg Ser Val Ser Leu Ser Pro Trp Leu Gln Met Ala His Gly
            260                 265                 270

Ser Thr Phe Asp Val Met Arg Pro Arg Ser
        275                 280

<210> SEQ ID NO 12
<211> LENGTH: 230
<212> TYPE: PRT
<213> ORGANISM: Sorghum bicolor
<220> FEATURE:
<223> OTHER INFORMATION: SbHB17

<400> SEQUENCE: 12

Met Gly Ser Thr Ser Pro Ser Gly Leu Glu Leu Thr Met Ala Val Pro
1               5                   10                  15

Gly Leu Ser Ser Ser Ser Gly Ser Glu Gly Phe Gly Cys Asn Asn Asn
            20                  25                  30
```

```
Gly Asn Gly Asn Gly Asn Asn Met Arg Asp Leu Asp Met Asn Gln Pro
            35                  40                  45

Ala Ser Gly Gly Glu Glu Glu Phe Pro Met Gly Ser Val Glu Glu
 50                  55                  60

Glu Glu Asp Glu Arg Gly Gly Ala Gly Gly Arg Gly Pro His Arg Ser
 65                  70                  75                  80

Lys Lys Leu Arg Leu Ser Lys Glu Gln Ser Arg Leu Leu Glu Ser
                 85                  90                  95

Phe Arg Phe Asn His Thr Pro Thr Pro Lys Gln Lys Glu Ala Leu Ala
                100                 105                 110

Gly Lys Leu Gln Leu Arg Pro Arg Gln Val Glu Val Trp Phe Gln Asn
                115                 120                 125

Arg Arg Ala Arg Thr Lys Leu Lys Gln Thr Glu Leu Glu Cys Glu Tyr
130                 135                 140

Leu Lys Arg Cys Phe Gly Ser Leu Thr Glu Glu Asn Arg Arg Leu Gln
145                 150                 155                 160

Arg Glu Val Glu Glu Leu Arg Ala Met Arg Val Ala Pro Pro Thr Val
                165                 170                 175

Leu Ser Pro His Ser Arg Gln Pro Leu Pro Ala Ser Ala Leu Thr Met
                180                 185                 190

Cys Pro Arg Cys Glu Arg Ile Thr Ala Ala Thr Ala Ala Arg Thr Pro
                195                 200                 205

Arg Pro Ala Ala Ala Ala Ala Gly Ser Asn Pro Phe His Pro Arg
210                 215                 220

Arg Pro Ser Ala Ala Phe
225                 230

<210> SEQ ID NO 13
<211> LENGTH: 230
<212> TYPE: PRT
<213> ORGANISM: Vitis vinifera
<220> FEATURE:
<223> OTHER INFORMATION: VvHB17

<400> SEQUENCE: 13

Met Asp Val Ile Pro Met Arg Ser Ser Ser Leu Glu Leu Thr Ile Ser
 1               5                  10                  15

Val Pro Gly Phe Thr Ser Ser Pro Ser Leu Pro Ser Ser Ala Asp Gly
                20                  25                  30

Lys Lys Thr Gly Glu Gly Val Cys Gly Val Arg Asp Leu Asp Ile Asn
            35                  40                  45

Gln Val Pro Leu Gly Ala Glu Glu Trp Thr Thr Gly Ser Met Glu
 50                  55                  60

Asp Glu Glu Glu Ser Gly Asn Gly Gly Pro Arg Lys Lys Leu Arg
 65                  70                  75                  80

Leu Ser Lys Asp Gln Ser Arg Leu Leu Glu Glu Ser Phe Arg Gln Asn
                 85                  90                  95

His Thr Leu Asn Pro Lys Gln Lys Glu Ala Leu Ala Met Gln Leu Lys
                100                 105                 110

Leu Arg Pro Arg Gln Val Glu Val Trp Phe Gln Asn Arg Arg Ala Arg
                115                 120                 125

Ser Lys Leu Lys Gln Thr Glu Met Glu Cys Glu Tyr Leu Lys Arg Trp
130                 135                 140

Phe Gly Ser Leu Thr Glu Gln Asn Arg Arg Leu Gln Arg Glu Val Glu
145                 150                 155                 160
```

Glu Leu Arg Ala Met Lys Val Ala Pro Pro Thr Val Ile Ser Pro His
                165                 170                 175

Ser Cys Glu Pro Leu Pro Ala Ser Thr Leu Thr Met Cys Pro Arg Cys
            180                 185                 190

Glu Arg Val Thr Thr Thr Ser Leu Gly Lys Asp Pro Thr Asn Arg Thr
        195                 200                 205

Thr Ser Pro Thr Leu Ser Ser Lys Leu Pro Thr Ala Leu His Ser Arg
    210                 215                 220

His Ser Ser Ala Ala Cys
225             230

<210> SEQ ID NO 14
<211> LENGTH: 209
<212> TYPE: PRT
<213> ORGANISM: Carica papaya
<220> FEATURE:
<223> OTHER INFORMATION: CpHB17

<400> SEQUENCE: 14

Met Ala Val Leu Pro Thr Asn Ser Ser Leu Glu Leu Thr Ile Ser
1               5                   10                  15

Val Pro Gly Phe Ala Ser Ser Pro Leu Pro Ser Cys Val Lys Glu
                20                  25                  30

Leu Asp Ile Asn Gln Val Pro Ser Gly Glu Glu Trp Thr Ala Gly
            35                  40                  45

Ala Thr Val Glu Glu Glu Glu Ser Ser Asn Gly Gly Pro Pro Arg
        50                  55                  60

Lys Lys Leu Arg Leu Thr Lys Glu Gln Ser Arg Leu Leu Glu Glu Ser
65              70                  75                  80

Phe Arg Gln Asn His Thr Leu Asn Pro Lys Gln Lys Glu Thr Leu Ala
                85                  90                  95

Thr Gln Leu Lys Leu Arg Pro Arg Gln Val Glu Val Trp Phe Gln Asn
            100                 105                 110

Arg Arg Ala Arg Ser Lys Leu Lys Gln Thr Glu Met Glu Cys Glu Tyr
        115                 120                 125

Leu Lys Arg Trp Phe Gly Ser Leu Thr Glu Gln Asn Arg Arg Leu Gln
130                 135                 140

Arg Glu Val Glu Glu Leu Arg Ala Met Lys Val Gly Pro Pro Thr Val
145                 150                 155                 160

Ile Ser Pro His Ser Cys Glu Pro Leu Pro Ala Ser Thr Leu Thr Met
                165                 170                 175

Cys Pro Arg Cys Glu Arg Val Thr Ser Thr Ala Pro Thr Ala Val Leu
            180                 185                 190

Asp Thr Thr Ala Lys Ala Gly Pro Pro Arg Gln Ser Ser Ala Ala
        195                 200                 205

Cys

<210> SEQ ID NO 15
<211> LENGTH: 218
<212> TYPE: PRT
<213> ORGANISM: Populus trichocarpa
<220> FEATURE:
<223> OTHER INFORMATION: PtHB17

<400> SEQUENCE: 15

Met Ala Val Ser Arg Ser Ser Ser Ser Leu Glu Leu Thr Met Ser
1               5                   10                  15

Met Pro Gly Val Cys Ala Val Lys Asp Phe Asp Ile Asn Gln Val Pro
            20                  25                  30

Ser Gly Ala Ala Glu Glu Trp Ile Ser Ala Gly Met Glu Asp Glu
        35                  40                  45

Glu Glu Ser Thr Asp Gly Ala Pro Pro Arg Lys Lys Leu Arg Leu Ser
    50                  55                  60

Lys Glu Gln Ser Arg Leu Leu Glu Glu Ser Phe Arg Gln His His Ser
65                  70                  75                  80

Leu Asn Pro Arg Gln Lys Glu Ala Leu Ala Leu Gln Leu Lys Leu Arg
                85                  90                  95

Pro Arg Gln Val Glu Val Trp Phe Gln Asn Arg Arg Ala Arg Ser Lys
            100                 105                 110

Leu Lys Gln Thr Glu Met Glu Cys Glu Tyr Leu Lys Arg Trp Phe Gly
        115                 120                 125

Ser Leu Thr Glu Gln Asn Arg Arg Leu Gln Arg Glu Val Glu Glu Leu
    130                 135                 140

Arg Ala Leu Lys Val Gly Pro Pro Thr Val Ile Ser Pro His Ser Arg
145                 150                 155                 160

Glu Pro Leu Pro Ala Ser Thr Leu Thr Met Cys Pro Arg Cys Glu Arg
                165                 170                 175

Val Thr Thr Thr Gly Val Asp Lys Gly Ser Thr Lys Thr Thr Arg Thr
            180                 185                 190

Ala Val Ala Asn Pro Thr Ile Ala Ala Thr Leu Ser Ser Glu Asn Gly
        195                 200                 205

Ala Pro Ala Leu Gln Ser Arg Gln Ser Cys
    210                 215

<210> SEQ ID NO 16
<211> LENGTH: 201
<212> TYPE: PRT
<213> ORGANISM: Thellungiella halophila
<220> FEATURE:
<223> OTHER INFORMATION: ThHB17

<400> SEQUENCE: 16

Met Ala Ile Leu Pro Glu Asn Ser Ser Asn Leu Asp Leu Ser Ile Ser
1               5                   10                  15

Val Pro Gly Phe Ser Ser Pro Pro Ser Asp Glu Gly Ser Gly Arg
            20                  25                  30

Gly Arg Glu Gln Leu Lys Leu Asp Met Asn Arg Leu Pro Ser Ser Glu
        35                  40                  45

Glu Asp Glu Glu Phe Ser His Gly Gly Ser Ala Pro Pro Arg Lys Lys
    50                  55                  60

Leu Arg Leu Thr Arg Glu Gln Ser Arg Leu Leu Glu Asp Ser Phe Arg
65                  70                  75                  80

Gln Asn His Thr Leu Asn Pro Lys Gln Lys Glu Ala Leu Ala Lys His
                85                  90                  95

Leu Met Leu Arg Pro Arg Gln Ile Glu Val Trp Phe Gln Asn Arg Arg
            100                 105                 110

Ala Arg Ser Lys Leu Lys Gln Thr Glu Met Glu Cys Glu Tyr Leu Lys
        115                 120                 125

Arg Trp Phe Gly Ser Leu Thr Glu Gln Asn His Arg Leu His Arg Glu
    130                 135                 140

Val Glu Glu Leu Arg Thr Met Lys Val Gly Pro Pro Thr Val Thr Ser
145                 150                 155                 160

```
Thr Ala Ser Leu Thr Met Cys Pro Arg Cys Glu Arg Val Thr Thr Ala
                165                 170                 175

Thr Ser Pro Tyr Val Val Asp Gly Gly Gly Val Leu Ala Lys Lys
            180                 185                 190

Thr Leu Pro Thr Gln Glu Arg Glu His
        195                 200
```

<210> SEQ ID NO 17
<211> LENGTH: 237
<212> TYPE: PRT
<213> ORGANISM: Ricinus communis
<220> FEATURE:
<223> OTHER INFORMATION: RcHB17

<400> SEQUENCE: 17

```
Met Ala Ile Ser Pro Ser Ser Ser Ser Leu Glu Leu Thr Ile Ser
1               5                   10                  15

Met Pro Gly Phe Ala Ser Ser Pro Ser Val Pro Ser Tyr Gly Glu Gly
            20                  25                  30

Val Lys Asp Leu Asp Ile Asn Gln Leu Pro Ala Gly Val Ala Glu Glu
        35                  40                  45

Glu Trp Ile Thr Ala Gly Ile Glu Asp Glu Glu Ser Asn Ile Asn
    50                  55                  60

Gly Gly Pro Pro Arg Lys Lys Leu Arg Leu Ser Lys Glu Gln Ser Arg
65                  70                  75                  80

Leu Leu Glu Glu Ser Phe Arg Gln His His Thr Leu Asn Pro Arg Gln
                85                  90                  95

Lys Glu Ala Leu Ala Met Gln Leu Lys Leu Arg Pro Arg Gln Val Glu
            100                 105                 110

Val Trp Phe Gln Asn Arg Arg Ala Arg Ser Lys Leu Lys Gln Thr Glu
        115                 120                 125

Met Glu Cys Glu Tyr Leu Lys Arg Trp Phe Gly Ser Leu Thr Glu Gln
    130                 135                 140

Asn Arg Arg Leu Gln Arg Glu Val Glu Glu Leu Arg Ala Met Lys Val
145                 150                 155                 160

Gly Pro Pro Thr Val Leu Ser Pro His Ser Cys Glu Pro Leu Pro Ala
                165                 170                 175

Ser Thr Leu Thr Met Cys Pro Arg Cys Glu Arg Val Thr Thr Ser Thr
            180                 185                 190

Asn Thr Ala Ala Ala Phe Asp Lys Gly Pro Thr Arg Thr Ala Thr Pro
        195                 200                 205

Ala Thr Thr Pro Thr Thr Ala Val Ala Thr Leu Ser Ser Lys Val Gly
    210                 215                 220

Thr Pro Thr Leu Gln Ser Arg Gln Ser Ser Ala Ala Cys
225                 230                 235
```

<210> SEQ ID NO 18
<211> LENGTH: 208
<212> TYPE: PRT
<213> ORGANISM: Arabidopsis lyrata
<220> FEATURE:
<223> OTHER INFORMATION: AlHB18

<400> SEQUENCE: 18

```
Met Ala Leu Ser Pro Asn Ser Ser Ser Leu Asp Leu Thr Ile Ser Ile
1               5                   10                  15

Pro Ser Phe Ser Pro Ser Pro Ser Leu Gly Asp His Asp His Gly Val
```

```
                    20                  25                  30
Arg Asp Leu Asp Ile Asn Gln Thr Pro Lys Thr Glu Glu Asp Arg Glu
                35                  40                  45
Trp Ile Met Ile Gly Ala Thr Pro His Val Asn Glu Asp Asp Ser Asn
             50                  55                  60
Pro Gly Gly Arg Arg Lys Lys Leu Arg Leu Thr Lys Glu Gln Ser
 65                  70                  75                  80
His Leu Glu Glu Ser Phe Ile Gln Asn His Thr Leu Thr Pro Lys
                 85                  90                  95
Gln Lys Lys Asp Leu Ala Thr Phe Leu Lys Leu Ser Gln Arg Gln Val
                100                 105                 110
Glu Val Trp Phe Gln Asn Arg Arg Ala Arg Ser Lys Leu Lys His Thr
             115                 120                 125
Glu Met Glu Cys Glu Tyr Leu Lys Arg Trp Phe Gly Ser Leu Lys Glu
             130                 135                 140
Gln Asn Arg Arg Leu Gln Ile Glu Val Glu Glu Leu Arg Ala Leu Lys
145                 150                 155                 160
Pro Ser Ser Thr Ser Ala Leu Thr Met Cys Pro Arg Cys Glu Arg Val
                 165                 170                 175
Thr Asp Ala Ala Asp Asn Asp Ser Asn Ala Val Gln Glu Gly Ala Val
                180                 185                 190
Leu Ser Ser Arg Ser Arg Met Thr Ile Ser Ser Ser Ser Ser Leu Cys
             195                 200                 205
```

<210> SEQ ID NO 19
<211> LENGTH: 201
<212> TYPE: PRT
<213> ORGANISM: Arabidopsis lyrata
<220> FEATURE:
<223> OTHER INFORMATION: AlHB17

<400> SEQUENCE: 19

```
Met Ala Ile Leu Pro Glu Asn Ser Ser Asn Leu Asp Leu Thr Ile Ser
 1               5                  10                  15
Val Pro Gly Phe Ser Ser Pro Pro Ser Asp Glu Gly Ser Gly Gly
             20                  25                  30
Gly Arg Asp Gln Leu Lys Leu Asp Met Asn Arg Leu Pro Ser Ser Glu
                35                  40                  45
Asp Gly Asp Asp Glu Glu Phe Ser His Asp Gly Ser Ala Pro Pro Arg
             50                  55                  60
Lys Lys Leu Arg Leu Thr Arg Glu Gln Ser Arg Leu Leu Glu Asp Ser
 65                  70                  75                  80
Phe Arg Gln Asn His Thr Leu Asn Pro Lys Gln Lys Glu Ala Leu Ala
                 85                  90                  95
Lys His Leu Met Leu Arg Pro Arg Gln Ile Glu Val Trp Phe Gln Asn
                100                 105                 110
Arg Arg Ala Arg Ser Lys Leu Lys Gln Thr Glu Met Glu Cys Glu Tyr
             115                 120                 125
Leu Lys Arg Trp Phe Gly Ser Leu Thr Glu Gln Asn His Arg Leu His
             130                 135                 140
Arg Glu Val Glu Glu Leu Arg Ala Met Lys Val Gly Pro Thr Thr Val
145                 150                 155                 160
Asn Ser Ala Ser Ser Leu Thr Met Cys Pro Arg Cys Glu Arg Val Thr
                 165                 170                 175
Thr Ala Ala Ser Pro Ser Arg Ala Val Val Pro Val Pro Ala Lys Lys
```

Thr Phe Pro Pro Gln Glu Arg Asp His
            195                 200

<210> SEQ ID NO 20
<211> LENGTH: 275
<212> TYPE: PRT
<213> ORGANISM: Arabidopsis thaliana
<220> FEATURE:
<223> OTHER INFORMATION: AtHB17_TAIR

<400> SEQUENCE: 20

Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Arg Asp Gln Leu Arg Leu
            100                 105                 110

Asp Met Asn Arg Leu Pro Ser Ser Glu Asp Gly Asp Glu Glu Phe
        115                 120                 125

Ser His Asp Asp Gly Ser Ala Pro Pro Arg Lys Lys Leu Arg Leu Thr
    130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190

Leu Lys Gln Thr Glu Met Glu Cys Glu Tyr Leu Lys Arg Trp Phe Gly
        195                 200                 205

Ser Leu Thr Glu Glu Asn His Arg Leu His Arg Glu Val Glu Glu Leu
    210                 215                 220

Arg Ala Met Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
        275

<210> SEQ ID NO 21
<211> LENGTH: 275
<212> TYPE: PRT
<213> ORGANISM: Arabidopsis thaliana
<220> FEATURE:
<223> OTHER INFORMATION: AtHB17 EAR mutation variant

<400> SEQUENCE: 21

```
Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
                20                  25                  30

Lys Gly Ile Val Thr Leu Gln Val Cys Leu Phe Tyr Ile Lys Leu Arg
            35                  40                  45

Val Phe Leu Ser Asn Phe Thr Phe Ser Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Ala Asp Ala Thr Ile Ser Val Pro Gly Phe Ser Ser Ser
                85                  90                  95

Pro Leu Ser Asp Glu Gly Ser Gly Gly Arg Asp Gln Leu Arg Leu
            100                 105                 110

Asp Met Asn Arg Leu Pro Ser Ser Glu Asp Gly Asp Glu Glu Phe
            115                 120                 125

Ser His Asp Asp Gly Ser Ala Pro Pro Arg Lys Lys Leu Arg Leu Thr
                130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
                180                 185                 190

Leu Lys Gln Thr Glu Met Glu Cys Glu Tyr Leu Lys Arg Trp Phe Gly
            195                 200                 205

Ser Leu Thr Glu Glu Asn His Arg Leu His Arg Glu Val Glu Glu Leu
    210                 215                 220

Arg Ala Ile Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
                260                 265                 270

Arg Asp Arg
        275

<210> SEQ ID NO 22
<211> LENGTH: 202
<212> TYPE: PRT
<213> ORGANISM: Arabidopsis thaliana
<220> FEATURE:
<223> OTHER INFORMATION: AtHB17_delta1-73

<400> SEQUENCE: 22

Met Ala Ile Leu Pro Glu Asn Ser Ser Asn Leu Asp Leu Thr Ile Ser
1               5                   10                  15

Val Pro Gly Phe Ser Ser Ser Pro Leu Ser Asp Glu Gly Ser Gly Gly
                20                  25                  30

Gly Arg Asp Gln Leu Arg Leu Asp Met Asn Arg Leu Pro Ser Ser Glu
            35                  40                  45

Asp Gly Asp Glu Glu Phe Ser His Asp Asp Gly Ser Ala Pro Pro
    50                  55                  60

Arg Lys Lys Leu Arg Leu Thr Arg Glu Gln Ser Arg Leu Leu Glu Asp
65                  70                  75                  80
```

```
Ser Phe Arg Gln Asn His Thr Leu Asn Pro Lys Gln Lys Glu Val Leu
                 85                  90                  95

Ala Lys His Leu Met Leu Arg Pro Arg Gln Ile Glu Val Trp Phe Gln
            100                 105                 110

Asn Arg Arg Ala Arg Ser Lys Leu Lys Gln Thr Glu Met Glu Cys Glu
            115                 120                 125

Tyr Leu Lys Arg Trp Phe Gly Ser Leu Thr Glu Glu Asn His Arg Leu
130                 135                 140

His Arg Glu Val Glu Glu Leu Arg Ala Ile Lys Val Gly Pro Thr Thr
145                 150                 155                 160

Val Asn Ser Ala Ser Ser Leu Thr Met Cys Pro Arg Cys Glu Arg Val
                165                 170                 175

Thr Pro Ala Ala Ser Pro Ser Arg Ala Val Val Pro Val Pro Ala Lys
            180                 185                 190

Lys Thr Phe Pro Pro Gln Glu Arg Asp Arg
            195                 200

<210> SEQ ID NO 23
<211> LENGTH: 202
<212> TYPE: PRT
<213> ORGANISM: Arabidopsis thaliana
<220> FEATURE:
<223> OTHER INFORMATION: AtHB17_delta1-73_L84A_L86A

<400> SEQUENCE: 23

Met Ala Ile Leu Pro Glu Asn Ser Ser Asn Ala Asp Ala Thr Ile Ser
1               5                   10                  15

Val Pro Gly Phe Ser Ser Pro Leu Ser Asp Glu Gly Ser Gly Gly
            20                  25                  30

Gly Arg Asp Gln Leu Arg Leu Asp Met Asn Arg Leu Pro Ser Ser Glu
        35                  40                  45

Asp Gly Asp Asp Glu Glu Phe Ser His Asp Asp Gly Ser Ala Pro Pro
    50                  55                  60

Arg Lys Lys Leu Arg Leu Thr Arg Glu Gln Ser Arg Leu Leu Glu Asp
65                  70                  75                  80

Ser Phe Arg Gln Asn His Thr Leu Asn Pro Lys Gln Lys Glu Val Leu
                85                  90                  95

Ala Lys His Leu Met Leu Arg Pro Arg Gln Ile Glu Val Trp Phe Gln
            100                 105                 110

Asn Arg Arg Ala Arg Ser Lys Leu Lys Gln Thr Glu Met Glu Cys Glu
            115                 120                 125

Tyr Leu Lys Arg Trp Phe Gly Ser Leu Thr Glu Glu Asn His Arg Leu
130                 135                 140

His Arg Glu Val Glu Glu Leu Arg Ala Ile Lys Val Gly Pro Thr Thr
145                 150                 155                 160

Val Asn Ser Ala Ser Ser Leu Thr Met Cys Pro Arg Cys Glu Arg Val
                165                 170                 175

Thr Pro Ala Ala Ser Pro Ser Arg Ala Val Val Pro Val Pro Ala Lys
            180                 185                 190

Lys Thr Phe Pro Pro Gln Glu Arg Asp Arg
            195                 200

<210> SEQ ID NO 24
<211> LENGTH: 219
<212> TYPE: PRT
<213> ORGANISM: Escherichia coli
<220> FEATURE:
```

-continued

<223> OTHER INFORMATION: CAT

<400> SEQUENCE: 24

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Leu Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 25
<211> LENGTH: 828
<212> TYPE: DNA
<213> ORGANISM: Arabidopsis thaliana
<220> FEATURE:
<223> OTHER INFORMATION: AtHB17

<400> SEQUENCE: 25
atgataaaac tactatttac gtacatatgc acatacacat ataaactata tgctctatat      60
catatggatt acgcatgcgt gtgtatgtat aaatataaag gcatcgtcac gcttcaagtt     120
tgtctctttt atattaaact gagagttttc ctctcaaact ttaccttttc ttcttcgatc     180
ctagctctta agaaccctaa taattcattg atcaaaataa tggcgatttt gccggaaaac     240
tcttcaaact tggatcttac tatctccgtt ccaggcttct cttcatcccc tctctccgat     300
gaaggaagtg gcggaggaag agaccagcta aggctagaca tgaatcggtt accgtcgtct     360
gaagacggag acgatgaaga attcagtcac gatgatggct ctgctcctcc gcgaaagaaa     420
ctccgtctaa ccagagaaca gtcacgtctt cttgaagata gtttcagaca gaatcatacc     480
cttaatccca acaaaagga agtacttgcc aagcatttga tgctacggcc aagacaaatt     540
gaagtttggt ttcaaaaccg tagagcaagg agcaaattga agcaaaccga gatggaatgc     600
gagtatctca aaaggtggtt tggttcatta acggaagaaa accacaggct ccatagaaaa     660
gtagaagagc ttagagccat aaaggttggc ccaacaacgg tgaactctgc ctcgagcctt     720

```
actatgtgtc tcgctgcga gcgagttacc cctgccgcga gcccttcgag ggcggtggtg    780
ccggttccgg ctaagaaaac gtttccgccg caagagcgtg atcgttga               828
```

<210> SEQ ID NO 26
<211> LENGTH: 1096
<212> TYPE: DNA
<213> ORGANISM: Glycine max
<220> FEATURE:
<223> OTHER INFORMATION: G3524

<400> SEQUENCE: 26

```
tgcttcttct gtcttccttt tcatgtgtgt ctccttctgt ttctccactt tacctttttt     60
ctctcctttt tgttgatccc cctcttcctc ttcttcatct cacatcattt ttttcttcat    120
cccttttcatt gttttctgtg tgttttctat ggcggtttta ccaagtagct cctcaagctt   180
ggaattgacc atatctgtac ctggttttgc ttcttcacca acccttcttc cctcatcatc    240
tgtgaaagaa ttggacataa atcaagtacc tcttgaagaa gattggatgg catcaaacat    300
ggaagatgaa gaagaaagca gcaatggaga acctcctcga agaaactcc gtctcacaaa     360
ggaacaatct cgtctccttg aagaaagctt tagacaaaac cacacgttga acccaaagca    420
gaaagagtct ttggcaatgc aactgaagct gcgaccaagg caagtggagg tgtggtttca    480
gaaccgtagg gccaggagca agctgaagca gacagagatg gagtgcgagt acctcaagag    540
gtggttcggt tccctcacag agcagaaccg gaggctccag agggaagtgg aggagctgcg    600
agccattaag gtgggcccac ccaccgtgat ctcccctcac tcctgcgaac cgctcccggc    660
ctccacactt tccatgtgtc cccgctgcga gcgtgtcacc tccaccgccg acaaaccgcc    720
ctccgccgcg ccactttgt ccgctaaagt gccgccaact caatcccgcc aaccctccgc    780
ggcctgttga ccctataact atagtccatc gcctactctg cacgccacct ctactacctc    840
atcatctaat taatcagaaa cagggcacaa acttaactaa actttacaaa actaaaaagt    900
tagtgtgaat gaagatataa tatgtgttag aaaaaataat gttttttttt tttttttac    960
taaaagggcg ttttcggata gggaaacttt tgtagttagt agtagtactt tcaatggtca   1020
atgcgtatct gattattggg ctttcatatt gactttctcc tttttcaaat atggatagaa   1080
cttttattta aaaaaa                                                  1096
```

<210> SEQ ID NO 27
<211> LENGTH: 1174
<212> TYPE: DNA
<213> ORGANISM: Oryza sativa
<220> FEATURE:
<223> OTHER INFORMATION: G3510

<400> SEQUENCE: 27

```
tctccctccg cctttgcccc gccttccctg ccctttttctc ttgctgagcc gcttctgcat     60
tggcttgtga tgatgggggc cacttctccg tcaggcctgg agctcaccat ggctgtcccc    120
ggcctcagct cctctggttc agaaggggcc ggttgcaaca caacaacgc cggtggcggc     180
tgcaacatga gggacctgga catcaaccag ccggcgagcg gcggcgagga ggaggagttc    240
ccgatgggca cgtggagga ggacgaggag gagaggggcg tcgtgtgggcc ccaccgcccc    300
aagaagctcc gcctctccaa ggagcagtcc cgcctcctcg aggagagctt ccgcctcaac    360
cataccctca cgccgaagca aaaggaggcc ttggcgatca aactgaagct gcggccgagg    420
caggtggagg tctggtttca gaaccgtagg gcaaggacga agctgaagca gacggagatg    480
```

```
gagtgcgagt acctgaagcg ctgcttcggg tcgctgacgg aggagaaccg ccggctgcag    540
cgggaggtgg aggagctgcg ggcgatgcgg gtggccccgc ccacggtgct ctcgccgcac    600
accaggcagc cgctcccggc gtccgcgctc accatgtgcc cccgctgcga gcgcatcacc    660
gccgccaccg gcccgcctgc cgtgcgcccg ccgccgtcgt cagccgccgc cgccgccccc    720
tcgcccttcc accctcgccg cccctctgcg gccttctagg cccaaggtct cgcatcctaa    780
aggccacaaa aagatgggcc tcgccgtccc gtgtaaattg aaggagacga cgcagcggta    840
gagggccccg tgtcggcgtt gttgcgtcgg gtccagtcgt ctcagaggag tcagaggcgt    900
ggacaaaatg tttgttgcgg tgtttgtgtt ccattggtcg ttgatcttag cttgatgatc    960
tgtgattcgc gccttgctcg tctaggtttc tcttgggccg acgcatgatc ttttttcccc   1020
cgtgtcggac cttattgggc cttttgagat cgacgggccc cctccttgtt tcgcatgtgg   1080
acatgttatt tcgtcctttt gggccaacaa ttcagcacgg tggccaacgg tgcgtagttc   1140
gtcgccgttt tctttcaaaa aaaaaaaaaa aaaa                               1174

<210> SEQ ID NO 28
<211> LENGTH: 642
<212> TYPE: DNA
<213> ORGANISM: Glycine max
<220> FEATURE:
<223> OTHER INFORMATION: G4371

<400> SEQUENCE: 28
atggcggttt taccaagtag ctcctcaagc ttggaattga ccatatctgt acctggtttt     60
gcttcttcac caacccttct tccctcatca tctgtgaaag aattggacat aaatcaagta    120
cctcttgaag aagattggat ggcatcaaac atggaagatg aagaagaaag cagcaatgga    180
gaacctcctc gaaagaaact ccgtctcaca aaggaacaat ctcttctcct tgaagaaagc    240
tttagacaaa accacacgtt gaacccaaag cagaaagagt ctttggcaat gcaactgaag    300 ctgccgaccaa gcaagtgga ggtgtggttt cagaaccgta gggccaggag caagctgaag    360
cagacagaga tggagtgcga gtacctcaag aggtggttcg gttccctcac agagcagaac    420
cggaggctcc agagggaagt ggaggagctg cgagccatta aggtgggccc acccaccgtg    480
atctcccctc actcctgcga accgctcccg gcctccacac tttccatgtg tccccgctgc    540
gagcgtgtca cctccaccgc cgacaaaccg ccctccgccg cggccacttt gtccgctaaa    600
gtgccgccaa ctcaatcccg ccaaccctcc gcggcctgtt ag                      642

<210> SEQ ID NO 29
<211> LENGTH: 678
<212> TYPE: DNA
<213> ORGANISM: zea mays
<220> FEATURE:
<223> OTHER INFORMATION: G4369

<400> SEQUENCE: 29
atggggtcca cttctccttc aggcctggag ctcaccatgg ctgtcccggg cctcagctcc     60
tcctctggct cagaggggtt tggatgcaac aacaacaacg ggagcgggaa cgggaacaac    120
atgagggacc tggacatgaa ccagccggcg agcggcggcg aggaggagga gttcccaatg    180
gggagcgtgg aggaggagga ggacgagcgc ggcggcgccg gcgggccgca ccgcgccaag    240
aagctccggc tgtccaagga gcagtcccgc ctcctggagg agagcttccg cctcaaccac    300
accctcacac cgaagcaaaa ggaggccttg gctgtcaagc tcaagctgcg gcccaggcag    360
gtggaggtct ggttccagaa ccgcagggct aggacgaagc ttaagcagac ggagctggag    420
```

```
tgcgagtacc tgaagcgctg cttcggctcg ctgaccgagg agaaccggcg gctgcagcgg      480
gaggtggagg agctgcgcgc gatgcgggtg gccccgccca ccgtgctctc cccgcacacc      540
cggcagccgc tcccggcgtc cgcgctcacc atgtgcccgc gctgcgagcg catcaccgcc      600
gcaacggccg cgcgcacccc acgcccgccg cccgccgcga gccccttcca cccgcgccgc      660
ccgtccgcgg cgttttag                                                    678

<210> SEQ ID NO 30
<211> LENGTH: 669
<212> TYPE: DNA
<213> ORGANISM: zea mays
<220> FEATURE:
<223> OTHER INFORMATION: G4370

<400> SEQUENCE: 30
atgggggcca cttctccttc aggcctggag ctcaccatgg ctgtcccegg cctcagctcc      60 tcctctggct cagaggggtt tgtttgcaac aacaatatca gcaacaacgg tggcgggaac     120
atgagggacc tggacatgaa ccagccggcg agcggcggcg aggaggagga tttcctgatg     180
ggcggcgtgg aagaggacga ggaggagcgg ggcgccggcg daccgcaccg cccaaagaag     240
ctccgcctct ccaaggagca gtcccgcctc ctcgaggaga gcttccgcct caaccacacc     300
ctctcaccga gcaaaagga ggccttggcg atcaaactga agctgcggcc caggcaggtg     360
gaggtctggt ttcagaaccg cagggcaagg actaagctga agcacacgga gatggagtgc     420
gagtacctga aacgctgctt cggctcgctg acggaggaga accgccgcct gcagcgggag     480
gtggaggagc tgagggcgat gcgcatggcg ccgcccacgg tgctctcgcc gcacacacgc     540
cagccactcc cggcgtccgc gctcaccatg tgccccccgct gcgagcgcgt caccgctgcc     600
acctgcccgc ggatcacccg cccggccgcc tcgccgttcc accctcgccg ccctcagcg     660 gcgttttag                                                              669

<210> SEQ ID NO 31
<211> LENGTH: 621
<212> TYPE: DNA
<213> ORGANISM: Arabidopsis thaliana
<220> FEATURE:
<223> OTHER INFORMATION: G2712

<400> SEQUENCE: 31
atggccctct cacctaattc aagctcttta gatttaacaa tctcaattcc gagcttctct      60
ccatctcctt cacttggtga tcatcacggg atgagagatt ttgacataaa ccaaacacca     120
aagacggaag aagatcgtga gtggatgatc ggtgcaacac cacatgtcaa cgaagatgat     180
agcaactcgg gtggccggcg gcgcaaaaag ctccgtctaa cgaaagaaca atcacatctt     240
cttgaagaga gtttcataca aaaccatacc ttaacccccta agcaaaaaaa agatttggcc     300 accttttttga agcttagtca aaggcaagtt gaggtgtggt ttcaaaatcg aagagctcgg     360
agtaagctaa agcacacgga aatggaatgt gagtatctaa aaagatggtt cggatcgttg     420
aaggaacaaa atcgacggct acaaatagaa gttgaagaac tacgagcgct aaagccatca     480
tcgacctcgg ctttaaccat gtgtcctcgg tgtgaacgtg tgactgatgc agtagataat     540
gactctaatg ccgttcaaga gggggcagtt cttagcagcc ggtcacggat gacaatttcc     600
tcttcctctt ccctctgttg a                                                621

<210> SEQ ID NO 32
```

```
<211> LENGTH: 855
<212> TYPE: DNA
<213> ORGANISM: Arabidopsis thaliana
<220> FEATURE:
<223> OTHER INFORMATION: G400

<400> SEQUENCE: 32
atgatgttcg agaaagacga tctgggtcta agcttaggct tgaattttcc aaagaaacag      60
atcaatctca aatcaaatcc atctgtttct gttactcctt cttcttcttc ttttggatta     120
ttcagaagat cttcatggaa cgagagtttt acttcttcag ttccaaactc agattcgtca     180
caaaaagaaa caagaacttt catccgagga atcgacgtga acagaccacc gtctacagcg     240
gaatacggcg acgaagacgc tggagtatct tcacctaaca gtacagtctc aagctctaca     300
gggaaaagaa gcgagagaga agaagacaca gatccacaag gctcaagagg aatcagtgac     360
gatgaagatg gtgataactc caggaaaaag cttagacttt ccaaagatca atctgctatt     420
cttgaagaga ccttcaaaga tcacagtact ctcaatccga agcagaagca agcattggct     480
aaacaattag ggttacgagc aagacaagtg gaagtttggt ttcagaacag acgagcaaga     540
acaaagctga agcaaacgga ggtagactgc gagttcttac ggagatgctg cgagaatcta     600
acggaagaga accgtcggct acaaaaagaa gtaacgaat tgagagcact taagctctct     660
cctcagttct acatgcacat gagcccaccc actactttga ccatgtgccc ttcatgtgaa     720
cacgtgtcgg tcccgccacc acaacctcag gctgctacgt cagcgcacca ccggtcgttg     780
ccggtcaatg cgtgggctcc tgcgacgagg atatctcacg gcttgacttt tgacgctctt     840
cgtcctaggt cctaa                                                      855

<210> SEQ ID NO 33
<211> LENGTH: 977
<212> TYPE: DNA
<213> ORGANISM: Arabidopsis thaliana
<220> FEATURE:
<223> OTHER INFORMATION: G399

<400> SEQUENCE: 33
aggaaataaa aaacatgatg atgggcaaag aagatctagg tttgagccta agcttagggt      60
tttcacaaaa tcacaatcct cttcagatga atctgaatcc taactcttca ttatcaaaca     120
atctccagag actcccatgg aaccaaacat tcgatcctac atcagatctt cgcaagatag     180
acgtgaacag ttttccatca acggttaact gcgaggaaga cacaggagtt tcgtcaccaa     240
acagtacgat ctcaagcacc attagcggga agagaagtga gagagaagga atctccggaa     300
ccggcgttgg ctccggcgac gatcacgacg agatcactcc ggatcgaggg tactcacgtg     360
gaacctcaga tgaagaagaa gacgggggcg aaacgtcgag gaagaagctc aggttatcaa     420
aagatcagtc tgcttttctc gaagagactt tcaaagaaca caacactctc aatcccaaac     480
agaagctagc tttggctaag aagctgaact tgacggcaag acaagtggaa gtgtggttcc     540
aaaacagaag agctagaacc aagttaaagc aaacggaggt agattgcgaa tacttgaaac     600
ggtgcgtaga gaagctaacg gaagagaacc ggagacttca gaaagaggct atggagcttc     660
gaactctcaa gctgtctcca caattctacg gtcagatgac tccaccaact acactcatca     720
tgtgtccttc gtgcgagcgt gtgggtggcc catcatcatc gaaccatcac cacaatcaca     780
ggcccgtttc tatcaatccg tgggttgctt gtgctggtca ggtggctcat gggctgaatt     840
ttgaagccct tgcgtccacga tcgtgatttt ttattttagt ggtgggaaaa gggtgttttg     900 gtattttttcg ttatcgttat atagtctatc tgtgtggggt cattgttatt ttggatgatt     960
```
ggccttctca tgaacta                                                    977

<210> SEQ ID NO 34
<211> LENGTH: 1201
<212> TYPE: DNA
<213> ORGANISM: Arabidopsis thaliana
<220> FEATURE:
<223> OTHER INFORMATION: G398

<400> SEQUENCE: 34
agaaggtttc tcttgtcctc catacactta gcacaactga taaatctttt gaggtaaaat     60
cagctttaga tcaaggtttt tctagtcatc tctactcata aagatcaaag cttttgctat    120
tctcattttc taccaagaga caatatcatg atgatgggta agaggatttt gggtttaagt    180
cttagcttgg gatttgcaca aaaccatcct ctccagctaa atcttaaacc cacttcttca    240
ccaatgtcca atctccagat gtttccatgg aaccaaaccc ttgtttcttc ctcagatcaa    300
caaaagcaac agtttcttag gaaaatcgac gtgaacagct tgccaacaac ggtggatttg    360
gaagaggaga caggagtttc gtctccaaac agtacgatct cgagcacagt gagtggaaag    420
aggaggagta ctgaaagaga aggtacctcc ggtggtggtt gcggagatga ccttgacatc    480
actctagata gatcttcctc acgtggaacc tccgatgaag aggaagatta cggaggtgag    540
acttgtagga agaagcttag actatccaaa gatcaatccg cagttctcga agacactttc    600
aaagagcaca atactctcaa tcccaaacag aagctggctt ggctaagaa gctaggttta    660
acagcaagac aagtggaagt gtggttccaa aacagaagag caaggacaaa gttaaagcag    720
accgaagtgg attgcgagta tttgaaaaga tgtgttgaga aattaacgga agagaatcgg    780
cggctcgaga aagaggcagc ggaactaaga gcattaaagc tttcaccgcg gttgtatggt    840
cagatgagtc caccgaccac acttttgatg tgtccatcgt gtgaacgtgt ggccggacca    900
tcctcatcta accacaacca gcgatctgtc tcattgagtc catggctcca aatggcccat    960
gggtcaacct ttgatgtgat gcgtcctagg tcttaacttt aatgctgctt ctatgggttg   1020
tgtgtgggtc attgtacttt ttagattatt gactctcagc taatgtatcc ttaaaagcct   1080
ttttctactt ttaaatttac tttaatctaa ttaaattagt tgtccatgtc ttcttgataa   1140
caaaaaaatt tataattata aaaaaaaaaa acaggataaa aaaaaaaaaa aaaaaaaaa    1200
a                                                                   1201

<210> SEQ ID NO 35
<211> LENGTH: 693
<212> TYPE: DNA
<213> ORGANISM: Sorghum bicolor
<220> FEATURE:
<223> OTHER INFORMATION: SbHB17

<400> SEQUENCE: 35
atggggtcca cttctccttc aggcctggag ctcaccatgg ctgtcccgg cctcagctcc      60
tcctctggct cagaggggtt tggatgcaac aacaacggga acgggaacgg aacaacatg     120
agggacctgg acatgaacca gccggcgagc ggcggcgagg aggaggagtt cccaatggga    180
agcgtggaga aggaggaaga cgagcgcggc ggcgccggcg ggcgcgggcc gcaccgctcc    240
aagaagctcc gcctctccaa ggagcagtcc cgcctgctgg aggagagctt ccgcttcaac    300
cacacccccca caccgaagca aaagagagcc ttggctggca agctccagct gcggcccagg    360
caggtggagg tctggttcca gaaccgcagg gctaggacga agctgaagca gacggagctg    420

```
gagtgcgagt acctgaagcg gtgcttcggc tcgctgaccg aggagaaccg gcggctgcag      480
cgggaggtgg aggagctgcg cgcgatgcgg gtggccccgc ccaccgtgct ctccccgcac      540
tcccggcagc cgctcccggc atccgcgctc accatgtgcc cgcgctgcga gcgcatcacc      600
gccgcgaccg ccgcgcgtac gcctcgcccg gccgcagccg cagccgcggg cagcaacccc      660
ttccacccgc gccgcccgtc cgcggcgttt tag                                   693

<210> SEQ ID NO 36
<211> LENGTH: 681
<212> TYPE: DNA
<213> ORGANISM: Vitis vinifera
<220> FEATURE:
<223> OTHER INFORMATION: VvHB17

<400> SEQUENCE: 36
atggatgtta tacctatgcg gtcttccagc ttggagctaa ccatatccgt acctggattc       60
acttcatctc cttctcttcc ttcatcggca ggagaagggg tttgtggggt gagagatttg      120
gacataaacc aagtaccgtt gggagcagaa gaagaatgga cgactggaag catggaagac      180
gaagaggaga gtggaaatgg aggtcctcct cgcaagaaac ttcgactctc aaaggaccag      240
tctcgtctcc ttgaagaaag cttcagacaa aaccacacct taaacccctaa acagaaagag      300 gctttggcaa tgcaattgaa gctcagacca agacaagttg aggtctggtt tcaaaaccgt      360
agagccagga gcaagctgaa gcagactgag atggaatgtg aatacttgaa gagatggttc      420
gggtcactga cggagcagaa caggaggcta cagagggaag tggaggagct gagggccatg      480
aaggttgccc cgccaaccgt catctcaccc cacagctgcg agcctcttcc cgcttgccac      540
gctcactatg tgccctcgct gcgagcgcgt gcaccascac ctcgactcgg caaggacccc      600
accaatcgca ccacctcgcc cacccctgtcc tccaaactcc ccaccgccct ccattcccga      660
cactcttcgg cggcttgctg a                                                681

<210> SEQ ID NO 37
<211> LENGTH: 630
<212> TYPE: DNA
<213> ORGANISM: Carica papaya
<220> FEATURE:
<223> OTHER INFORMATION: CpHB17

<400> SEQUENCE: 37
atggcggttt tacccacaaa ttcatcaagc ctggagctca caatatctgt tcctgggttc       60
gcttcatctc ctcctctccc ttcgtgtgtg aaagagttgg acataaacca agtgccgtcg      120
ggagaagagg aatggaccgc tggtgcaacc gtggaagaag aagaagaaag cagcaatgga      180
gggcctccgc gcaagaaact ccgtctcacc aaagagcagt ctcgtcttct tgaagaaagc      240
ttcagacaaa accataccct aaatcctaag caaaagagaa cacttgcaac gcagttgaag      300
ctaaggccga ggcaagttga ggtgtggttt caaaatcgaa gggccaggag caaactgaaa      360
caaaccgaga tggaatgcga gtacctgaag aggtggttcg ggtcgctgac tgagcagaac      420
cggaggctac aaagagaggt ggaggagctg agggccatga aggttgggcc acccaccgtc      480
atttctcccc acagctgcga gcccctcccg gcttccactc tcacgatgtg cccacgttgc      540
gagcgtgtta cctccaccgc tcccaccgct gtacttgaca ccaccgccaa agcaggacct      600
ccaagacaat cctcctctgc ggcttgttag                                       630

<210> SEQ ID NO 38
<211> LENGTH: 657
```

<212> TYPE: DNA
<213> ORGANISM: Populus trichocarpa
<220> FEATURE:
<223> OTHER INFORMATION: PtHB17

<400> SEQUENCE: 38

```
atggccgttt cacgctcaag ctcttctagc ttggagctga ccatgtccat gcctggggtt    60
tgcgcagtga aagatttcga cataaaccaa gtaccatcag gagcagcaga agaagaatgg   120
atctctgcag gcatggagga tgaagaggaa agcactgatg gagccccacc tcgcaaaaaa   180
ctccgtctct ctaaagaaca gtctcgcctt cttgaagaaa gtttcaggca acatcactcc   240
ttgaatccca gacagaaaga agcattagct ttgcagttga agctgaggcc tagacaagtt   300
gaggtgtggt ttcaaaaccg cagggccagg agcaaactta agcagacaga gatggagtgc   360
gagtacttga agagatggtt tggttcatta acagagcaga acaggaggct gcaaagagaa   420
gtagaagagc ttagggcatt aaaggtgggt ccaccaaccg tgatatctcc tcacagtcgt   480
gaacctctcc cagcatccac gcttacaatg tgtccgcgtt gtgaacgtgt gacaaccacc   540
ggcgtggaca agggctccac caaaaccaca cgtactgctg tggccaaccc aacaatagcc   600
gccaccttgt cctctgaaaa tggagcaccc gcactccaat tcggcaatc ttgctag      657
```

<210> SEQ ID NO 39
<211> LENGTH: 606
<212> TYPE: DNA
<213> ORGANISM: Thellungiella halophila
<220> FEATURE:
<223> OTHER INFORMATION: ThHB17

<400> SEQUENCE: 39

```
atggcgattt taccggaaaa actcttcaaac ttagatctttt ctatctccgt tccaggcttc    60
tcttcctctc ctccctccga tgaaggaagt ggcagaggaa gagaacagct aaagcttgac   120
atgaatcgat tgccgtcgtc tgaagaagat gaagaattca gtcacggtgg ctctgctcct   180
ccgcgcaaga aactccgtct cactagagaa cagtctcgtc ttcttgaaga tagtttcaga   240
cagaatcaca cccttaatcc caaacaaaag gaagcacttg caaagcattt gatgctacgg   300
ccaagacaaa ttgaagtatg gttccaaaac cgtagagcaa ggagcaaatt gaagcaaacg   360
gagatggaat gcgagtatct aaaaggtgg tttggttcat taaccgagca aaaccacagg   420
ctccatagag aagtagaaga gcttagaacc atgaaagtag gtccacctac cgtgacctcc   480
accgcgagcc tcaccatgtg tcctcgctgc gagcgagtca ccactgcaac gagcccgtac   540
gtcgtcgatg gcggcggtgg cgttcttgcc aagaaaacgc ttccgacgca agagcgtgag   600
cattga                                                              606
```

<210> SEQ ID NO 40
<211> LENGTH: 714
<212> TYPE: DNA
<213> ORGANISM: Ricinus communis
<220> FEATURE:
<223> OTHER INFORMATION: RcHB17

<400> SEQUENCE: 40

```
atggctattt ctcccagtag ctcttctagc ctggagttga ctatatccat gcctggcttt    60
gcttcttctc cttctgttcc ttcttatggt gaaggagtta agatttgga cataaaccaa   120
ctaccggcag gagtagcaga agaagaatgg atcaccgctg aatagaaga tgaagaggaa   180
agtaatatta acggaggtcc tcctcgtaaa aagctccgtc tttccaaaga gcaatctcgc   240
```

```
cttcttgaag aaagtttcag gcaacaccat actttaaacc caaggcagaa agaagcattg    300
gctatgcagt tgaagctgag gcctagacaa gttgaggtgt ggtttcaaaa ccgtagggcc    360
aggagcaagc ttaagcagac agagatggaa tgcgagtatt taagaggtg gtttggatca     420 ttgacggagc aaaacagaag gctacaaagg gaagtagagg agcttagggc aatgaaagtg    480
ggtccaccaa ctgtattatc acctcacagt tgtgaacctc ttccagcatc aactctcact    540
atgtgtccac ggtgtgaacg tgtgacaacc agcaccaaca ccgccgcagc cttcgacaag    600
ggccccacca gaaccgccac ccctgccacc accctacaa ccgcagtcgc caccttgtcc     660
tctaaagttg ggacaccaac cctccaatct cgtcaatctt ccgcagcttg ttag          714
```

```
<210> SEQ ID NO 41
<211> LENGTH: 627
<212> TYPE: DNA
<213> ORGANISM: Arabidopsis lyrata
<220> FEATURE:
<223> OTHER INFORMATION: AlHB18

<400> SEQUENCE: 41
atggccctct cacctaattc aagctctta gatttaacaa tatcaattcc gagtttttct      60
ccatctcctt cacttggtga tcatgatcac ggggtgagag atttggacat aaaccaaact    120
ccaaagacgg aagaagatcg tgagtggatc atgatcggtg caacaccaca tgtcaacgaa    180
gatgatagca ccccggtgg ccggcggcgc aaaaagctcc gtctaaccaa agagcaatca     240
catcttcttg aagagagttt catacaaaac cataccttaa cccctaagca aaaaaaagat    300
ttagccacct ttttgaagct tagtcaaagg caagttgagg tgtggtttca aaatcgaaga    360
gctcggagta agctaaagca cacggagatg aatgtgagt atctaaaaag atggttcgga     420
tcgttgaagg agcaaaatcg acggctacaa atagaagttg aagaactaag agctctaaag    480
ccatcatcga cctcggcttt aaccatgtgt cctcggtgtg aacgtgtgac tgatgcagca    540
gataatgact ctaatgccgt tcaagagggt gcagttctaa gcagccggtc acggatgaca    600
attctctctt cctcttctct ctgttga                                        627
```

```
<210> SEQ ID NO 42
<211> LENGTH: 606
<212> TYPE: DNA
<213> ORGANISM: Arabidopsis lyrata
<220> FEATURE:
<223> OTHER INFORMATION: AlHB17

<400> SEQUENCE: 42
atggcgattt tacccgaaaa ctcttcaaac ttggatctta ctatctccgt tccaggcttc      60
tcttcctccc ctccctccga tgaaggaagt ggcggaggaa gagaccagct aaagctagac    120
atgaatcgat tgccgtcgtc tgaagacgga gacgatgaag aattcagtca cgatggctct    180
gctcctccgc gaaagaaact tcgtctaacc agagaacagt cacgtcttct tgaagatagt    240
ttcagacaga atcatacccct taatcccaaa caaaaggaag cacttgccaa gcatttgatg    300
ctacggccaa gacaaattga agttggttt caaaaccgta gagcaaggag caaattgaag    360
caaaccgaga tggaatgcga gtacctcaaa aggtggttg gttcattaac ggagcaaaac    420
cacaggctcc atagagaagt agaagagctt agagccatga aggttggccc aacaacagtg    480
aactctgcct cgagcctcac tatgtgtccc cgctgcgagc gagttaccac tgcagcgagc    540
ccttcgaggg cggtggtgcc ggttccggcc aagaaaacgt ttccgccgca agagcgtgat    600
cattga                                                                606
```

<210> SEQ ID NO 43
<211> LENGTH: 828
<212> TYPE: DNA
<213> ORGANISM: Arabidopsis thaliana
<220> FEATURE:
<223> OTHER INFORMATION: AtHB17_TAIR

<400> SEQUENCE: 43

| | |
|---|---|
| atgataaaac tactatttac gtacatatgc acatacacat ataaactata tgctctatat | 60 |
| catatggatt acgcatgcgt gtgtatgtat aaatataaag gcatcgtcac gcttcaagtt | 120 |
| tgtctctttt atattaaact gagagttttc ctctcaaact ttacctttc ttcttcgatc | 180 |
| ctagctctta agaaccctaa taattcattg atcaaaataa tggcgatttt gccggaaaac | 240 |
| tcttcaaact tggatcttac tatctccgtt ccaggcttct cttcatcccc tctctccgat | 300 |
| gaaggaagtg gcggaggaag agaccagcta aggctagaca tgaatcggtt accgtcgtct | 360 |
| gaagacggag acgatgaaga attcagtcac gatgatggc ctgctcctcc gcgaaagaaa | 420 |
| ctccgtctaa ccagagaaca gtcacgtctt cttgaagata gtttcagaca gaatcatacc | 480 |
| cttaatccca aacaaaagga agtacttgcc aagcatttga tgctacggcc aagacaaatt | 540 |
| gaagtttggt ttcaaaaccg tagagcaagg agcaaattga agcaaaccga gatggaatgc | 600 |
| gagtatctca aaaggtggtt tggttcatta acggaagaaa accacaggct ccatagagaa | 660 |
| gtagaagagc ttagagccat gaaggttggc ccaacaacgg tgaactctgc ctcgagcctt | 720 |
| actatgtgtc ctcgctgcga gcgagttacc cctgccgcga gccttcgag ggcggtggtg | 780 |
| ccggttccgg ctaagaaaac gtttccgccg caagagcgtg atcgttga | 828 |

<210> SEQ ID NO 44
<211> LENGTH: 828
<212> TYPE: DNA
<213> ORGANISM: Arabidopsis thaliana
<220> FEATURE:
<223> OTHER INFORMATION: AR mutation variant of AtHB17

<400> SEQUENCE: 44

| | |
|---|---|
| atgataaaac tactatttac gtacatatgc acatacacat ataaactata tgctctatat | 60 |
| catatggatt acgcatgcgt gtgtatgtat aaatataaag gcatcgtcac gcttcaagtt | 120 |
| tgtctctttt atattaaact gagagttttc ctctcaaact ttacctttc ttcttcgatc | 180 |
| ctagctctta agaaccctaa taattcattg atcaaaataa tggcgatttt gccggaaaac | 240 |
| tcttcaaacg ctgatgctac tatctccgtt ccaggcttct cttcatcccc tctctccgat | 300 |
| gaaggaagtg gcggaggaag agaccagcta aggctagaca tgaatcggtt accgtcgtct | 360 |
| gaagacggag acgatgaaga attcagtcac gatgatggc ctgctcctcc gcgaaagaaa | 420 |
| ctccgtctaa ccagagaaca gtcacgtctt cttgaagata gtttcagaca gaatcatacc | 480 |
| cttaatccca aacaaaagga agtacttgcc aagcatttga tgctacggcc aagacaaatt | 540 |
| gaagtttggt ttcaaaaccg tagagcaagg agcaaattga agcaaaccga gatggaatgc | 600 |
| gagtatctca aaaggtggtt tggttcatta acggaagaaa accacaggct ccatagagaa | 660 |
| gtagaagagc ttagagccat aaaggttggc ccaacaacgg tgaactctgc ctcgagcctt | 720 |
| actatgtgtc ctcgctgcga gcgagttacc cctgccgcga gccttcgag ggcggtggtg | 780 |
| ccggttccgg ctaagaaaac gtttccgccg caagagcgtg atcgttga | 828 |

<210> SEQ ID NO 45

```
<211> LENGTH: 660
<212> TYPE: DNA
<213> ORGANISM: Escherichia coli
<220> FEATURE:
<223> OTHER INFORMATION: CAT

<400> SEQUENCE: 45
atggagaaaa aaatcactgg atataccacc gttgatatat cccaatggca tcgtaaagaa      60
cattttgagg catttcagtc agttgctcaa tgtacctata accagaccgt tcagctggat    120
attacggcct ttttaaagac cgtaaagaaa aataagcaca gtttttatcc ggcctttatt    180
cacattcttg cccgcctgat gaatgctcat ccggaactcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt ccctaaaggg tttattgag    420
aatatgttt tcgtctcagc caatccctgg gtgagtttca ccagttttga tttaaacgtg    480
gccaatatgg acaacttctt cgcccccgtt ttcacgatgg gcaaatatta tacgcaaggc    540
gacaaggtgc tgatgccgct ggcgattcag gttcatcatg ccgtttgtga tggcttccat    600
gtcggcagaa tgcttaatga attacaacag tactgcgatg agtggcaggg cggggcgtaa    660

<210> SEQ ID NO 46
<211> LENGTH: 609
<212> TYPE: DNA
<213> ORGANISM: Arabidopsis thaliana
<220> FEATURE:
<223> OTHER INFORMATION: G1543_delta1-73_L84A_L86A

<400> SEQUENCE: 46
atggcgattt tgccggaaaa ctcttcaaac gctgatgcta ctatctccgt tccaggcttc      60
tcttcatccc ctctctccga tgaaggaagt ggcggaggaa gagaccagct aaggctagac    120
atgaatcggt taccgtcgtc tgaagacgga gacgatgaag aattcagtca cgatgatggc    180
tctgctcctc cgcgaaagaa actccgtcta accagagaac agtcacgtct tcttgaagat    240
agtttcagac agaatcatac ccttaatccc aaacaaaagg aagtacttgc caagcatttg    300
atgctacggc caagacaaat tgaagtttgg tttcaaaacc gtagagcaag gagcaaattg    360
aagcaaaccg agatgaatg cgagtatctc aaaaggtggt ttggttcatt aacggaagaa    420
aaccacaggc tccatagaga agtagaagag cttagagcca taaaggttgg cccaacaacg    480
gtgaactctg cctcgagcct tactatgtgt cctcgctgcg agcgagttac ccctgccgcg    540
agcccttcga gggcggtggt gccggttccg gctaagaaaa cgtttccgcc gcaagagcgt    600
gatcgttga                                                           609

<210> SEQ ID NO 47
<211> LENGTH: 609
<212> TYPE: DNA
<213> ORGANISM: Arabidopsis thaliana
<220> FEATURE:
<223> OTHER INFORMATION: G1543_delta1-73

<400> SEQUENCE: 47
atggcgattt tgccggaaaa ctcttcaaac ttggatctta ctatctccgt tccaggcttc      60
tcttcatccc ctctctccga tgaaggaagt ggcggaggaa gagaccagct aaggctagac    120
atgaatcggt taccgtcgtc tgaagacgga gacgatgaag aattcagtca cgatgatggc    180
tctgctcctc cgcgaaagaa actccgtcta accagagaac agtcacgtct tcttgaagat    240
```

```
agtttcagac agaatcatac ccttaatccc aaacaaaagg aagtacttgc caagcatttg    300
atgctacggc aagacaaat tgaagtttgg tttcaaaacc gtagagcaag gagcaaattg     360
aagcaaaccg agatggaatg cgagtatctc aaaaggtggt ttggttcatt aacggaagaa    420
aaccacaggc tccatagaga agtagaagag cttagagcca taaaggttgg cccaacaacg    480
gtgaactctg cctcgagcct tactatgtgt cctcgctgcg agcgagttac ccctgccgcg    540
agcccttcga gggcggtggt gccggttccg gctaagaaaa cgtttccgcc gcaagagcgt    600
gatcgttag                                                           609
```

<210> SEQ ID NO 48
<211> LENGTH: 17
<212> TYPE: DNA
<213> ORGANISM: artificial sequence
<220> FEATURE:
<223> OTHER INFORMATION: the conserved DNA sequence that is recognized
      by HD-ZIP class II members

<400> SEQUENCE: 48

```
cagacaatca ttgcggc                                                   17
```

<210> SEQ ID NO 49
<211> LENGTH: 17
<212> TYPE: DNA
<213> ORGANISM: artificial sequence
<220> FEATURE:
<223> OTHER INFORMATION: the mutated DNA sequence based on SEQ ID NO:
      48, which is no longer recognized by HD-ZIP class II members

<400> SEQUENCE: 49

```
cagatcagtc tgacggc                                                   17
```

<210> SEQ ID NO 50
<211> LENGTH: 5
<212> TYPE: PRT
<213> ORGANISM: Arabidopsis thaliana
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<223> OTHER INFORMATION: the native EAR motif

<400> SEQUENCE: 50

Leu Xaa Leu Xaa Xaa
1               5

<210> SEQ ID NO 51
<211> LENGTH: 60
<212> TYPE: PRT
<213> ORGANISM: Arabidopsis thaliana
<220> FEATURE:
<223> OTHER INFORMATION: AtHB17 Homeodomain

<400> SEQUENCE: 51

Pro Pro Arg Lys Lys Leu Arg Leu Thr Arg Glu Gln Ser Arg Leu Leu
1               5                   10                  15

Glu Asp Ser Phe Arg Gln Asn His Thr Leu Asn Pro Lys Gln Lys Glu
            20                  25                  30

Val Leu Ala Lys His Leu Met Leu Arg Pro Arg Gln Ile Glu Val Trp

-continued

```
              35                  40                  45
Phe Gln Asn Arg Arg Ala Arg Ser Lys Leu Lys Gln
    50                  55                  60

<210> SEQ ID NO 52
<211> LENGTH: 60
<212> TYPE: PRT
<213> ORGANISM: Glycine max
<220> FEATURE:
<223> OTHER INFORMATION: G3524 Homeodomain

<400> SEQUENCE: 52

Pro Pro Arg Lys Lys Leu Arg Leu Thr Lys Glu Gln Ser Arg Leu Leu
1               5                  10                  15

Glu Glu Ser Phe Arg Gln Asn His Thr Leu Asn Pro Lys Gln Lys Glu
            20                  25                  30

Ser Leu Ala Met Gln Leu Lys Leu Arg Pro Arg Gln Val Glu Val Trp
        35                  40                  45

Phe Gln Asn Arg Arg Ala Arg Ser Lys Leu Lys Gln
    50                  55                  60

<210> SEQ ID NO 53
<211> LENGTH: 60
<212> TYPE: PRT
<213> ORGANISM: Oryza sativa
<220> FEATURE:
<223> OTHER INFORMATION: G3510 homeodomain

<400> SEQUENCE: 53

His Arg Pro Lys Lys Leu Arg Leu Ser Lys Glu Gln Ser Arg Leu Leu
1               5                  10                  15

Glu Glu Ser Phe Arg Leu Asn His Thr Leu Thr Pro Lys Gln Lys Glu
            20                  25                  30

Ala Leu Ala Ile Lys Leu Lys Leu Arg Pro Arg Gln Val Glu Val Trp
        35                  40                  45

Phe Gln Asn Arg Arg Ala Arg Thr Lys Leu Lys Gln
    50                  55                  60

<210> SEQ ID NO 54
<211> LENGTH: 60
<212> TYPE: PRT
<213> ORGANISM: Glycine max
<220> FEATURE:
<223> OTHER INFORMATION: G4371 homeodomain

<400> SEQUENCE: 54

Pro Pro Arg Lys Lys Leu Arg Leu Thr Lys Glu Gln Ser Leu Leu Leu
1               5                  10                  15

Glu Glu Ser Phe Arg Gln Asn His Thr Leu Asn Pro Lys Gln Lys Glu
            20                  25                  30

Ser Leu Ala Met Gln Leu Lys Leu Arg Pro Arg Gln Val Glu Val Trp
        35                  40                  45

Phe Gln Asn Arg Arg Ala Arg Ser Lys Leu Lys Gln
    50                  55                  60

<210> SEQ ID NO 55
<211> LENGTH: 60
<212> TYPE: PRT
<213> ORGANISM: Zea mays
<220> FEATURE:
<223> OTHER INFORMATION: G4369 homeodomain
```

-continued

<400> SEQUENCE: 55

His Arg Ala Lys Lys Leu Arg Leu Ser Lys Glu Gln Ser Arg Leu Leu
1               5                   10                  15

Glu Glu Ser Phe Arg Leu Asn His Thr Leu Thr Pro Lys Gln Lys Glu
            20                  25                  30

Ala Leu Ala Val Lys Leu Lys Leu Arg Pro Arg Gln Val Glu Val Trp
        35                  40                  45

Phe Gln Asn Arg Arg Ala Arg Thr Lys Leu Lys Gln
    50                  55                  60

<210> SEQ ID NO 56
<211> LENGTH: 60
<212> TYPE: PRT
<213> ORGANISM: Zea mays
<220> FEATURE:
<223> OTHER INFORMATION: G4370 homeodomain

<400> SEQUENCE: 56

His Arg Pro Lys Lys Leu Arg Leu Ser Lys Glu Gln Ser Arg Leu Leu
1               5                   10                  15

Glu Glu Ser Phe Arg Leu Asn His Thr Leu Ser Pro Lys Gln Lys Glu
            20                  25                  30

Ala Leu Ala Ile Lys Leu Lys Leu Arg Pro Arg Gln Val Glu Val Trp
        35                  40                  45

Phe Gln Asn Arg Arg Ala Arg Thr Lys Leu Lys His
    50                  55                  60

<210> SEQ ID NO 57
<211> LENGTH: 60
<212> TYPE: PRT
<213> ORGANISM: Arabidopsis thaliana
<220> FEATURE:
<223> OTHER INFORMATION: G2712 homeodomain

<400> SEQUENCE: 57

Arg Arg Arg Lys Lys Leu Arg Leu Thr Lys Glu Gln Ser His Leu Leu
1               5                   10                  15

Glu Glu Ser Phe Ile Gln Asn His Thr Leu Thr Pro Lys Gln Lys Lys
            20                  25                  30

Asp Leu Ala Thr Phe Leu Lys Leu Ser Gln Arg Gln Val Glu Val Trp
        35                  40                  45

Phe Gln Asn Arg Arg Ala Arg Ser Lys Leu Lys His
    50                  55                  60

<210> SEQ ID NO 58
<211> LENGTH: 60
<212> TYPE: PRT
<213> ORGANISM: Arabidopsis thaliana
<220> FEATURE:
<223> OTHER INFORMATION: G400 homeodomain

<400> SEQUENCE: 58

Asn Ser Arg Lys Lys Leu Arg Leu Ser Lys Asp Gln Ser Ala Ile Leu
1               5                   10                  15

Glu Glu Thr Phe Lys Asp His Ser Thr Leu Asn Pro Lys Gln Lys Gln
            20                  25                  30

Ala Leu Ala Lys Gln Leu Gly Leu Arg Ala Arg Gln Val Glu Val Trp
        35                  40                  45

Phe Gln Asn Arg Arg Ala Arg Thr Lys Leu Lys Gln
    50                  55                  60

```
<210> SEQ ID NO 59
<211> LENGTH: 54
<212> TYPE: PRT
<213> ORGANISM: Arabidopsis thaliana
<220> FEATURE:
<223> OTHER INFORMATION: G399 homeodomain

<400> SEQUENCE: 59

Thr Ser Arg Lys Lys Leu Arg Leu Ser Lys Asp Gln Ser Ala Phe Leu
1               5                   10                  15

Glu Glu Thr Phe Lys Glu His Asn Thr Leu Asn Pro Lys Gln Lys Leu
            20                  25                  30

Ala Leu Ala Lys Lys Leu Asn Leu Thr Ala Arg Gln Val Glu Val Trp
        35                  40                  45

Phe Gln Asn Arg Arg Ala
    50

<210> SEQ ID NO 60
<211> LENGTH: 60
<212> TYPE: PRT
<213> ORGANISM: Arabidopsis thaliana
<220> FEATURE:
<223> OTHER INFORMATION: G398 homeodomain

<400> SEQUENCE: 60

Thr Cys Arg Lys Lys Leu Arg Leu Ser Lys Asp Gln Ser Ala Val Leu
1               5                   10                  15

Glu Asp Thr Phe Lys Glu His Asn Thr Leu Asn Pro Lys Gln Lys Leu
            20                  25                  30

Ala Leu Ala Lys Lys Leu Gly Leu Thr Ala Arg Gln Val Glu Val Trp
        35                  40                  45

Phe Gln Asn Arg Arg Ala Arg Thr Lys Leu Lys Gln
    50                  55                  60

<210> SEQ ID NO 61
<211> LENGTH: 60
<212> TYPE: PRT
<213> ORGANISM: Sorghum bicolor
<220> FEATURE:
<223> OTHER INFORMATION: SbHB17 homeodomain

<400> SEQUENCE: 61

His Arg Ser Lys Lys Leu Arg Leu Ser Lys Glu Gln Ser Arg Leu Leu
1               5                   10                  15

Glu Glu Ser Phe Arg Phe Asn His Thr Pro Thr Pro Lys Gln Lys Glu
            20                  25                  30

Ala Leu Ala Gly Lys Leu Gln Leu Arg Pro Arg Gln Val Glu Val Trp
        35                  40                  45

Phe Gln Asn Arg Arg Ala Arg Thr Lys Leu Lys Gln
    50                  55                  60

<210> SEQ ID NO 62
<211> LENGTH: 60
<212> TYPE: PRT
<213> ORGANISM: Vitis vinifera
<220> FEATURE:
<223> OTHER INFORMATION: VvHB1 homeodomain

<400> SEQUENCE: 62

Pro Pro Arg Lys Lys Leu Arg Leu Ser Lys Asp Gln Ser Arg Leu Leu
1               5                   10                  15
```

Glu Glu Ser Phe Arg Gln Asn His Thr Leu Asn Pro Lys Gln Lys Glu
            20                  25                  30

Ala Leu Ala Met Gln Leu Lys Leu Arg Pro Arg Gln Val Glu Val Trp
            35                  40                  45

Phe Gln Asn Arg Arg Ala Arg Ser Lys Leu Lys Gln
            50                  55                  60

<210> SEQ ID NO 63
<211> LENGTH: 60
<212> TYPE: PRT
<213> ORGANISM: Carica papaya
<220> FEATURE:
<223> OTHER INFORMATION: CpHB17 homeodomain

<400> SEQUENCE: 63

Pro Pro Arg Lys Lys Leu Arg Leu Thr Lys Glu Gln Ser Arg Leu Leu
1               5                   10                  15

Glu Glu Ser Phe Arg Gln Asn His Thr Leu Asn Pro Lys Gln Lys Glu
            20                  25                  30

Thr Leu Ala Thr Gln Leu Lys Leu Arg Pro Arg Gln Val Glu Val Trp
            35                  40                  45

Phe Gln Asn Arg Arg Ala Arg Ser Lys Leu Lys Gln
            50                  55                  60

<210> SEQ ID NO 64
<211> LENGTH: 60
<212> TYPE: PRT
<213> ORGANISM: Populus trichocarpa
<220> FEATURE:
<223> OTHER INFORMATION: PtHB17 homeodomain

<400> SEQUENCE: 64

Pro Pro Arg Lys Lys Leu Arg Leu Ser Lys Glu Gln Ser Arg Leu Leu
1               5                   10                  15

Glu Glu Ser Phe Arg Gln His His Ser Leu Asn Pro Arg Gln Lys Glu
            20                  25                  30

Ala Leu Ala Leu Gln Leu Lys Leu Arg Pro Arg Gln Val Glu Val Trp
            35                  40                  45

Phe Gln Asn Arg Arg Ala Arg Ser Lys Leu Lys Gln
            50                  55                  60

<210> SEQ ID NO 65
<211> LENGTH: 60
<212> TYPE: PRT
<213> ORGANISM: Thellungiella halophila
<220> FEATURE:
<223> OTHER INFORMATION: ThHB17 homeodomain

<400> SEQUENCE: 65

Pro Pro Arg Lys Lys Leu Arg Leu Thr Arg Glu Gln Ser Arg Leu Leu
1               5                   10                  15

Glu Asp Ser Phe Arg Gln Asn His Thr Leu Asn Pro Lys Gln Lys Glu
            20                  25                  30

Ala Leu Ala Lys His Leu Met Leu Arg Pro Arg Gln Ile Glu Val Trp
            35                  40                  45

Phe Gln Asn Arg Arg Ala Arg Ser Lys Leu Lys Gln
            50                  55                  60

<210> SEQ ID NO 66
<211> LENGTH: 60

```
<212> TYPE: PRT
<213> ORGANISM: Ricinus communis
<220> FEATURE:
<223> OTHER INFORMATION: RcHB17 homeodomain

<400> SEQUENCE: 66

Pro Pro Arg Lys Lys Leu Arg Leu Ser Lys Glu Gln Ser Arg Leu Leu
1               5                   10                  15

Glu Glu Ser Phe Arg Gln His His Thr Leu Asn Pro Arg Gln Lys Glu
                20                  25                  30

Ala Leu Ala Met Gln Leu Lys Leu Arg Pro Arg Gln Val Glu Val Trp
            35                  40                  45

Phe Gln Asn Arg Arg Ala Arg Ser Lys Leu Lys Gln
        50                  55                  60

<210> SEQ ID NO 67
<211> LENGTH: 60
<212> TYPE: PRT
<213> ORGANISM: Arabidopsis lyrata
<220> FEATURE:
<223> OTHER INFORMATION: AlHB18 homeodomain

<400> SEQUENCE: 67

Arg Arg Arg Lys Lys Leu Arg Leu Thr Lys Glu Gln Ser His Leu Leu
1               5                   10                  15

Glu Glu Ser Phe Ile Gln Asn His Thr Leu Thr Pro Lys Gln Lys Lys
                20                  25                  30

Asp Leu Ala Thr Phe Leu Lys Leu Ser Gln Arg Gln Val Glu Val Trp
            35                  40                  45

Phe Gln Asn Arg Arg Ala Arg Ser Lys Leu Lys His
        50                  55                  60

<210> SEQ ID NO 68
<211> LENGTH: 60
<212> TYPE: PRT
<213> ORGANISM: Arabidopsis lyrata
<220> FEATURE:
<223> OTHER INFORMATION: G4369 homeodomain

<400> SEQUENCE: 68

Pro Pro Arg Lys Lys Leu Arg Leu Thr Arg Glu Gln Ser Arg Leu Leu
1               5                   10                  15

Glu Asp Ser Phe Arg Gln Asn His Thr Leu Asn Pro Lys Gln Lys Glu
                20                  25                  30

Ala Leu Ala Lys His Leu Met Leu Arg Pro Arg Gln Ile Glu Val Trp
            35                  40                  45

Phe Gln Asn Arg Arg Ala Arg Ser Lys Leu Lys Gln
        50                  55                  60

<210> SEQ ID NO 69
<211> LENGTH: 60
<212> TYPE: PRT
<213> ORGANISM: Arabidopsis thaliana

<400> SEQUENCE: 69

Pro Pro Arg Lys Lys Leu Arg Leu Thr Arg Glu Gln Ser Arg Leu Leu
1               5                   10                  15

Glu Asp Ser Phe Arg Gln Asn His Thr Leu Asn Pro Lys Gln Lys Glu
                20                  25                  30

Val Leu Ala Lys His Leu Met Leu Arg Pro Arg Gln Ile Glu Val Trp
            35                  40                  45
```

Phe Gln Asn Arg Arg Ala Arg Ser Lys Leu Lys Gln
        50                  55                  60

<210> SEQ ID NO 70
<211> LENGTH: 42
<212> TYPE: PRT
<213> ORGANISM: Arabidopsis thaliana

<400> SEQUENCE: 70

Thr Glu Met Glu Cys Glu Tyr Leu Lys Arg Trp Phe Gly Ser Leu Thr
1               5                   10                  15

Glu Glu Asn His Arg Leu His Arg Glu Val Glu Glu Leu Arg Ala Ile
            20                  25                  30

Lys Val Gly Pro Thr Thr Val Asn Ser Ala
        35                  40

<210> SEQ ID NO 71
<211> LENGTH: 41
<212> TYPE: PRT
<213> ORGANISM: Glycine max

<400> SEQUENCE: 71

Thr Glu Met Glu Cys Glu Tyr Leu Lys Arg Trp Phe Gly Ser Leu Thr
1               5                   10                  15

Glu Gln Asn Arg Arg Leu Gln Arg Glu Val Glu Glu Leu Arg Ala Ile
            20                  25                  30

Lys Val Gly Pro Pro Thr Val Ile Ser
        35                  40

<210> SEQ ID NO 72
<211> LENGTH: 41
<212> TYPE: PRT
<213> ORGANISM: Oryza sativa

<400> SEQUENCE: 72

Thr Glu Met Glu Cys Glu Tyr Leu Lys Arg Cys Phe Gly Ser Leu Thr
1               5                   10                  15

Glu Glu Asn Arg Arg Leu Gln Arg Glu Val Glu Glu Leu Arg Ala Met
            20                  25                  30

Arg Val Ala Pro Pro Thr Val Leu Ser
        35                  40

<210> SEQ ID NO 73
<211> LENGTH: 41
<212> TYPE: PRT
<213> ORGANISM: Glycine max

<400> SEQUENCE: 73

Thr Glu Met Glu Cys Glu Tyr Leu Lys Arg Trp Phe Gly Ser Leu Thr
1               5                   10                  15

Glu Gln Asn Arg Arg Leu Gln Arg Glu Val Glu Glu Leu Arg Ala Ile
            20                  25                  30

Lys Val Gly Pro Pro Thr Val Ile Ser
        35                  40

<210> SEQ ID NO 74
<211> LENGTH: 41
<212> TYPE: PRT
<213> ORGANISM: Zea mays

<400> SEQUENCE: 74

```
Thr Glu Leu Glu Cys Glu Tyr Leu Lys Arg Cys Phe Gly Ser Leu Thr
1               5                   10                  15

Glu Glu Asn Arg Arg Leu Gln Arg Glu Val Glu Leu Arg Ala Met
            20                  25                  30

Arg Val Ala Pro Pro Thr Val Leu Ser
        35                  40

<210> SEQ ID NO 75
<211> LENGTH: 41
<212> TYPE: PRT
<213> ORGANISM: Zea mays

<400> SEQUENCE: 75

Thr Glu Met Glu Cys Glu Tyr Leu Lys Arg Cys Phe Gly Ser Leu Thr
1               5                   10                  15

Glu Glu Asn Arg Arg Leu Gln Arg Glu Val Glu Leu Arg Ala Met
            20                  25                  30

Arg Met Ala Pro Pro Thr Val Leu Ser
        35                  40

<210> SEQ ID NO 76
<211> LENGTH: 38
<212> TYPE: PRT
<213> ORGANISM: Arabidopsis thaliana

<400> SEQUENCE: 76

Thr Glu Met Glu Cys Glu Tyr Leu Lys Arg Trp Phe Gly Ser Leu Lys
1               5                   10                  15

Glu Gln Asn Arg Arg Leu Gln Ile Glu Val Glu Leu Arg Ala Leu
            20                  25                  30

Lys Pro Ser Ser Thr Ser
        35

<210> SEQ ID NO 77
<211> LENGTH: 41
<212> TYPE: PRT
<213> ORGANISM: Arabidopsis thaliana

<400> SEQUENCE: 77

Thr Glu Val Asp Cys Glu Phe Leu Arg Arg Cys Cys Glu Asn Leu Thr
1               5                   10                  15

Glu Glu Asn Arg Arg Leu Gln Lys Glu Val Thr Glu Leu Arg Ala Leu
            20                  25                  30

Lys Leu Ser Pro Gln Phe Tyr Met His
        35                  40

<210> SEQ ID NO 78
<211> LENGTH: 41
<212> TYPE: PRT
<213> ORGANISM: Arabidopsis thaliana

<400> SEQUENCE: 78

Thr Glu Val Asp Cys Glu Tyr Leu Lys Arg Cys Val Glu Lys Leu Thr
1               5                   10                  15

Glu Glu Asn Arg Arg Leu Gln Lys Glu Ala Met Glu Leu Arg Thr Leu
            20                  25                  30

Lys Leu Ser Pro Gln Phe Tyr Gly Gln
        35                  40
```

```
<210> SEQ ID NO 79
<211> LENGTH: 41
<212> TYPE: PRT
<213> ORGANISM: Arabidopsis thaliana

<400> SEQUENCE: 79

Thr Glu Val Asp Cys Glu Tyr Leu Lys Arg Cys Val Glu Lys Leu Thr
1               5                   10                  15

Glu Glu Asn Arg Arg Leu Glu Lys Glu Ala Ala Glu Leu Arg Ala Leu
            20                  25                  30

Lys Leu Ser Pro Arg Leu Tyr Gly Gln
        35                  40

<210> SEQ ID NO 80
<211> LENGTH: 41
<212> TYPE: PRT
<213> ORGANISM: Sorghum bicolor

<400> SEQUENCE: 80

Thr Glu Leu Glu Cys Gly Tyr Leu Lys Arg Cys Phe Gly Ser Leu Thr
1               5                   10                  15

Glu Glu Asn Arg Arg Leu Gln Arg Glu Val Glu Glu Leu Arg Ala Met
            20                  25                  30

Arg Val Ala Pro Pro Thr Val Leu Ser
        35                  40

<210> SEQ ID NO 81
<211> LENGTH: 41
<212> TYPE: PRT
<213> ORGANISM: Vitis vinifera

<400> SEQUENCE: 81

Thr Glu Met Glu Cys Gly Tyr Leu Lys Arg Trp Phe Gly Ser Leu Thr
1               5                   10                  15

Glu Gln Asn Arg Arg Leu Gln Arg Glu Val Glu Glu Leu Arg Ala Met
            20                  25                  30

Lys Val Ala Pro Pro Thr Val Ile Ser
        35                  40

<210> SEQ ID NO 82
<211> LENGTH: 41
<212> TYPE: PRT
<213> ORGANISM: Carica papaya

<400> SEQUENCE: 82

Thr Glu Met Glu Cys Gly Tyr Leu Lys Arg Trp Phe Gly Ser Leu Thr
1               5                   10                  15

Glu Gln Asn Arg Arg Leu Gln Arg Glu Val Glu Glu Leu Arg Ala Met
            20                  25                  30

Lys Val Gly Pro Pro Thr Val Ile Ser
        35                  40

<210> SEQ ID NO 83
<211> LENGTH: 41
<212> TYPE: PRT
<213> ORGANISM: Populus trichocarpa

<400> SEQUENCE: 83

Thr Glu Met Glu Cys Gly Tyr Leu Lys Arg Trp Phe Gly Ser Leu Thr
1               5                   10                  15

Glu Gln Asn Arg Arg Leu Gln Arg Glu Val Glu Glu Leu Arg Ala Leu
```

-continued

```
                 20                  25                  30

Lys Val Gly Pro Pro Thr Val Ile Ser
            35                  40

<210> SEQ ID NO 84
<211> LENGTH: 41
<212> TYPE: PRT
<213> ORGANISM: Thellungiella halophila

<400> SEQUENCE: 84

Thr Glu Met Glu Cys Glu Tyr Leu Lys Arg Trp Phe Gly Ser Leu Thr
1               5                   10                  15

Glu Gln Asn His Arg Leu His Arg Glu Val Glu Glu Leu Arg Thr Met
                20                  25                  30

Lys Val Gly Pro Pro Thr Val Thr Ser
            35                  40

<210> SEQ ID NO 85
<211> LENGTH: 41
<212> TYPE: PRT
<213> ORGANISM: Ricinus communis

<400> SEQUENCE: 85

Thr Glu Met Glu Cys Glu Tyr Leu Lys Arg Trp Phe Gly Ser Leu Thr
1               5                   10                  15

Glu Gln Asn Arg Arg Leu Gln Arg Glu Val Glu Glu Leu Arg Ala Met
                20                  25                  30

Lys Val Gly Pro Pro Thr Val Leu Ser
            35                  40

<210> SEQ ID NO 86
<211> LENGTH: 36
<212> TYPE: PRT
<213> ORGANISM: Arabidopsis lyrata

<400> SEQUENCE: 86

Thr Glu Met Glu Cys Glu Tyr Leu Lys Arg Trp Phe Gly Ser Leu Lys
1               5                   10                  15

Glu Gln Asn Arg Arg Leu Gln Ile Glu Val Glu Glu Leu Arg Ala Leu
                20                  25                  30

Lys Pro Ser Ser
            35

<210> SEQ ID NO 87
<211> LENGTH: 41
<212> TYPE: PRT
<213> ORGANISM: Arabidopsis lyrata

<400> SEQUENCE: 87

Thr Glu Met Glu Cys Glu Tyr Leu Lys Arg Trp Phe Gly Ser Leu Thr
1               5                   10                  15

Glu Gln Asn His Arg Leu His Arg Glu Val Glu Glu Leu Arg Ala Met
                20                  25                  30

Lys Val Gly Pro Thr Thr Val Asn Ser
            35                  40

<210> SEQ ID NO 88
<211> LENGTH: 42
<212> TYPE: PRT
<213> ORGANISM: Arabidopsis thaliana
```

<400> SEQUENCE: 88

```
Thr Glu Met Glu Cys Glu Tyr Leu Lys Arg Trp Phe Gly Ser Leu Thr
1               5                   10                  15

Glu Glu Asn His Arg Leu His Arg Glu Val Glu Glu Leu Arg Ala Met
            20                  25                  30

Lys Val Gly Pro Thr Thr Val Asn Ser Ala
        35                  40
```

<210> SEQ ID NO 89
<211> LENGTH: 5
<212> TYPE: PRT
<213> ORGANISM: arabidopsis thaliana
<220> FEATURE:
<223> OTHER INFORMATION: The mutant EAR motif in AtHB17 L84A L86A

<400> SEQUENCE: 89

```
Ala Asp Ala Thr Ile
1               5
```

<210> SEQ ID NO 90
<211> LENGTH: 34
<212> TYPE: DNA
<213> ORGANISM: artificial sequence
<220> FEATURE:
<223> OTHER INFORMATION: site-direct mutagenesis for generating of
      AtHB17 L84A L86A

<400> SEQUENCE: 90
cgacggcggc cgcaatggcg attttgccgg aaaa        34

<210> SEQ ID NO 91
<211> LENGTH: 33
<212> TYPE: DNA
<213> ORGANISM: artificial sequence
<220> FEATURE:
<223> OTHER INFORMATION: site direct mutagenesis oligo for generating
      AtHB17 L84A L86A

<400> SEQUENCE: 91
gtgcgcccgg gtcaacgatc acgctcttgc ggc        33

<210> SEQ ID NO 92
<211> LENGTH: 254
<212> TYPE: PRT
<213> ORGANISM: Arabidopsis thaliana
<220> FEATURE:
<223> OTHER INFORMATION: AtHB17 delta21

<400> SEQUENCE: 92

```
Met Asp Tyr Ala Cys Val Cys Met Tyr Lys Tyr Lys Gly Ile Val Thr
1               5                   10                  15

Leu Gln Val Cys Leu Phe Tyr Ile Lys Leu Arg Val Phe Leu Ser Asn
            20                  25                  30

Phe Thr Phe Ser Ser Ser Ile Leu Ala Leu Lys Asn Pro Asn Asn Ser
        35                  40                  45

Leu Ile Lys Ile Met Ala Ile Leu Pro Glu Asn Ser Ser Asn Leu Asp
    50                  55                  60

Leu Thr Ile Ser Val Pro Gly Phe Ser Ser Pro Leu Ser Asp Glu
65                  70                  75                  80

Gly Ser Gly Gly Gly Arg Asp Gln Leu Arg Leu Asp Met Asn Arg Leu
                85                  90                  95

Pro Ser Ser Glu Asp Gly Asp Asp Glu Glu Phe Ser His Asp Asp Gly
```

```
                100                 105                 110
Ser Ala Pro Pro Arg Lys Lys Leu Arg Leu Thr Arg Glu Gln Ser Arg
            115                 120                 125

Leu Leu Glu Asp Ser Phe Arg Gln Asn His Thr Leu Asn Pro Lys Gln
        130                 135                 140

Lys Glu Val Leu Ala Lys His Leu Met Leu Arg Pro Arg Gln Ile Glu
145                 150                 155                 160

Val Trp Phe Gln Asn Arg Arg Ala Arg Ser Lys Leu Lys Gln Thr Glu
                165                 170                 175

Met Glu Cys Glu Tyr Leu Lys Arg Trp Phe Gly Ser Leu Thr Glu Glu
            180                 185                 190

Asn His Arg Leu His Arg Glu Val Glu Glu Leu Arg Ala Ile Lys Val
        195                 200                 205

Gly Pro Thr Thr Val Asn Ser Ala Ser Ser Leu Thr Met Cys Pro Arg
    210                 215                 220

Cys Glu Arg Val Thr Pro Ala Ala Ser Pro Ser Arg Ala Val Val Pro
225                 230                 235                 240

Val Pro Ala Lys Lys Thr Phe Pro Pro Gln Glu Arg Asp Arg
                245                 250

<210> SEQ ID NO 93
<211> LENGTH: 254
<212> TYPE: PRT
<213> ORGANISM: Arabidopsis thaliana
<220> FEATURE:
<223> OTHER INFORMATION: AtHB17 delta21_L63A_L65A
      (also known as "G1543-NNO-d21_L63A_L65A")

<400> SEQUENCE: 93

Met Asp Tyr Ala Cys Val Cys Met Tyr Lys Tyr Lys Gly Ile Val Thr
1               5                   10                  15

Leu Gln Val Cys Leu Phe Tyr Ile Lys Leu Arg Val Phe Leu Ser Asn
            20                  25                  30

Phe Thr Phe Ser Ser Ser Ile Leu Ala Leu Lys Asn Pro Asn Asn Ser
        35                  40                  45

Leu Ile Lys Ile Met Ala Ile Leu Pro Glu Asn Ser Asn Ala Asp
    50                  55                  60

Ala Thr Ile Ser Val Pro Gly Phe Ser Ser Pro Leu Ser Asp Glu
65                  70                  75                  80

Gly Ser Gly Gly Gly Arg Asp Gln Leu Arg Leu Asp Met Asn Arg Leu
                85                  90                  95

Pro Ser Ser Glu Asp Gly Asp Asp Glu Glu Phe Ser His Asp Asp Gly
            100                 105                 110

Ser Ala Pro Pro Arg Lys Lys Leu Arg Leu Thr Arg Glu Gln Ser Arg
        115                 120                 125

Leu Leu Glu Asp Ser Phe Arg Gln Asn His Thr Leu Asn Pro Lys Gln
    130                 135                 140

Lys Glu Val Leu Ala Lys His Leu Met Leu Arg Pro Arg Gln Ile Glu
145                 150                 155                 160

Val Trp Phe Gln Asn Arg Arg Ala Arg Ser Lys Leu Lys Gln Thr Glu
                165                 170                 175

Met Glu Cys Glu Tyr Leu Lys Arg Trp Phe Gly Ser Leu Thr Glu Glu
            180                 185                 190

Asn His Arg Leu His Arg Glu Val Glu Glu Leu Arg Ala Ile Lys Val
        195                 200                 205
```

```
Gly Pro Thr Thr Val Asn Ser Ala Ser Ser Leu Thr Met Cys Pro Arg
    210                 215                 220

Cys Glu Arg Val Thr Pro Ala Ala Ser Pro Ser Arg Ala Val Val Pro
225                 230                 235                 240

Val Pro Ala Lys Lys Thr Phe Pro Pro Gln Glu Arg Asp Arg
                245                 250

<210> SEQ ID NO 94
<211> LENGTH: 762
<212> TYPE: DNA
<213> ORGANISM: arabidopsis thaliana
<220> FEATURE:
<223> OTHER INFORMATION: coding sequence for AtHB17 delta21_L63A_L65A
      (also known as "G1543-NNO-d21_L63A_L65A")

<400> SEQUENCE: 94
atggactacg cctgcgtgtg catgtacaag tacaagggca tcgtgaccct ccaagtgtgc      60
ctcttctaca ttaagctgag ggtgttcctc tccaacttca ccttctccag ctccatcctc    120
gccctcaaga accctaacaa tagcctcatc aagatcatgg ccatcctccc tgagaactcc    180
agcaacgcgg acgcgaccat ctccgtgccc ggcttctcca gctctccctt gtccgacgag    240
ggcagcggcg gtgggcgcga ccagcttcgc ctggacatga accgcctgcc cagctctgag    300
gacggtgacg atgaggaatt ctctcacgat gatgggtctg ctcctcctcg caagaaactg    360
aggctgacta gggagcagtc tcgcctgctt gaggatagtt tccgccagaa ccacactctg    420
aacccgaagc agaaggaggt cttggctaag caccttatgc ttcgcccgag gcagattgag    480
gtctggtttc agaataggcg tgctaggtcg aagttgaagc agactgagat ggagtgcgag    540
tatcttaagc gttggtttgg atcgcttact gaggagaatc atcgtttaca tagagaagtc    600
gaggaactac gggctatcaa ggtcggaccc acgacagtca attcagcgtc atcactaacg    660
atgtgtccca gatgtgagcg ggttacgcca gcggcatcgc cgagtcgggc ggttgtaccg    720
gttccagcaa agaagacatt cccaccacaa gaaagagatc gc                       762
```